US012571796B2

(12) United States Patent
Wang et al.

(10) Patent No.: US 12,571,796 B2
(45) Date of Patent: Mar. 10, 2026

(54) VIRAL EXPOSURE SIGNATURE FOR DETECTION OF EARLY STAGE HEPATOCELLULAR CARCINOMA

(71) Applicant: The U.S.A., as represented by the Secretary, Department of Health and Human Services, Bethesda, MD (US)

(72) Inventors: Xin Wei Wang, Rockville, MD (US); Jinping Liu, Wynnewood, PA (US); Wei Tang, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 1014 days.

(21) Appl. No.: 17/766,015

(22) PCT Filed: Oct. 9, 2020

(86) PCT No.: PCT/US2020/055077
§ 371 (c)(1),
(2) Date: Apr. 1, 2022

(87) PCT Pub. No.: WO2021/072268
PCT Pub. Date: Apr. 15, 2021

(65) Prior Publication Data
US 2023/0003730 A1     Jan. 5, 2023

Related U.S. Application Data

(60) Provisional application No. 62/914,138, filed on Oct. 11, 2019.

(51) Int. Cl.
| | |
|---|---|
| *A61P 1/16* | (2006.01) |
| *C12N 15/10* | (2006.01) |
| *C40B 40/02* | (2006.01) |
| *G01N 33/569* | (2006.01) |
| *G01N 33/574* | (2006.01) |

(52) U.S. Cl.
CPC .......... *G01N 33/56983* (2013.01); *A61P 1/16* (2018.01); *C12N 15/1037* (2013.01); *C40B 40/02* (2013.01); *G01N 33/57438* (2013.01)

(58) Field of Classification Search
None
See application file for complete search history.

(56) References Cited

FOREIGN PATENT DOCUMENTS

WO      WO 2017/132550      8/2017

OTHER PUBLICATIONS

Xu et al. Comprehensive serological profiling of human populations using a synthetic human virome. Science. Jun. 5, 2015; 348(6239): aaa0698.*
International Search Report and Written Opinion for PCT/US2020/055077, dated Feb. 24, 2021 (10 pages).
Liu et al., "A Viral Exposure Signature Defines Early Onset of Hepatocellular Carcinoma," *Cell*, vol. 182:317-328, 2020.
Mohan et al., "PhIP-Seq Characterization of Serum Antibodies Using Oligonucleotide-Encoded Peptidomes," *Nat Protoc*, vol. 13:1958-1978, 2018.
Stern et al., "Virome and Bacteriome: Two Sides of the Same Coin," *Curr. Opin. Virol.*, vol. 37:37-43, 2019.
Xu et al., "Comprehensive Serological Profiling of Human Populations using a Synthetic Human Virome," *Science*, vol. 348:aaa0698, with Supplementary Materials, 2015 (32 pages).
Xu et al., "Comprehensive Serological Profiling of Human Populations using a Synthetic Human Virome," Research Article Summary in *Science*, vol. 348:1105, 2015.

* cited by examiner

*Primary Examiner* — Nianxiang Zou
(74) *Attorney, Agent, or Firm* — Klarquist Sparkman, LLP

(57) ABSTRACT

A viral exposure signature (VES) that can identify early stage, pre-symptomatic hepatocellular carcinoma (HCC) among at-risk patients is described. The VES was developed using serological profiling and synthetic virome technology to identify unique viral peptide epitopes corresponding to 61 viral species. Methods of identifying a subject with early stage (pre-symptomatic) HCC using the VES are described.

13 Claims, 37 Drawing Sheets
Specification includes a Sequence Listing.

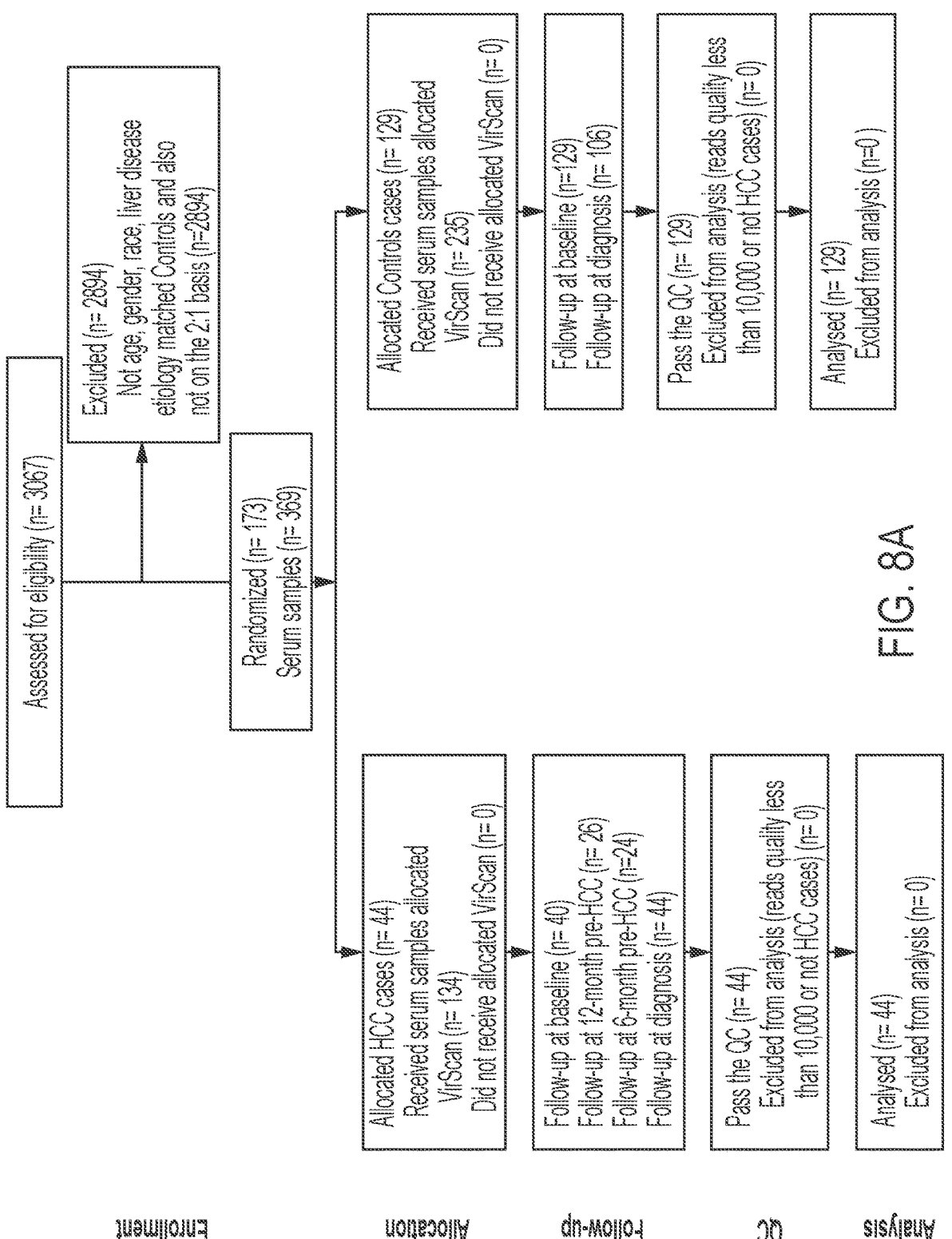

Assessed for eligibility (n= 3067)

Excluded (n= 2894)
Not age, gender, race, liver disease
etiology matched Controls and also
not on the 2:1 basis (n=2894)

Randomized (n= 173)
Serum samples (n= 369)

Allocated Controls cases (n= 129)
Received serum samples allocated
VirScan (n= 235)
Did not receive allocated VirScan (n= 0)

Follow-up at baseline (n=129)
Follow-up at diagnosis (n= 106)

Pass the QC (n= 129)
Excluded from analysis (reads quality less
than 10,000 or not HCC cases) (n= 0)

Analysed (n= 129)
Excluded from analysis (n=0)

Allocated HCC cases (n= 44)
Received serum samples allocated
VirScan (n= 134)
Did not receive allocated VirScan (n= 0)

Follow-up at baseline (n= 40)
Follow-up at 12-month pre-HCC (n= 26)
Follow-up at 6-month pre-HCC (n=24)
Follow-up at diagnosis (n= 44)

Pass the QC (n= 44)
Excluded from analysis (reads quality less
than 10,000 or not HCC cases) (n= 0)

Analysed (n= 44)
Excluded from analysis (n= 0)

Enrollment          Allocation          Follow-up          QC          Analysis

FIG. 8A

SEQUENCE LISTING

<160> NUMBER OF SEQ ID NOS: 102

<210> SEQ ID NO 1
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 1

Glu Leu Ser Asp Thr Thr Asn Ala Thr Gln Pro Glu Leu Val Pro Glu
1               5                   10                  15

Asp Pro Glu Asp Ser Ala Leu Leu Glu Asp Pro Ala Gly Thr Val Ser
            20                  25                  30

Ser Gln Ile Pro Pro Asn Trp His Ile Pro Ser Ile Gln Asp Val Ala
        35                  40                  45

Pro His His Ala Pro Ala Ala Pro
    50                  55

<210> SEQ ID NO 2
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 2

Glu Val Val Glu Thr Ala Asn Val Thr Arg Pro Glu Leu Ala Pro Glu
1               5                   10                  15

Glu Arg Gly Thr Ser Arg Thr Pro Gly Asp Glu Pro Ala Pro Ala Val
            20                  25                  30

Ala Ala Gln Leu Pro Pro Asn Trp His Val Pro Glu Ala Ser Asp Val
        35                  40                  45

Thr Ile Gln Gly Pro Ala Pro Ala
    50                  55

<210> SEQ ID NO 3
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 3

Glu Lys Pro Asn Ala Thr Asp Thr Pro Ile Glu Glu Ile Gly Asp Ser
1               5                   10                  15

Gln Asn Thr Glu Pro Ser Val Asn Ser Gly Phe Asp Pro Asp Lys Phe
            20                  25                  30

Arg Glu Ala Gln Glu Met Ile Lys Tyr Met Thr Leu Val Ser Ala Ala
        35                  40                  45

Glu Arg Gln Glu Ser Lys Ala Arg
    50                  55

<210> SEQ ID NO 4
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 4

Thr Pro Ser Ala Glu Ser Thr Pro Gln Ser Thr Thr Val Lys Thr Lys

-continued

```
1               5                    10                   15

Asn Thr Thr Thr Thr Gln Ile Gln Pro Ser Lys Pro Thr Thr Lys Gln
            20                   25                   30

Arg Gln Asn Lys Pro Gln Asn Lys Pro Asn Asn Asp Phe His Phe Glu
        35                   40                   45

Val Phe Asn Phe Val Pro Cys Ser
    50                   55
```

```
<210> SEQ ID NO 5
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 5

Ile Asp Tyr Asp Asp Asn Lys Asp Asp Asp Lys Asp Asp Asp Lys Asp
1               5                    10                   15

Asp Asn Lys Asp Asp Asp Lys Asp Asp Asn Lys Asp Asp Asp Lys Asp
            20                   25                   30

Asp Lys Asp Asp Asn Lys Asp Asp Asp Ser Asp Ser Asp Ser Asp Ser
        35                   40                   45

Asp Ser Asp Ser Asp Ser Asp Asp
    50                   55
```

```
<210> SEQ ID NO 6
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 6

Leu Tyr Ser His Ile Lys Glu Glu Asp Arg Arg Arg Ser Ser Ala Ala
1               5                    10                   15

Gln Ala Met Glu Ala Ile Phe Gln Gly Ile Asp Leu Gln Ser Pro Pro
            20                   25                   30

Pro Pro Ala Ile Ala Asp Leu Leu Arg Ser Val Lys Thr Pro Glu Ile
        35                   40                   45

Ile Lys Tyr Cys Gln Asp Asn Asn
    50                   55
```

```
<210> SEQ ID NO 7
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 7

Met Ser Asn Met Asp Ile Asp Gly Ile Asn Thr Gly Thr Ile Asp Lys
1               5                    10                   15

Thr Pro Glu Glu Ile Thr Ser Gly Thr Ser Gly Thr Thr Arg Pro Ile
            20                   25                   30

Ile Arg Pro Ala Thr Leu Ala Pro Pro Ser Asn Lys Arg Thr Arg Asn
        35                   40                   45

Pro Ser Pro Glu Arg Ala Thr Thr
    50                   55
```

```
<210> SEQ ID NO 8
```

```
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 8

Leu Tyr Gln Gln Tyr Asp Glu Met Glu Glu Cys Ser Gln Ser Ala Pro
1               5                   10                  15

Tyr Ile Glu Gln Ala Gln Ala Ile Ala Gln Gln Phe Lys Asp Lys Val
            20                  25                  30

Leu Gly Leu Leu Gln Arg Ala Ser Gln Gln Glu Ala Glu Ile Arg Pro
        35                  40                  45

Ile Val Gln Ser Gln Trp Gln Lys
    50                  55

<210> SEQ ID NO 9
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 9

Tyr Pro Gly His Val Ser Gly His Arg Met Ala Trp Asp Met Met Met
1               5                   10                  15

Asn Trp Ser Pro Thr Thr Ala Leu Val Val Ser Gln Leu Leu Arg Ile
            20                  25                  30

Pro Gln Ala Val Val Asp Met Val Ala Gly Ala His Trp Gly Val Leu
        35                  40                  45

Ala Gly Leu Ala Tyr Tyr Ser Met
    50                  55

<210> SEQ ID NO 10
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 10

Arg Arg Lys Arg Thr Val Gln Leu Thr Glu Ser Val Val Ser Thr Ala
1               5                   10                  15

Leu Ala Glu Leu Ala Ala Lys Thr Phe Gly Gln Ser Glu Pro Ser Ser
            20                  25                  30

Asp Arg Asp Thr Asp Leu Thr Thr Pro Thr Glu Thr Thr Asp Ser Gly
        35                  40                  45

Pro Ile Val Val Asp Asp Ala Ser
    50                  55

<210> SEQ ID NO 11
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 11

Leu Thr Val Thr Tyr Ser Ser His Thr Thr Ser Ala Ala His Ser Arg
1               5                   10                  15

Ser Gly Ser Val Ser Gln Arg Val Thr Ser Ser Gln Thr Val Ser His
            20                  25                  30
```

-continued

```
Gly Val Asn Glu Thr Ile Tyr Asn Thr Thr Leu Lys Tyr Gly Asp Val
        35                  40                  45

Val Gly Val Asn Thr Thr Lys Tyr
    50                  55

<210> SEQ ID NO 12
<211> LENGTH: 49
<212> TYPE: PRT
<213> ORGANISM: Artificial Sequence
<220> FEATURE:
<223> OTHER INFORMATION: Synthetic peptide epitope

<400> SEQUENCE: 12

Cys Ile Thr Pro Asn Gly Ser Ile Pro Asn Asp Lys Pro Phe Gln Asn
1               5                   10                  15

Val Asn Lys Ile Thr Tyr Gly Ala Cys Pro Lys Tyr Val Lys Gln Asn
            20                  25                  30

Thr Leu Lys Leu Ala Thr Gly Met Arg Asn Val Pro Glu Lys Gln Thr
        35                  40                  45

Arg

<210> SEQ ID NO 13
<211> LENGTH: 36
<212> TYPE: PRT
<213> ORGANISM: Artificial Sequence
<220> FEATURE:
<223> OTHER INFORMATION: Synthetic peptide epitope

<400> SEQUENCE: 13

Thr Ser Gly Ala Thr Ala Ala Ala Ser Ala Ala Ala Ala Val Asp Thr
1               5                   10                  15

Gly Ser Gly Gly Gly Gly Gln Pro His Asp Thr Ala Pro Arg Gly Ala
            20                  25                  30

Arg Lys Lys Gln
        35

<210> SEQ ID NO 14
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 14

Met Thr Ser Arg Pro Ala Asp Gln Asp Ser Val Arg Ser Ser Ala Ser
1               5                   10                  15

Val Pro Leu Tyr Pro Ala Ala Ser Pro Val Pro Ala Glu Ala Tyr Tyr
            20                  25                  30

Ser Glu Ser Glu Asp Glu Ala Ala Asn Asp Phe Leu Val Arg Met Gly
        35                  40                  45

Arg Gln Gln Ser Val Leu Arg Arg
    50                  55

<210> SEQ ID NO 15
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 15
```

-continued

```
Met Glu Pro Pro Arg Pro Pro Asp Ala Asp Ser Leu Leu Ser Asp Ala
1               5               10              15

Thr Ser Val Ile Pro Leu Thr Pro Pro Ala Gln Gly Ala Glu Ala Tyr
            20              25              30

Tyr Thr Glu Ser Asp Asp Glu Thr Ala Ala Asp Phe Leu Met Arg Met
        35              40              45

Gly Arg Gln Gln Thr Ala Leu Arg
    50              55
```

```
<210> SEQ ID NO 16
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 16

Asn Phe Ile Lys Ile Ser Leu Gly Glu Thr Met Gly Ile Thr Pro Lys
1               5               10              15

Glu Pro Thr Asn Pro Thr Gln Leu Leu Asn Val Lys Asn Gln Thr Glu
            20              25              30

Tyr Ala Asn Glu Thr His Ser Thr Glu Val Gln Thr Val Lys Thr Phe
        35              40              45

Lys Glu Asp Arg Phe Gln Arg Thr
    50              55
```

```
<210> SEQ ID NO 17
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 17

Glu Asp Glu Tyr Leu Ser Glu Glu Met Met Glu Leu Thr Ala Arg Ala
1               5               10              15

Leu Glu Arg Gly Asn Gly Glu Trp Ser Thr Asp Ala Ala Leu Glu Val
            20              25              30

Ala His Glu Ala Glu Ala Leu Val Ser Gln Leu Gly Asn Ala Gly Glu
        35              40              45

Val Phe Asn Phe Gly Asp Phe Gly
    50              55
```

```
<210> SEQ ID NO 18
<211> LENGTH: 30
<212> TYPE: PRT
<213> ORGANISM: Artificial Sequence
<220> FEATURE:
<223> OTHER INFORMATION: Synthetic peptide epitope

<400> SEQUENCE: 18

Arg Arg His Thr Gln Lys Ala Pro Lys Arg Ile Arg Leu Pro His Ile
1               5               10              15

Arg Glu Asp Asp Gln Pro Ser Ser His Gln Pro Leu Phe Tyr
            20              25              30
```

```
<210> SEQ ID NO 19
<211> LENGTH: 56
<212> TYPE: PRT
<213> ORGANISM: Artificial Sequence
<220> FEATURE:
<223> OTHER INFORMATION: Synthetic peptide epitope
```

<400> SEQUENCE: 19

Gln Pro Pro Leu Glu Ala Pro Tyr Val Pro Pro Arg Tyr Leu Ala Pro
1               5                   10                  15

Thr Glu Gly Arg Asn Ser Ile Arg Tyr Ser Glu Leu Thr Pro Leu Tyr
                20                  25                  30

Asp Thr Thr Arg Leu Tyr Leu Val Asp Asn Lys Ser Ala Asp Ile Ala
            35                  40                  45

Ser Leu Asn Tyr Gln Asn Asp His
    50                  55

<210> SEQ ID NO 20
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 20

Ser Gly Ser Arg Glu Ser Gly Ser Arg Glu Ser Gly Ser Arg Glu Ser
1               5                   10                  15

Gly Ser Arg Glu Val Arg Glu Ser Gly Val Arg Glu Thr Glu Val Gln
                20                  25                  30

Val Val Arg Val Arg Gln Glu Ser Gly Gly Arg Val Thr Ala Pro Ser
            35                  40                  45

Glu Ser Arg Lys Lys Phe Leu Asp
    50                  55

<210> SEQ ID NO 21
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 21

Gln Asn Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asn Asp
                20                  25                  30

Gln Ile Glu Val Thr Asn Ala Thr Glu Leu Val Gln Ser Ser Ser Thr
            35                  40                  45

Gly Arg Ile Cys Asp Ser Pro His
    50                  55

<210> SEQ ID NO 22
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 22

Thr Glu Leu Tyr Thr Ser Ala Ala Ser Arg Lys Pro Asp Pro Ala Val
1               5                   10                  15

Ala Pro Thr Ser Ala Ala Ser Arg Lys Pro Asp Pro Ala Val Ala Pro
                20                  25                  30

Thr Ser Ala Ala Thr Arg Lys Pro Asp Pro Ala Val Ala Pro Thr Ser
            35                  40                  45

Ala Ala Thr Arg Lys Pro Asp Pro

-continued

```
        50                  55

<210> SEQ ID NO 23
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 23

Leu Ser Ser Met Ala Val Thr Phe Lys Arg Ala Leu Gly Gly Arg Ala
1               5                   10                  15

Lys Gln Pro Pro Pro Arg Glu Thr Pro Gln Arg Pro Pro Arg Pro Pro
            20                  25                  30

Thr Pro Glu Leu Val Lys Lys Ile Pro Pro Pro Pro Asn Gly Glu
        35                  40                  45

Asp Glu Leu Val Val Ser Tyr Ser
        50                  55

<210> SEQ ID NO 24
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 24

Met Lys Met Ala Ser Asn Asp Ala Ser Ala Ala Val Ala Asn Ser
1               5                   10                  15

Asn Asn Asp Thr Ala Lys Ser Ser Ser Asp Gly Val Leu Ser Ser Met
            20                  25                  30

Ala Ile Thr Phe Lys Arg Ala Leu Gly Ala Arg Pro Lys Gln Pro Pro
        35                  40                  45

Pro Arg Glu Ile Leu Gln Arg Pro
    50                  55

<210> SEQ ID NO 25
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 25

Met Asp Gly Thr Leu Phe Pro Gly Asp Asp Leu Ala Ile Pro Ala
1               5                   10                  15

Thr Glu Phe Phe Ser Thr Lys Ala Asp Lys Lys Pro Glu Ala Lys Arg
            20                  25                  30

Glu Ala Ile Val Lys Ala Asp Glu Asp Asp Asn Glu Glu Thr Leu Lys
        35                  40                  45

Gln Arg Leu Thr Asn Leu Glu Lys
    50                  55

<210> SEQ ID NO 26
<211> LENGTH: 49
<212> TYPE: PRT
<213> ORGANISM: Artificial Sequence
<220> FEATURE:
<223> OTHER INFORMATION: Synthetic peptide epitope

<400> SEQUENCE: 26

Asp Ala Asp Asp His Ala Ala Ser Phe Gly Gly Leu Ala Ala Ala Ala
```

-continued

```
1               5                   10                  15

Ala Gly Ala Ala Gly Val Ala Arg Lys Arg Ala Phe His Gly Asp Asp
            20                  25                  30

Pro Phe Gly Glu Gly Pro Pro Glu Lys Lys Asp Leu Thr Leu Asp Met
        35                  40                  45

Leu

<210> SEQ ID NO 27
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 27

Lys Gly Ile Ile Ala Gln Asn Pro Ile Glu Asn Tyr Val Asp Glu Val
1               5                   10                  15

Leu Asn Glu Val Leu Val Val Pro Asn Ile Asn Ser Ser His Pro Thr
            20                  25                  30

Thr Ser Asn Ser Ala Pro Ala Leu Asp Ala Ala Glu Thr Gly His Thr
        35                  40                  45

Ser Asn Val Gln Pro Glu Asp Val
    50                  55

<210> SEQ ID NO 28
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 28

Met Gly Ser Lys Cys Cys Lys Thr Ile His Gly Gly Ile Phe Ser Lys
1               5                   10                  15

Ala Glu Asp Thr Leu Val Asp Tyr Lys Gly Lys Tyr Ile Asn Leu Glu
            20                  25                  30

Lys Glu Phe Ser Ala Leu Ser Asp Thr Glu Ser Glu Glu Glu Leu Gln
        35                  40                  45

Leu Glu Lys Pro Leu Leu Asn Lys
    50                  55

<210> SEQ ID NO 29
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 29

Met Asp Phe Met Ser Lys Tyr Ser Lys Glu Leu Val Leu Thr Ala Lys
1               5                   10                  15

Asn Ile Lys Asp Glu Glu Pro Asn Leu Asn Lys Lys Glu Thr Ser Phe
            20                  25                  30

Asp Leu Ser Thr Tyr Leu Lys Thr Lys Glu Thr His Tyr Gln Lys Lys
        35                  40                  45

Ile Arg Asp Gln Leu Ala Glu Lys
    50                  55

<210> SEQ ID NO 30
<211> LENGTH: 56
```

```
<212> TYPE: PRT
<213> ORGANISM: Artificial Sequence
<220> FEATURE:
<223> OTHER INFORMATION: Synthetic peptide epitope

<400> SEQUENCE: 30

Ile Asp Asn Thr Val Arg Glu Thr Val Gly Ala Ala Thr Ser Arg Asp
1               5                   10                  15

Ala Leu Pro Asn Thr Glu Ala Ser Gly Pro Ala His Ser Lys Glu Ile
            20                  25                  30

Pro Ala Leu Thr Ala Val Glu Thr Gly Ala Thr Asn Pro Leu Val Pro
        35                  40                  45

Ser Asp Thr Val Gln Thr Arg His
    50                  55

<210> SEQ ID NO 31
<211> LENGTH: 39
<212> TYPE: PRT
<213> ORGANISM: Artificial Sequence
<220> FEATURE:
<223> OTHER INFORMATION: Synthetic peptide epitope

<400> SEQUENCE: 31

Arg Leu Asn Lys Arg Leu Asn Asp Lys Lys Lys Gln Gly Ser Gln Pro
1               5                   10                  15

Ser Thr Asn Pro Thr Asn Arg Thr Asn Gln Asp Glu Ile Asp Asp Leu
            20                  25                  30

Phe Asn Ala Phe Gly Ser Asn
        35

<210> SEQ ID NO 32
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 32

Thr Thr Asn Ala Thr Gln Lys Ile Glu Ser Thr Thr Phe Thr Thr Ile
1               5                   10                  15

Gly Ile Lys Glu Ile Asn Gly Asn Thr Tyr Ser Ser Pro Lys Asn Ser
            20                  25                  30

Ile Tyr Leu Lys Ser Lys Ser Gln Gln Ser Thr Thr Lys Phe Thr Asp
        35                  40                  45

Ala Glu His Thr Thr Pro Ile Leu
    50                  55

<210> SEQ ID NO 33
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 33

Met Ser Thr Asn Gly Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45
```

Thr Arg Lys Thr Trp Glu Arg Ser
    50                  55

<210> SEQ ID NO 34
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 34

Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser
    50                  55

<210> SEQ ID NO 35
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 35

Met Ser Thr Asn Pro Lys Pro Gln Arg Gln Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser
    50                  55

<210> SEQ ID NO 36
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 36

Asn Ile Thr Arg Val Glu Ala Glu Asn Lys Val Glu Ile Leu Asp Cys
1               5                   10                  15

Phe Lys Pro Leu Lys Glu Glu Glu Asp Asp Arg Glu Ile Ser Val Ser
            20                  25                  30

Ala Asp Cys Phe Lys Lys Gly Pro Ala Phe Pro Pro Ala Leu Pro Val
        35                  40                  45

Trp Ala Arg Pro Gly Tyr Asp Pro
    50                  55

<210> SEQ ID NO 37
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 37

```
Val Arg Leu Pro His Ile Tyr His Glu Gly Val Phe Ile Pro Gly Thr
1               5                   10                  15

Tyr Lys Ile Val Ile Asp Lys Lys Asn Lys Leu Asn Asp Arg Cys Thr
            20                  25                  30

Leu Phe Thr Asp Cys Val Ile Lys Gly Arg Glu Val Arg Lys Gly Gln
        35                  40                  45

Ser Val Leu Arg Gln Tyr Lys Thr
    50                  55
```

<210> SEQ ID NO 38
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 38

```
Met Ser Thr Ile Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser
    50                  55
```

<210> SEQ ID NO 39
<211> LENGTH: 28
<212> TYPE: PRT
<213> ORGANISM: Artificial Sequence
<220> FEATURE:
<223> OTHER INFORMATION: Synthetic peptide epitope

<400> SEQUENCE: 39

```
Ser Ser Ala Gly Leu Lys Asn Asp Leu Leu Glu Asn Leu Gln Ala Tyr
1               5                   10                  15

Gln Lys Arg Met Gly Val Gln Met Gln Arg Phe Lys
            20                  25
```

<210> SEQ ID NO 40
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 40

```
Ile Thr Arg Val Glu Ser Glu Asn Lys Ile Val Val Leu Asp Ser Phe
1               5                   10                  15

Asp Pro Leu Val Ala Glu Glu Asp Arg Glu Ile Ser Ile Pro Ala
            20                  25                  30

Glu Ile Leu Arg Lys Phe Lys Gln Phe Pro Pro Ala Met Pro Ile Trp
        35                  40                  45

Ala Arg Pro Asp Tyr Asn Pro Pro
    50                  55
```

<210> SEQ ID NO 41
<211> LENGTH: 56
<212> TYPE: PRT
<213> ORGANISM: Artificial Sequence
<220> FEATURE:
<223> OTHER INFORMATION: Synthetic peptide epitope -continued

<400> SEQUENCE: 41

```
Val Lys Lys Arg Glu Asn Met Phe Ile Asp Glu Arg Pro Gly Asn Arg
1               5                   10                  15

Asn Pro Tyr Glu Asn Leu Leu Tyr Lys Leu Cys Leu Ser Gly Glu Gly
            20                  25                  30

Trp Pro Tyr Ile Gly Ser Arg Ser Gln Val Lys Gly Arg Ser Trp Glu
        35                  40                  45

Asn Thr Thr Val Asp Leu Ser Leu
    50                  55
```

<210> SEQ ID NO 42
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 42

```
Glu Asp Ile Glu Thr Asp Thr Asp Ile Glu Ser Thr Glu Asp Glu Asp
1               5                   10                  15

Glu Ala Asp Arg Phe Asp Ile Ile Asp Thr Ser Asp Glu Glu Asp Glu
            20                  25                  30

Asn Glu Thr Asp Arg Val Thr Leu Leu Ser Thr Leu Val Asn Gln Gly
        35                  40                  45

Met Thr Met Thr Arg Ala Thr Arg
    50                  55
```

<210> SEQ ID NO 43
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 43

```
Met Ala Pro Lys Lys Lys Leu Gln Leu Pro Pro Pro Thr Asp Glu
1               5                   10                  15

Glu Glu Tyr Trp Asp Ser Gln Ala Glu Glu Val Leu Asp Glu Glu Glu
            20                  25                  30

Glu Asp Met Met Glu Asp Trp Glu Ser Leu Asp Glu Glu Ala Ser Glu
        35                  40                  45

Val Glu Glu Val Ser Asp Glu Thr
    50                  55
```

<210> SEQ ID NO 44
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 44

```
Glu Pro Pro Ala Gly Ile Leu Ala Gly Pro Gln Val Lys Pro Gln Glu
1               5                   10                  15

Lys Pro Pro Ala Glu Pro Pro Ala Gly Leu Pro Ala Gly Pro Gln Ala
            20                  25                  30

Lys Pro Pro Val Lys Pro Gln Ala Lys Pro Pro Ala Glu Pro Pro Val
        35                  40                  45

Gly Ile Leu Ala Gly Pro Gln Ala
```

50                    55

<210> SEQ ID NO 45
<211> LENGTH: 36
<212> TYPE: PRT
<213> ORGANISM: Artificial Sequence
<220> FEATURE:
<223> OTHER INFORMATION: Synthetic peptide epitope

<400> SEQUENCE: 45

Thr Ala Ser Gly Glu Glu Val Ala Val Leu Ser His His Asp Ser Leu
1               5                   10                  15

Glu Ser Arg Arg Leu Arg Glu Glu Glu Asp Asp Asp Asp Asp Glu Asp
            20                  25                  30

Phe Glu Asp Ala
        35

<210> SEQ ID NO 46
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 46

Gly Ser Ser Thr Thr Ser Gly Val Thr Ser Gly Glu Ala Ala Glu Ser
1               5                   10                  15

Ser Pro Ala Pro Ser Cys Asp Gly Glu Leu Asp Ser Glu Ala Glu Ser
            20                  25                  30

Tyr Ser Ser Met Pro Pro Leu Glu Gly Glu Pro Gly Asp Pro Asp Leu
        35                  40                  45

Ser Asp Gly Ser Trp Ser Thr Val
    50                  55

<210> SEQ ID NO 47
<211> LENGTH: 39
<212> TYPE: PRT
<213> ORGANISM: Artificial Sequence
<220> FEATURE:
<223> OTHER INFORMATION: Synthetic peptide epitope

<400> SEQUENCE: 47

Leu Asp Gly Gln Thr Gly Thr Gln Asp Lys Gly Gln Lys Pro Asn Leu
1               5                   10                  15

Leu Asp Arg Leu Arg His Arg Lys Asn Gly Tyr Arg His Leu Lys Asp
            20                  25                  30

Ser Asp Glu Glu Glu Asn Val
        35

<210> SEQ ID NO 48
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 48

Thr Gly Ser Ser Gln Ala Ala Pro Ser Ser Ser Ser Val Ala Pro Val
1               5                   10                  15

Ala Ser Leu Ser Gly Asp Leu Glu Glu Glu Glu Glu Gly Ser Arg Glu
            20                  25                  30

Ser Pro Ser Leu Pro Ser Ser Lys Lys Gly Ala Asp Glu Phe Glu Ala

-continued

```
              35                  40                  45

Trp Leu Glu Ala Gln Asp Ala Asn
    50                  55

<210> SEQ ID NO 49
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 49

Gln His Phe Arg Lys Leu Leu Leu Asp Glu Glu Ala Gly Pro Leu
1               5                   10                  15

Glu Glu Glu Leu Pro Arg Leu Ala Asp Glu Gly Leu Asn Arg Arg Val
                20                  25                  30

Ala Glu Asp Leu Asn Leu Gly Asn Leu Asn Val Ser Ile Pro Trp Thr
        35                  40                  45

His Lys Val Gly Asn Phe Thr Gly
    50                  55

<210> SEQ ID NO 50
<211> LENGTH: 46
<212> TYPE: PRT
<213> ORGANISM: Artificial Sequence
<220> FEATURE:
<223> OTHER INFORMATION: Synthetic peptide epitope

<400> SEQUENCE: 50

Pro Ser Met Gln Gly Ile Pro Glu Ser Arg Phe Thr Arg Thr Gly Glu
1               5                   10                  15

Gly Leu Asp Val Arg Gly Ser Arg Gly Phe Pro Gln Asp Ile Leu Phe
                20                  25                  30

Pro Ser Asp Pro Pro Phe Ser Pro Gln Ser Cys Arg Pro Gln
        35                  40                  45

<210> SEQ ID NO 51
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 51

Val Ile Val Gly Arg Ile Ile Leu Ser Gly Lys Pro Ala Val Val Pro
1               5                   10                  15

Asp Arg Glu Val Leu Tyr Gln Glu Phe Asp Glu Met Glu Glu Cys Ala
                20                  25                  30

Ser Gln Leu Pro Tyr Ile Glu Gln Gly Met Gln Leu Ala Glu Gln Phe
        35                  40                  45

Lys Gln Lys Ala Leu Gly Leu Leu
    50                  55

<210> SEQ ID NO 52
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 52

Gly Gly Asn Asn Ser Gly Ser Gly Ala Glu Glu Asn Ser Asn Ala Ala
```

```
1               5               10              15

Ala Ala Ala Met Gln Pro Val Glu Asp Met Asn Asp His Ala Ile Arg
            20              25              30

Gly Asp Thr Phe Ala Thr Arg Ala Glu Glu Lys Arg Ala Glu Ala Glu
            35              40              45

Ala Ala Ala Glu Ala Ala Ala Pro
        50              55
```

```
<210> SEQ ID NO 53
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 53

Thr Gly Gln Val Tyr Leu Leu Ser Phe Ile Ser Ala Cys Pro Asp Phe
1               5               10              15

Lys Leu Arg Leu Met Lys Asp Thr Gln Thr Ile Ser Gln Thr Val Ala
            20              25              30

Leu Thr Glu Gly Leu Gly Asp Glu Leu Glu Glu Val Ile Val Glu Lys
        35              40              45

Thr Lys Gln Thr Val Ala Ser Ile
        50              55
```

```
<210> SEQ ID NO 54
<211> LENGTH: 30
<212> TYPE: PRT
<213> ORGANISM: Artificial Sequence
<220> FEATURE:
<223> OTHER INFORMATION: Synthetic peptide epitope

<400> SEQUENCE: 54

Asn Phe Ser Ser Leu Gly Leu Thr Asp Glu Glu Lys Glu Ala Ala Glu
1               5               10              15

His Phe Leu Asn Val Ser Asp Asp Ser Gln Asn Asp Tyr Glu
            20              25              30
```

```
<210> SEQ ID NO 55
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 55

Gln Val Glu Pro Thr Ala Ala Asn Thr Asn Ala Ser Glu His Arg Leu
1               5               10              15

Gly Thr Gly Leu Val Pro Ala Leu Gln Ala Ala Glu Thr Gly Ala Ser
            20              25              30

Ser Asn Ala Gln Asp Glu Asn Leu Ile Glu Thr Arg Cys Val Leu Asn
        35              40              45

His His Ser Thr Gln Glu Thr Thr
        50              55
```

```
<210> SEQ ID NO 56
<211> LENGTH: 56
<212> TYPE: PRT
<213> ORGANISM: Artificial Sequence
<220> FEATURE:
<223> OTHER INFORMATION: Synthetic peptide epitope
```

<400> SEQUENCE: 56

Glu Gly Val Leu Arg Cys Tyr His Gly Leu Glu Met Ile Gln Lys Glu
1               5                   10                  15

Gln Leu Val Glu Met Asp Val Ala Ser Glu Asn Ala Gln Arg Ala Leu
            20                  25                  30

Lys Glu His Pro Ser Arg Ala Lys Val Val Gln Asn Arg Trp Gly Arg
        35                  40                  45

Ser Val Val Gln Leu Lys Asn Asp
    50                  55

<210> SEQ ID NO 57
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 57

Thr Gly Gln Val His Leu Leu Ser Phe Ile Ser Ala Cys Pro Asp Phe
1               5                   10                  15

Lys Leu Arg Leu Met Lys Asp Thr Gln Thr Ile Ser Gln Thr Asp Ala
            20                  25                  30

Leu Thr Glu Gly Leu Gly Asp Glu Leu Glu Glu Val Ile Val Glu Lys
        35                  40                  45

Thr Lys Gln Thr Leu Ala Ser Val
    50                  55

<210> SEQ ID NO 58
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 58

Glu Glu Gln Glu Gln Glu Leu Glu Glu Gln Glu Gln Glu Leu Glu Glu
1               5                   10                  15

Gln Glu Gln Glu Leu Glu Glu Gln Glu Gln Glu Leu Glu Glu Gln Glu
            20                  25                  30

Gln Glu Leu Glu Glu Gln Glu Gln Glu Leu Glu Glu Gln Glu Gln Glu
        35                  40                  45

Leu Glu Glu Gln Glu Gln Glu Leu
    50                  55

<210> SEQ ID NO 59
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 59

Ala Gln Ala Gln Gln Ala Gln Gln Ala Gln Ala Gln Gln Ala Gln Gln
1               5                   10                  15

Ala Gln Gln Ala Gln Gln Ala Gln Gln Ala Gln Gln Ala Gln Gln Ala
            20                  25                  30

Gln Ala Gln Gln Ala Gln Gln Ala Gln Gln Ala Gln Ala Gln Gln Ala
        35                  40                  45

Gln Ala Gln Gln Ala Gln Ala Gln
    50                  55

<210> SEQ ID NO 60
<211> LENGTH: 23
<212> TYPE: PRT
<213> ORGANISM: Artificial Sequence
<220> FEATURE:
<223> OTHER INFORMATION: Synthetic peptide epitope

<400> SEQUENCE: 60

Ser Gly Ser Gly Pro Arg His Arg Asp Gly Ala Arg Arg Pro Pro Lys
1               5                   10                  15

Arg Pro Ser Cys Ile Gly Cys
            20

<210> SEQ ID NO 61
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 61

Ser Ala Ile Gly Asn Thr Ile Glu Ala Leu Phe Gln Gly Pro Pro Lys
1               5                   10                  15

Phe Arg Pro Ile Arg Ile Ser Leu Glu Glu Lys Pro Ala Pro Asp Ala
            20                  25                  30

Ile Ser Asp Leu Leu Ala Ser Val Asp Ser Glu Glu Val Arg Gln Tyr
        35                  40                  45

Cys Arg Glu Gln Gly Trp Ile Ile
    50                  55

<210> SEQ ID NO 62
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 62

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Ala Arg Lys Thr Ser Glu Arg Ser
    50                  55

<210> SEQ ID NO 63
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 63

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser
    50                  55

<210> SEQ ID NO 64
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 64

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser
    50                  55

<210> SEQ ID NO 65
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 65

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser
    50                  55

<210> SEQ ID NO 66
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 66

Met Ser Thr Asn Pro Lys Pro Gln Arg Lys Thr Lys Arg Asn Thr Asn
1               5                   10                  15

Arg Arg Pro Glu Asp Val Lys Phe Pro Gly Gly Gly Gln Ile Val Gly
            20                  25                  30

Gly Val Tyr Leu Leu Pro Arg Arg Gly Pro Arg Leu Gly Val Arg Thr
        35                  40                  45

Thr Arg Lys Thr Ser Glu Arg Ser
    50                  55

<210> SEQ ID NO 67
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 67

```
Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala
        35                  40                  45

Thr Arg Lys Thr Ser Glu Arg Ser
    50                  55
```

```
<210> SEQ ID NO 68
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 68
```

```
Met Ser Thr Leu Pro Lys Pro Gln Arg Ile Thr Lys Arg Asn Ile Asn
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Lys Leu Gly Val Arg Ala
        35                  40                  45

Val Arg Lys Thr Ser Glu Arg Ser
    50                  55
```

```
<210> SEQ ID NO 69
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 69
```

```
Met Ser Thr Leu Pro Lys Pro Lys Arg Gln Thr Lys Arg Asn Thr Leu
1               5                   10                  15

Arg Arg Pro Lys Asn Val Lys Phe Pro Ala Gly Gly Gln Ile Val Gly
            20                  25                  30

Glu Val Tyr Val Leu Pro Arg Arg Gly Pro Gln Leu Gly Val Arg Glu
        35                  40                  45

Val Arg Lys Thr Ser Glu Arg Ser
    50                  55
```

```
<210> SEQ ID NO 70
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 70
```

```
Gln Ile Val Gly Gly Val Tyr Leu Leu Pro Arg Arg Gly Pro Arg Leu
1               5                   10                  15

Gly Val Arg Ala Ala Arg Lys Thr Ser Glu Arg Ser Gln Pro Arg Gly
            20                  25                  30

Arg Arg Gln Pro Ile Pro Lys Asp Arg Arg Ser Thr Gly Lys Ser Trp
        35                  40                  45

Gly Arg Pro Gly Tyr Pro Trp Pro
    50                  55
```

```
<210> SEQ ID NO 71
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 71

Gln Ile Val Gly Gly Val Tyr Leu Leu Pro Arg Arg Gly Pro Arg Leu
1               5                   10                  15

Gly Val Arg Ala Thr Arg Lys Thr Ser Glu Arg Ser Gln Pro Arg Gly
            20                  25                  30

Arg Arg Gln Pro Ile Pro Lys Asp Arg Arg Ser Thr Gly Lys Ser Trp
        35                  40                  45

Gly Lys Pro Gly Tyr Pro Trp Pro
    50                  55

<210> SEQ ID NO 72
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 72

Gln Ile Val Gly Gly Val Tyr Leu Leu Pro Arg Arg Gly Pro Arg Leu
1               5                   10                  15

Gly Val Arg Ala Thr Arg Lys Thr Ser Glu Arg Ser Gln Pro Arg Gly
            20                  25                  30

Arg Arg Gln Pro Ile Pro Lys Asp Arg Arg Ser Thr Gly Lys Ser Trp
        35                  40                  45

Gly Lys Pro Gly Tyr Pro Trp Pro
    50                  55

<210> SEQ ID NO 73
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 73

Gln Ile Val Gly Glu Val Tyr Val Leu Pro Arg Arg Gly Pro Gln Leu
1               5                   10                  15

Gly Val Arg Glu Val Arg Lys Thr Ser Glu Arg Ser Gln Pro Arg Gly
            20                  25                  30

Arg Arg Gln Pro Thr Pro Lys Ala Arg Pro Arg Glu Gly Arg Ser Trp
        35                  40                  45

Ala Gln Pro Gly Tyr Pro Trp Pro
    50                  55

<210> SEQ ID NO 74
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 74

Gln Ile Val Gly Gly Val Tyr Leu Leu Pro Arg Arg Gly Pro Arg Leu
1               5                   10                  15
```

```
Gly Val Arg Thr Thr Arg Lys Thr Ser Glu Arg Ser Gln Pro Arg Gly
            20                  25                  30

Arg Arg Gln Pro Ile Pro Lys Asp Arg Arg Ser Thr Gly Lys Ala Trp
        35                  40                  45

Gly Lys Pro Gly Arg Pro Trp Pro
    50                  55

<210> SEQ ID NO 75
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 75

Gln Pro Arg Gly Arg Arg Gln Pro Thr Pro Lys Ala Arg Pro Arg Glu
1               5                   10                  15

Gly Arg Ser Trp Ala Gln Pro Gly Tyr Pro Trp Pro Leu Tyr Gly Asn
            20                  25                  30

Glu Gly Cys Gly Trp Ala Gly Trp Leu Leu Pro Pro Arg Gly Ser Arg
        35                  40                  45

Pro Ser Trp Gly Gln Asn Asp Pro
    50                  55

<210> SEQ ID NO 76
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 76

Gln Pro Arg Gly Arg Arg Gln Pro Ile Pro Lys Asp Arg Arg Ser Thr
1               5                   10                  15

Gly Lys Ser Trp Gly Lys Pro Gly Tyr Pro Trp Pro Leu Tyr Gly Asn
            20                  25                  30

Glu Gly Leu Gly Trp Ala Gly Trp Leu Leu Ser Pro Arg Gly Ser Arg
        35                  40                  45

Pro Ser Trp Gly Pro Asn Asp Pro
    50                  55

<210> SEQ ID NO 77
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 77

Gln Pro Arg Gly Arg Arg Gln Pro Ile Pro Lys Ala Arg Arg Ser Glu
1               5                   10                  15

Gly Arg Ser Trp Ala Gln Pro Gly Tyr Pro Trp Pro Leu Tyr Gly Asn
            20                  25                  30

Glu Gly Cys Gly Trp Ala Gly Trp Leu Leu Ser Pro Arg Gly Ser Arg
        35                  40                  45

Pro Ser Trp Gly Pro Asn Asp Pro
    50                  55

<210> SEQ ID NO 78
<211> LENGTH: 56
<212> TYPE: PRT
```

```
<213> ORGANISM: Artificial Sequence
<220> FEATURE:
<223> OTHER INFORMATION: Synthetic peptide epitope

<400> SEQUENCE: 78

Leu Tyr Gly Asn Glu Gly Leu Gly Trp Ala Gly Trp Leu Leu Ser Pro
1               5                   10                  15

Arg Gly Ser Arg Pro Ser Trp Gly Pro Thr Asp Pro Arg His Arg Ser
            20                  25                  30

Arg Asn Val Gly Lys Val Ile Asp Thr Leu Thr Cys Gly Phe Ala Asp
        35                  40                  45

Leu Met Gly Tyr Ile Pro Val Val
    50                  55

<210> SEQ ID NO 79
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 79

Leu Tyr Gly Asn Glu Gly Leu Gly Trp Ala Gly Trp Leu Leu Ser Pro
1               5                   10                  15

Arg Gly Ser Arg Pro Ser Trp Gly Pro Asn Asp Pro Arg His Arg Ser
            20                  25                  30

Arg Asn Val Gly Lys Val Ile Asp Thr Leu Thr Cys Gly Phe Ala Asp
        35                  40                  45

Leu Met Gly Tyr Ile Pro Val Val
    50                  55

<210> SEQ ID NO 80
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 80

Leu Tyr Gly Asn Glu Gly Cys Gly Trp Ala Gly Trp Leu Leu Ser Pro
1               5                   10                  15

Arg Gly Ser Arg Pro Thr Trp Gly Pro Ser Asp Pro Arg His Arg Ser
            20                  25                  30

Arg Asn Leu Gly Arg Val Ile Asp Thr Ile Thr Cys Gly Phe Ala Asp
        35                  40                  45

Leu Met Gly Tyr Ile Pro Val Val
    50                  55

<210> SEQ ID NO 81
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 81

Leu Tyr Gly Asn Glu Gly Leu Gly Trp Ala Gly Trp Leu Leu Ser Pro
1               5                   10                  15

Arg Gly Ser Arg Pro Ser Trp Gly Pro Thr Asp Pro Arg His Arg Ser
            20                  25                  30

Arg Asn Leu Gly Lys Val Ile Asp Thr Leu Thr Cys Gly Phe Ala Asp
```

-continued

```
              35                    40                    45

Leu Met Gly Tyr Ile Pro Val Val
    50                    55

<210> SEQ ID NO 82
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 82

His Ile Asn Arg Thr Ala Leu Asn Cys Asn Asp Ser Leu Glu Thr Gly
1                   5                   10                  15

Phe Leu Ala Ala Leu Phe Tyr Thr Ser Ser Phe Asn Ser Ser Gly Cys
              20                    25                    30

Pro Glu Arg Leu Ala Ala Cys Arg Ser Ile Glu Ser Phe Arg Ile Gly
          35                    40                    45

Trp Gly Ser Leu Glu Tyr Glu Glu
    50                    55

<210> SEQ ID NO 83
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 83

Gln Ala Ala Cys Asn Phe Thr Arg Gly Asp Arg Cys Asn Leu Glu Asp
1                   5                   10                  15

Arg Asp Arg Ser Gln Leu Ser Pro Leu Leu His Ser Thr Thr Glu Trp
              20                    25                    30

Ala Ile Leu Pro Cys Ser Tyr Thr Asp Leu Pro Ala Leu Ser Thr Gly
          35                    40                    45

Leu Leu His Leu His Gln Asn Ile
    50                    55

<210> SEQ ID NO 84
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 84

Cys Gly Pro Val Tyr Cys Phe Thr Pro Ser Pro Val Val Val Gly Thr
1                   5                   10                  15

Thr Asp Arg Ala Gly Ala Pro Thr Tyr Asn Trp Gly Glu Asn Glu Thr
              20                    25                    30

Asp Val Phe Leu Leu Asn Ser Thr Arg Pro Pro Lys Gly Ala Trp Phe
          35                    40                    45

Gly Cys Thr Trp Met Asn Gly Thr
    50                    55

<210> SEQ ID NO 85
<211> LENGTH: 56
<212> TYPE: PRT
<213> ORGANISM: Artificial Sequence
<220> FEATURE:
<223> OTHER INFORMATION: Synthetic peptide epitope
```

<400> SEQUENCE: 85

```
Cys Gly Pro Val Tyr Cys Phe Thr Pro Ser Pro Val Val Val Gly Thr
1               5                   10                  15

Thr Asp Arg Arg Gly Val Pro Thr Tyr Thr Trp Gly Glu Asn Asp Thr
            20                  25                  30

Asp Val Phe Leu Leu Asn Ser Thr Arg Pro Pro Arg Gly Ala Trp Phe
        35                  40                  45

Gly Cys Thr Trp Met Asn Ser Thr
    50                  55
```

<210> SEQ ID NO 86
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 86

```
Cys Gly Pro Val Tyr Cys Phe Thr Pro Ser Pro Val Val Val Gly Thr
1               5                   10                  15

Thr Asp Arg Gln Gly Val Pro Thr Tyr Asn Trp Gly Asp Asn Glu Thr
            20                  25                  30

Asp Val Phe Leu Leu Asn Ser Thr Arg Pro Pro Arg Gly Ala Trp Phe
        35                  40                  45

Gly Cys Thr Trp Met Asn Gly Thr
    50                  55
```

<210> SEQ ID NO 87
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 87

```
Gly Phe Thr Lys Thr Cys Gly Ala Pro Pro Cys Arg Ile Arg Lys Asp
1               5                   10                  15

Tyr Asn Ser Thr Ile Asp Leu Leu Cys Pro Thr Asp Cys Phe Arg Lys
            20                  25                  30

His Pro Asp Ala Thr Tyr Leu Lys Cys Gly Ala Gly Pro Trp Leu Thr
        35                  40                  45

Pro Arg Cys Leu Val Asp Tyr Pro
    50                  55
```

<210> SEQ ID NO 88
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 88

```
Thr Gly Cys Ile Ser Ile Ile Gly Arg Ile His Leu Asn Asp Gln Val
1               5                   10                  15

Val Val Ala Pro Asp Lys Glu Ile Leu Tyr Glu Ala Phe Asp Glu Met
            20                  25                  30

Glu Glu Cys Ala Ser Lys Ala Ala Leu Ile Glu Glu Gly Gln Arg Met
        35                  40                  45

Ala Glu Met Leu Lys Ser Lys Ile
    50                  55
```

```
<210> SEQ ID NO 89
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 89

Gly Ser Phe Ser Tyr Val Thr Gly Leu Thr Ser Asp Asn Leu Lys Val
1               5                   10                  15

Pro Cys Gln Val Pro Ala Pro Glu Phe Phe Ser Trp Val Asp Gly Val
                20                  25                  30

Gln Ile His Arg Phe Ala Pro Val Pro Gly Pro Phe Phe Arg Asp Glu
            35                  40                  45

Val Thr Phe Thr Val Gly Leu Asn
        50                  55

<210> SEQ ID NO 90
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 90

Ser Leu Val Val Gly Ser Gln Leu Pro Cys Asp Pro Glu Pro Asp Thr
1               5                   10                  15

Glu Val Leu Ala Ser Met Leu Thr Asp Pro Ser His Ile Thr Ala Glu
                20                  25                  30

Thr Ala Ala Arg Arg Leu Ala Arg Gly Ser Pro Pro Ser Gln Ala Ser
            35                  40                  45

Ser Ser Ala Ser Gln Leu Ser Ala
        50                  55

<210> SEQ ID NO 91
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 91

Thr Gly Ala Leu Ile Thr Pro Cys Ser Ala Glu Glu Glu Lys Leu Pro
1               5                   10                  15

Ile Ser Pro Leu Ser Asn Ser Leu Leu Arg His His Asn Leu Val Tyr
                20                  25                  30

Ser Thr Ser Ser Arg Ser Ala Ser Gln Arg Gln Lys Lys Val Thr Phe
            35                  40                  45

Asp Arg Leu Gln Val Leu Asp Asp
        50                  55

<210> SEQ ID NO 92
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 92

Ala Leu Ile Thr Pro Cys Ala Ala Glu Glu Glu Lys Leu Pro Ile Ser
1               5                   10                  15
```

Pro Leu Ser Asn Ser Leu Leu Arg His His Asn Leu Val Tyr Ser Thr
                20                    25                    30

Ser Ser Arg Ser Ala Ala Gln Arg Gln Lys Lys Val Thr Phe Asp Arg
        35                    40                    45

Leu Gln Val Leu Asp Asp His Tyr
    50                    55

<210> SEQ ID NO 93
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 93

Ile Asn Pro Leu Ser Asn Ser Leu Met Arg Phe His Asn Lys Val Tyr
1               5                    10                    15

Ser Thr Thr Ser Arg Ser Ala Ser Leu Arg Ala Lys Lys Val Thr Phe
                20                    25                    30

Asp Arg Val Gln Val Leu Asp Ala His Tyr Asp Ser Val Leu Gln Asp
        35                    40                    45

Val Lys Arg Ala Ala Ser Lys Val
    50                    55

<210> SEQ ID NO 94
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 94

Asn Thr Thr Leu Lys Glu Ile Lys Glu Leu Ala Ser Gly Val Lys Ala
1               5                    10                    15

Glu Leu Leu Ser Val Glu Glu Ala Cys Arg Leu Val Pro Ser His Ser
                20                    25                    30

Ala Arg Ser Lys Phe Gly Tyr Gly Ala Lys Glu Val Arg Ser Leu Ser
        35                    40                    45

Ser Lys Ala Ile Asn His Ile Asn
    50                    55

<210> SEQ ID NO 95
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 95

Leu Val Pro Pro His Ser Ala Arg Ser Lys Phe Gly Tyr Ser Ala Lys
1               5                    10                    15

Asp Val Arg Ser Leu Ser Ser Lys Ala Ile Asn Gln Ile Arg Ser Val
                20                    25                    30

Trp Glu Asp Leu Leu Glu Asp Thr Thr Thr Pro Ile Pro Thr Thr Ile
        35                    40                    45

Met Ala Lys Asn Glu Val Phe Cys
    50                    55

<210> SEQ ID NO 96
<211> LENGTH: 56

<212> TYPE: PRT
<213> ORGANISM: Artificial Sequence
<220> FEATURE:
<223> OTHER INFORMATION: Synthetic peptide epitope

<400> SEQUENCE: 96

Ser Ala Arg Leu Leu Thr Val Glu Glu Ala Cys Ala Leu Thr Pro Pro
1               5                   10                  15

His Ser Ala Lys Ser Arg Tyr Gly Phe Gly Ala Lys Glu Val Arg Ser
            20                  25                  30

Leu Ser Arg Arg Ala Val Asn His Ile Arg Ser Val Trp Glu Asp Leu
        35                  40                  45

Leu Glu Asp Gln His Thr Pro Ile
    50                  55

<210> SEQ ID NO 97
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 97

Ser Ala Arg Leu Leu Thr Leu Glu Glu Ala Cys Gln Leu Thr Pro Pro
1               5                   10                  15

His Ser Ala Arg Ser Lys Tyr Gly Phe Gly Ala Lys Glu Val Arg Ser
            20                  25                  30

Leu Ser Gly Arg Ala Val Asn His Ile Lys Ser Val Trp Lys Asp Leu
        35                  40                  45

Leu Glu Asp Pro Gln Thr Pro Ile
    50                  55

<210> SEQ ID NO 98
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 98

Ile Arg Ser Val Trp Glu Asp Leu Leu Glu Asp Thr Thr Thr Pro Ile
1               5                   10                  15

Pro Thr Thr Ile Met Ala Lys Asn Glu Val Phe Cys Val Asp Pro Ala
            20                  25                  30

Lys Gly Gly Arg Lys Ala Ala Arg Leu Ile Val Tyr Pro Asp Leu Gly
        35                  40                  45

Val Arg Val Cys Glu Lys Arg Ala
    50                  55

<210> SEQ ID NO 99
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 99

Ile Arg Ser Val Trp Glu Asp Leu Leu Glu Asp Thr Thr Thr Pro Ile
1               5                   10                  15

Pro Thr Thr Ile Met Ala Lys Asn Glu Val Phe Cys Val Asp Pro Ala
            20                  25                  30

-continued

```
Lys Gly Gly Arg Lys Pro Ala Arg Leu Ile Val Tyr Pro Asp Leu Gly
        35                  40                  45

Val Arg Val Cys Glu Lys Arg Ala
    50                  55

<210> SEQ ID NO 100
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 100

Glu Val Arg Ser Leu Ser Arg Arg Ala Val Asn His Ile Arg Ser Val
1               5                   10                  15

Trp Glu Asp Leu Leu Glu Asp Gln His Thr Pro Ile Asp Thr Thr Ile
            20                  25                  30

Met Ala Lys Asn Glu Val Phe Cys Ile Asp Pro Thr Lys Gly Gly Lys
        35                  40                  45

Lys Pro Ala Arg Leu Ile Val Tyr
    50                  55

<210> SEQ ID NO 101
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 101

Tyr Asp Thr Arg Cys Phe Asp Ser Thr Val Thr Glu Arg Asp Ile Arg
1               5                   10                  15

Thr Glu Glu Ser Ile Tyr Gln Ala Cys Ser Leu Pro Gln Glu Ala Arg
            20                  25                  30

Thr Val Ile His Ser Leu Thr Glu Arg Leu Tyr Val Gly Gly Pro Met
        35                  40                  45

Thr Asn Ser Lys Gly Gln Ser Cys
    50                  55

<210> SEQ ID NO 102
<211> LENGTH: 56
<212> TYPE: PRT
<213> ORGANISM: Artificial Sequence
<220> FEATURE:
<223> OTHER INFORMATION: Synthetic peptide epitope

<400> SEQUENCE: 102

Cys Lys Ala Ala Gly Ile Ile Ala Pro Thr Met Leu Val Cys Gly Asp
1               5                   10                  15

Asp Leu Val Val Ile Ser Glu Ser Gln Gly Thr Glu Glu Asp Glu Arg
            20                  25                  30

Asn Leu Arg Ala Phe Thr Glu Ala Met Thr Arg Tyr Ser Ala Pro Pro
        35                  40                  45

Gly Asp Pro Pro Arg Pro Glu Tyr
    50                  55
```

VIRAL EXPOSURE SIGNATURE FOR DETECTION OF EARLY STAGE HEPATOCELLULAR CARCINOMA

CROSS REFERENCE TO RELATED APPLICATIONS

This application is the U.S. National Stage of International Application No. PCT/US2020/055077, filed Oct. 9, 2020, which was published in English under PCT Article 21(2), which claims the benefit of U.S. Provisional Application No. 62/914,138, filed Oct. 11, 2019, both herein incorporated by reference in their entireties.

ACKNOWLEDGMENT OF GOVERNMENT SUPPORT

This invention was made with government support under project number Z01-BC010313 awarded by the National Institutes of Health. The government has certain rights in the invention.

FIELD

This disclosure concerns a viral exposure signature and its use for identifying a subject with early stage (pre-symptomatic) hepatocellular carcinoma.

BACKGROUND

Hepatocellular carcinoma (HCC) is considered a virus-related malignancy in which hepatitis B and C viruses (HCV and HBV) are major etiological factors (Farazi et al., Nat Rev Cancer 2006; 6:674-687). Viral hepatitis causes inflammation and chronic liver diseases (CLD), which may lead to fibrosis, cirrhosis and eventually, HCC. While HBV or HCV chronic carriers have an increased risk of developing HCC, the risk varies among individuals and not all patients with liver disease develop liver cancer (Arzumanyan et al., Nat Rev Cancer 2013; 13:123-135). An effective strategy to prevent HCC is to eliminate causative factors. However, while direct-acting antiviral (DDA) treatment is remarkably effective in eliminating HCV infection, it reduces but does not completely eliminate HCC risk (Janjua et al., J Hepatol 2017; 66:504-513; Carrat et al., Lancet 2019; 393:1453-1464). Similarly, HBV vaccination, introduced in the early 80s, has been successful in significantly reducing HBV carriers but only modestly reduces HCC burden in HBV-prevalent areas (Chang et al., Gastroenterology 2016; 151:472-480). It is puzzling that the control of HBV infection in HBV-prevalent areas as well as HCV infection has been remarkably successful for decades, while the global HCC incidence and mortality rate has continued to increase since the 1990s (Liu et al., J Hepatol 2019; 70:674-683). Changing trends of etiological factors such as alcohol and non-alcohol/non-viral related liver diseases may contribute to the observed increase. Thus, in addition to cancer prevention, early detection is a key research area to stop HCC-inflicted mortality. Currently, medical guidelines recommend biannual surveillance using ultrasound with or without alpha-fetoprotein (AFP) for individuals with chronic liver disease such as cirrhosis (Sherman et al., Hepatology 2012; 56:793-796). However, these practices have yielded mix results as to whether it is effective in detecting HCC at an early stage and can provide survival benefit (Tzartzeva et al., Gastroenterology 2018; 154:1706-1718; Moon et al., Gastroenterology 2018; 155:1128-1139; Sherman et al., Hepatology 1995; 22:432-438). Noticeably, a majority of HCC patients are still diagnosed at an advanced stage, which precludes their chance to receive potentially curative therapies, and consequently leads to poor survival. Thus, there is an unmet need to implement an effective biomarker-guided surveillance program for early cancer detection.

SUMMARY

Described herein is a viral exposure signature (VES) that can be used to identify a subject with early stage HCC, particularly pre-symptomatic HCC. The VES is based on the presence or absence of antibodies to specific viral strains in a subject. Detection of the VES in a subject can be used, for example, to guide treatment and disease monitoring decisions.

Provided herein are methods of identifying a subject with early stage HCC. In some embodiments, the method includes detecting the presence or absence of antibodies to a plurality of viruses in a sample obtained from the subject; determining the presence of a viral exposure signature (VES) in the sample obtained from the subject; and identifying the subject as being at risk for developing HCC when the VES is present. In some embodiments, the plurality of viruses comprises at least 10, at least 20, at least 30, at least 40, at least 50 or at least 60 of the viruses listed in Table 5A. In some examples, the plurality of viruses comprises or consists of the 61 viruses listed in Table 5A or the 31 viruses listed in Table 6.

In some embodiments, the presence of the VES is determined by identifying antibodies to one or more of hepatitis C virus (HCV) genotype 3b, isolate Tr-Kj; HCV genotype 1b, isolate Taiwan; HCV genotype 1a, isolate 1; human cytomegalovirus, strain AD169; HCV genotype 6g, isolate JK046; HCV genotype 1b, isolate BK; HCV genotype 1c, isolate HC-G9; HCV genotype 1b, strain HC-J4; HCV genotype 4a, isolate ED43; hepatitis delta virus; HCV genotype 5a, isolate EUH1480; human cytomegalovirus; Crimean-Congo hemorrhagic fever virus, strain Nigeria/IbAr10200/1970; HCV genotype 1b, isolate HC-J1; influenza A virus, strain A/USSR/90/1977 H1N1; influenza A virus, strain A/Bangkok/1/1979 H3N2; HCV genotype 1c, isolate India; and Chapare virus, isolate Human/Bolivia/810419/2003.

In some embodiments, the presence of the VES is determined by not detecting antibodies to one or more of Epstein-Barr virus, strain B95-8; human rhinovirus 23; HCMV, strain Towne; human herpesvirus 2 (HHV-2), strain HG52; human herpesvirus 3; varicella-zoster virus, strain Dumas; Cercopithecine herpesvirus 16; human adenovirus C serotype 2; human astrovirus-1; human respiratory syncytial virus; human herpesvirus 6B, strain Z29; human herpesvirus 7, strain JI; human rhinovirus 14; Lordsdale virus, strain GII/Human/United Kingdom/Lordsdale/1993; human herpesvirus 1, strain KOS; human metapneumovirus, strain CAN97-83; coxsackievirus A16, strain G-10; Epstein-Barr virus, strain AG876; cowpox virus; human herpesvirus 1, strain 17; human adenovirus E serotype 4; human adenovirus F serotype 40; tanapox virus; human adenovirus C serotype 5; rhinovirus B; human herpesvirus 8; human herpesvirus 6A, strain Uganda-1102; human rhinovirus A serotype 89, strain 41467-Gallo; norovirus MD145, isolate GII/Human/United States/MD145-12/1987; molluscum contagiosum virus subtype 1; vaccinia virus, strain Copenhagen; poliovirus type 1, strain Sabin; orf virus; HHV-2, strain 333; hepatitis B virus; Epstein-Barr virus, strain GD1; human parainfluenza 3 virus, strain Wash/47885/57; HHV-2;

human enterovirus 71, strain BrCr; human herpesvirus 6A, strain GS; Cercopithecine herpesvirus 1; influenza B virus, strain B/Yamagata/16/1988; and influenza A virus, strain A/Philippines/2/1982 H3N2.

In other embodiments, the method of identifying a subject with early stage HCC includes (i) detecting the presence or absence of antibodies specific for a plurality of viruses in a sample obtained from the subject, wherein the plurality of viruses comprises hepatitis C virus (HCV) genotype 3b, isolate Tr-Kj; HCV genotype 1b, isolate Taiwan; HCV genotype 1a, isolate 1; human cytomegalovirus (HCMV) strain AD169; HCV genotype 6g, isolate JK046; Epstein-Barr virus (EBV), strain B95-8; human rhinovirus 23; HCMV strain Towne; HCV genotype 1b, isolate BK; and human herpesvirus 2 (HHV-2), strain HG52; and (ii) identifying the subject as being at risk for developing HCC if: (a) antibodies specific for HCV genotype 3b, isolate Tr-Kj; HCV genotype 1b, isolate Taiwan; HCV genotype 1a, isolate 1; HCMV strain AD169; HCV genotype 6g, isolate JK046; and/or HCV genotype 1b, isolate BK, are detected in the sample; and/or (b) antibodies specific for EBV, strain B95-8; human rhinovirus 23; HCMV strain Towne; and/or HHV-2, strain HG52, are not detected in the sample.

In some embodiments, the sample is a blood or serum sample.

In some embodiments, the antibodies are detected by phage immunoprecipitation, immunoblot or enzyme-linked immunosorbent assay.

In some embodiments, the method further includes administering an appropriate therapy or providing an appropriate procedure (such as surgery) for the treatment of HCC. In some examples, the method further includes performing a liver transplant in the subject with early stage HCC. In other examples, the method further includes liver resection of the subject with early stage HCC, with or without radiofrequency ablation (RFA). In some examples, if the subject is also positive for HBV or HCV, the subject is administered an anti-viral drug.

In some embodiments, the method further includes active diagnostic monitoring of the subject with early stage HCC. For example, the subject can be monitored on a regular schedule, such as every 3 months or every 6 months, using ultrasound, contrast enhanced computerized tomography (CT) and/or magnetic resonance imaging (MRI).

Also provided is a phage display library expressing unique peptide epitopes from each of the viruses listed in Table 5A or Table 6. In some embodiments, the phage display library expresses the peptides of SEQ ID NOs: 1-61, or a subset thereof. In some examples, the phage display library expresses the peptides of SEQ ID NOs: 1-102, or a subset thereof. In other examples, the phage display library expresses the peptides of SEQ ID NOs: 62-102, or a subset thereof.

Further provided is an array comprising unique peptide epitopes from each of the viruses listed in Table 5A or Table 6. In some examples the unique peptide epitopes comprise the peptides of SEQ ID NOs: 1-61 (shown in Table 5B), the peptides of SEQ ID NOs: 62-102 (shown in Table 3B), or the peptides of SEQ ID NOs: 1-102.

The foregoing and other objects and features of the disclosure will become more apparent from the following detailed description, which proceeds with reference to the accompanying figures.

BRIEF DESCRIPTION OF THE DRAWINGS

(FIG. 1A) Schema of screening of NCI-UMD cohort including 899 serum samples by VirScan and 849 matching buffy coat or cheek swab samples by genome-wide association study (GWAS), with integrated analysis among population groups: population controls (PC, n=412), high risk chronic liver disease cases (HR, n=337), and hepatocellular carcinoma cases (HCC, n=150); the VES is validated in a perspective NIDDK cohort with NIDDK-HR (n=129) and NIDDK-HCC (n=44). (FIG. 1B) Histogram showing the sequencing reads of VirScan with the mean coverage accuracy of 0.93. (FIG. 1C) Rarefaction plot showing the viral species richness detected in PC, HR and HCC groups. (FIG. 1D) Raincloud plot showing the viral species in each individual across populations. From left to right, each integrated boxplot illustrates: minimum, the first quantile, mean, the third quantile, and maximum, respectively. (FIG. 1E) Left: Bar plot showing the percentage of the prevalent viral infection among all samples. Right: Dot plot showing the number of the corresponding unique epitopes in each sample. Each dot represents the unique epitope number of one individual. The blue bars on the dot plot represent the mean.

(FIG. 2A) Contingency matrices comparing HCV, HBV, and HIV detection with VirScan against viral detection laboratory tests reported in the patient medical charts. For the purpose of computing binary classification test statistics, clinical results were considered true values and VirScan results were considered predicted values. (FIG. 2B) Left: Heatmap showing HCV proteomic enrichment among PC, HR and HCC groups. Each row represents the significant peptide tiling. Each column is a sample. The colored bar on the left of the panel indicates proteomic location of the tiling peptides (green). The first colored bar at the top of the panel indicates the groups of the samples among PC, HR, and HCC groups. The second bar at the top is HCV species positive (HCV species+) based on VirScan data. The intensity of each cell corresponds to the scaled −log 10 (p-value) measure of significance of enrichment for a peptide in a sample (greater values indicate stronger antibody response). Right: Bar plot showing the B-cell epitope prediction score for each peptide. (FIG. 2C) Bar chart representing the coinfection viral status in HIV positive (HIV +) versus HIV negative (HIV −) cases. Asterisks denote the false discovery rate less than 0.05.

(FIG. 3A) VES are identified using Xgboost machine learning method. Flow chart showing training set and 10× cross validation sets to compare the viral profiles in HCC versus PC. The scored results are shown the predictive VES score of each sample among PC, HR and HCC. (FIG. 3B) Gradient boosting plot showing the area under the curve (AUC) value of training sets and 10× cross validation sets. The vertical line represents gradient boosting stops at round 108th testing to avoid overfitting. (FIG. 3C) Bar plot showing the 61-VES identified by comparing HCC with PC using Xgboost in NCI-UMD cohort. (FIG. 3D) Violin plot showing the predictive VES score among PC, HR and HCC groups. (**** P<0.0001, two-tailed p-value in Mann Whitney test). (FIGS. 3E-3F) Phylogenetic analysis of the 61 viral strains, which results in eight well-defined branches.

(FIG. 4A) Estimate of receiver operating characteristic curves (ROC) of NCI-UMD cohort at HCC diagnosis. Plots display AUC estimation for 61-VES at HCC diagnosis (PC, n=412; HR, n=337; HCC, n=150). (FIG. 4B) VES levels are listed as below, low and high of NCI-UMD cohort. The dashed line indicates less than 0.5 is below VES level. Low and high VES levels are defined by more than 0.5 VES level (median of more than 0.5 feature level as a separation). (FIG. 4C) Kaplan Meier (KM) plot survival curve for the NCI-UMD cohort with either 61-VES. (FIGS. 4D, 4E) Estimate of receiver operating characteristic curves (ROC) in predicting NIDDK validation cohort at HCC diagnosis and baseline. Plots display area under the curve estimation for 61-VES and clinical variable AFP at HCC diagnosis (NIDDK-HR2, n=106; NIDDK-HCC, n=44) and at baseline (NIDDK-HR1, n=129; NIDDK-HCC, n=44). (FIG. 4F) Time-dependent AUC showing the landmark time points performance of VES from 1 to 10 years relative to baseline. (FIG. 4G) The boxplots show the relationships between 61-VES and the clinical diagnosis in the NIDDK validation cohort at different follow-up (F/U) time points. (FIG. 4H) AUC values corresponding to predictions based on clinical indicators from patient charts compared with those based on VES, as well as those based on the combination clinical and VES for NIDDK cohort at baseline.

(FIG. 5A) Distribution of reproducibility threshold –log 10 (p-values) is shown. Histogram of the frequency of the reproducibility threshold –log 10 (p-values). The mode of the distribution is approximately 2.358. (FIG. 5B) Examples of the experimental repeats in VirScan showing the background signals of the blank PBS samples at the bottom and the hits with significant –log 10 (P-value) more than 2.358 of serum samples (top panel). (FIG. 5C) Pie charts showing the DNA and RNA viral compositions before and after immunoprecipitation in VirScan, as library input and Phage-IP, respectively. (FIG. 5D) Stacked bar plot showing phylogenetic composition of common viral taxa (0.1% abundance) at the viral family level among PC, HR and HCC. (FIG. 5E) The diagram includes detailed information on the excluded participants from initial enrollment, sample allocation with indicated criteria, QC and final data analysis.

(FIG. 6A) Heatmap showing the hierarchical clustering (hCluster) of the samples among PC, HR and HCC with the differential viral features. The listed 17 viruses exhibit a fold change greater than 2 with FDR<0.05 in PC and HCC ANOVA test. Bottom bar shows the scaled density signal. (FIG. 6B) Histogram showing the most differential viral species (sp) and strains in HCC versus PC.

(FIG. 7A) QQ-plot for all 729,000 variants represented in the GWAS. (FIG. 7B) Principal component analysis (PCA) of all samples after quality control (QC) in different racial groups. (FIG. 7C) SNP rs12979860 was significantly associated with epitopes in Core and NS5B regions of HCV. Left panel: Heatmap showing the significance of SNP associated with 375 epitopes abundances of HCV genotype 2 and 3. Core and NS5B regions were highly associated with the genotypes. Right panel: Boxplots represent the difference of the epitope abundance between the genotypes in the Core region and NS5B region.

FIGS. 8A-8E: CONSORT flow diagrams for NIDDK cohort and assessment of the association of clinical outcomes with VES in NIDDK Cohort. (FIG. 8A) The diagram includes detailed information on the excluded participants from initial enrollment, sample allocation with indicated criteria, follow-up, QC and final data analysis. (FIG. 8B) Kaplan-Meier survival curves for NIDDK cohorts grouped by VES level. (FIG. 8C) Time-dependent ROC curve analysis of VES performance for landmark time points 1-10 years relative to baseline. (FIG. 8D) AUC prediction performance based on univariate and multivariate clinical indicators compared to VES (vertical band) for the NIDDK cohort at diagnosis. (FIG. 8E) AUC prediction performance based on univariate and multivariate clinical indicators compared to VES (vertical band) for the NCI-UMD cohort.

(FIG. 9A) Manhattan plot showing the detected genetic variants from GWAS associated with the viral featural phenotype of NCI-UMD cohort. Annotated names of gene loci with P-value less than $10^{-7}$. (FIG. 9B) Locus Zoom plot showing the LD structure of one of the lead SNPs, rs16960234, around the region of CDH13 and RP11-543N12.1. (FIG. 9C) Heatmap showing the high linkage disequilibrium (LD) SNPs of rs16960234 from 1000 Genomes database (R2>0.6). The density of the heatmap indicates the r2 value of the correlation. The labeled SNPs are the ones with eQTL available. (FIG. 9D) The eQTL of CDH13 in tissue artery tibial across genotypes of SNP rs1690234 from GTEx database. (FIG. 9E) The genotypic odds ratios (OR) of rs1690234 among HR and HCC relative to PC. (FIGS. 9F, 9G) VES score fold changes (FD) in genotypes AA, AG and GG of rs1690234 based on 61-VES and 31-VES among HCC relative to PC.

(FIG. 11A) XGBoost performance evaluated by AUC on HCC versus AR with 10× cross-validation. (FIG. 11B) ROC curves for PC versus HCC prediction, as well as for AR versus HCC prediction, using features from HCC versus AR predication. (FIG. 11C) Features selected by HCC versus AR predication was highly overlapped with VES signature. (FIG. 11D) XGBoost performance evaluated by AUC on HCC versus PC with 60/40 train-test split. (FIG. 11E) ROC curves showed the train and test datasets performance. (FIG. 11F) 1000 permutation with the 60/40 train-test split. (FIGS. 11G-11J) The selected features and feature importance after 1000 permutation test.

SEQUENCE LISTING

Figure 1A:
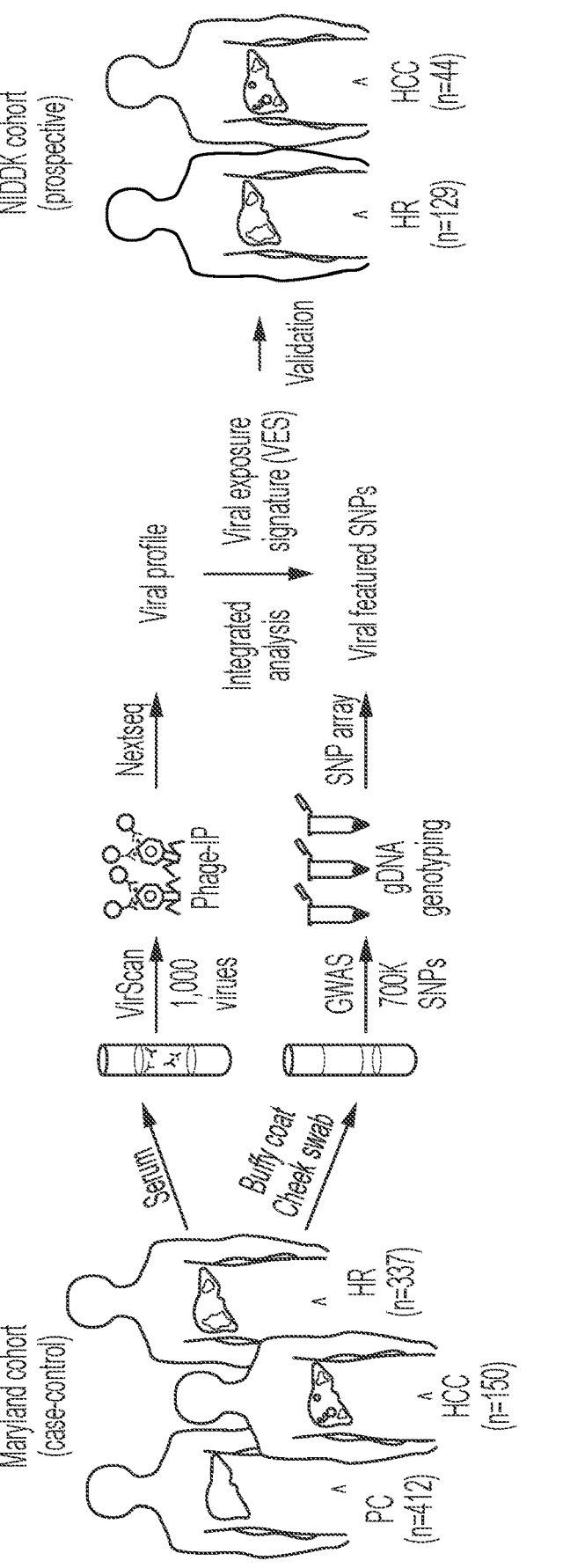
FIGS. 1A-1E: Viral richness and frequency of infection spectrum in serum.

The amino acid sequences listed in the accompanying sequence listing are shown using standard three letter code for amino acids, as defined in 37 C.F.R. 1.822. The Sequence Listing is submitted as an ASCII text file, created on Mar. 14, 2022, 58.4 KB, which is incorporated by reference herein. In the accompanying sequence listing:

SEQ ID NOs: 1-102 are amino acid sequences of unique peptide epitopes from human viruses.

DETAILED DESCRIPTION

I. Terms and Methods

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of*

*Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics*, 2nd Edition, 2003 (ISBN: 0-471-26821-6).

The singular forms "a," "an," and "the" refer to one or more than one, unless the context clearly dictates otherwise. For example, the term "comprising a probe" includes single or plural probes and is considered equivalent to the phrase "comprising at least one probe." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank® Accession numbers (for the sequence present on Feb. 8, 2016). In case of conflict, the present specification, including explanations of terms, will control. In addition, the materials, methods, and examples are illustrative only and not intended to be limiting.

Except as otherwise noted, the methods and techniques of the present disclosure are generally performed according to conventional methods well known in the art and as described in various general and more specific references that are cited and discussed throughout the present specification. See, e.g., Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

In order to facilitate review of the various embodiments of the disclosure, the following explanations of specific terms are provided:

Administration: The introduction of an agent, such as an anti-viral therapeutic, into a subject by a chosen route. Administration can be local or systemic. For example, if the chosen route is intravascular, the agent is administered by introducing the composition into a blood vessel of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Antibody: A polypeptide ligand comprising at least one variable region that recognizes and binds (such as specifically recognizes and specifically binds) an epitope of an antigen, such as a viral antigen. Mammalian immunoglobulin molecules are composed of a heavy (H) chain and a light (L) chain, each of which has a variable region, termed the variable heavy ($V_H$) region and the variable light ($V_L$) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE. Antibody isotypes not found in mammals include IgX, IgY, IgW and IgNAR. IgY is the primary antibody produced by birds and reptiles, and has some functionally similar to mammalian IgG and IgE. IgW and IgNAR antibodies are produced by cartilaginous fish, while IgX antibodies are found in amphibians.

Array: An arrangement of molecules, such as biological macromolecules (such as peptides or nucleic acid molecules) or biological samples (such as tissue sections), in addressable locations on or in a substrate. In some embodiments herein, the array comprises at least 10, at least 20, at least 30, at least 40, at least 50, at least 60 (such as 61) addressable locations. In particular examples, the array comprises peptide epitopes from each of the viruses listed in Table 5A or Table 6.

Control: A "control" refers to a sample or standard used for comparison with an experimental sample, such as a serum sample obtained from a subject suspected of having or at risk for HCC. In some embodiments, the control is a sample obtained from a healthy patient (e.g., one not having HCC or cirrhosis). In some embodiments, the control is a historical control or standard reference value or range of values (e.g., a previously tested control sample, such as a group of samples that represent baseline or normal values).

Diagnosis: The process of identifying a disease by its signs, symptoms and results of various tests. The conclusion reached through that process is also called "a diagnosis." Forms of testing commonly performed include blood tests, medical imaging, and biopsy.

Early stage: In the context of the present disclosure, detecting "early stage" HCC refers to identifying HCC in a subject prior to the onset of symptoms and/or prior to standard clinical diagnosis. "Early stage" in this context is not synonymous with stage 0 or stage I cancer. In some embodiments, early stage HCC is characterized by the presence of a single lesion less than 3 cm in diameter (such as 0.1 to 2.9 cm in diameter, such as 0.5 to 2.5 cm, 0.5 to 1 cm or 1 to 2.9 cm in dimeter) without detectable local or distant metastatic lesions (such as detectable by CT or MRI).

Epitope: An antigenic determinant. These are particular chemical groups or peptide sequences on a molecule that are antigenic, i.e. that elicit a specific immune response. An antibody specifically binds a particular antigenic epitope on a polypeptide, such as a viral polypeptide.

Hepatocellular carcinoma (HCC): A primary malignancy of the liver, which in some cases occurs in patients with inflammatory livers resulting from viral hepatitis, liver toxins or hepatic cirrhosis (often caused by alcoholism). Exemplary therapies for HCC include but are not limited to, one or more of surgery, transarterial chemoembolization (TACE), ablative therapies (including both thermal and cryoablation), radio embolization, and percutaneous alcohol injection.

Isolated: An "isolated" biological component (such as a nucleic acid molecule, protein, or cell) has been substantially separated or purified away from other biological components, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

Sample (or biological sample): A biological specimen containing genomic DNA, RNA (including mRNA), protein (such as antibodies), or combinations thereof, obtained from a subject. Examples include, but are not limited to, peripheral blood, plasma, urine, saliva, tissue biopsy, fine needle aspirate, punch biopsy surgical specimen, and autopsy material. In specific embodiments herein, the sample is a blood or serum sample.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Subject: Living multi-cellular vertebrate organisms, a category that includes human and non-human mammals. In some examples herein, the subject is suspected of having or at risk for having HCC.

Tumor: All neoplastic cell growth and proliferation, whether malignant or benign, and all pre-cancerous and cancerous cells and tissues. In some examples, the tumor is a HCC tumor.

II. Viral Exposure Signature and Methods of Use

Viruses are known to affect human health by altering host immunity, which makes the interplay between the virome and the host crucial in the pathogenesis of human chronic diseases, including cancer (Foxman et al., Nat Rev Microbiol 2011; 9:254-64; Cadwell, Immunity 2015; 42:805-813). Diverse pathogenic and non-pathogenic viruses may interact with one another as well as their host to shape host immunity, which may alter its response to new infections. Consequently, viruses that persist or are cleared in the host may leave unique molecular footprints that can alter disease susceptibility to cancer and may serve as an excellent window of early onset disease (Cadwell, Immunity 2015; 42:805-813). It was hypothesized that unique post-viral exposure signatures resulting from virus-host interactions could reflect a cascade of events that may alter the risk of developing HCC. Such signatures could serve as early detection biomarkers and offer knowledge about potentially modifiable factors for early onset HCC. In the study disclosed herein, serological samples from 899 individuals enrolled in a case-control study of liver cancer (NCT00913757; clinicaltrials.gov) were profiled using a synthetic virome technology, VirScan, based on a high-throughput sequencing method, to detect exposure history to all known human viruses (Xu et al., Science 2015; 348: aaa0698). A unique viral exposure signature (VES) that can discriminate HCC cases from CLD and healthy volunteers matched by age and sex is disclosed herein. The VES was validated in a prospective National Institute of Diabetes and Digestive and Kidney Diseases (NIDDK) at-risk cohort for HCC.

Provided herein are methods of identifying a subject as being at risk for developing HCC. In some embodiments, the method includes detecting the presence or absence of antibodies to a plurality of viruses in a sample obtained from the subject; determining the presence of a viral exposure signature (VES) in the sample obtained from the subject; and identifying the subject as being at risk for developing HCC when the VES is present.

In some embodiments, the presence of the VES is determined by identifying antibodies to one or more of hepatitis C virus (HCV) genotype 3b, isolate Tr-Kj; HCV genotype 1b, isolate Taiwan; HCV genotype 1a, isolate 1; human cytomegalovirus, strain AD169; HCV genotype 6g, isolate JK046; HCV genotype 1b, isolate BK; HCV genotype 1c, isolate HC-G9; HCV genotype 1b, strain HC-J4; HCV genotype 4a, isolate ED43; hepatitis delta virus; HCV genotype 5a, isolate EUH1480; human cytomegalovirus; Crimean-Congo hemorrhagic fever virus, strain Nigeria/IbAr10200/1970; HCV genotype 1b, isolate HC-J1; influenza A virus, strain A/USSR/90/1977 H1N1; influenza A virus, strain A/Bangkok/1/1979 H3N2; HCV genotype 1c, isolate India; and Chapare virus, isolate Human/Bolivia/810419/2003.

In some embodiments, the presence of the VES is determined by not detecting antibodies to one or more of Epstein-Barr virus, strain B95-8; human rhinovirus 23; HCMV, strain Towne; human herpesvirus 2 (HHV-2), strain HG52; human herpesvirus 3; varicella-zoster virus, strain Dumas; Cercopithecine herpesvirus 16; human adenovirus C serotype 2; human astrovirus-1; human respiratory syncytial virus; human herpesvirus 6B, strain Z29; human herpesvirus 7, strain JI; human rhinovirus 14; Lordsdale virus, strain GII/Human/United Kingdom/Lordsdale/1993; human herpesvirus 1, strain KOS; human metapneumovirus, strain CAN97-83; coxsackievirus A16, strain G-10; Epstein-Barr virus, strain AG876; cowpox virus; human herpesvirus 1, strain 17; human adenovirus E serotype 4; human adenovirus F serotype 40; tanapox virus; human adenovirus C serotype 5; rhinovirus B; human herpesvirus 8; human herpesvirus 6A, strain Uganda-1102; human rhinovirus A serotype 89, strain 41467-Gallo; norovirus MD145, isolate GII/Human/United States/MD145-12/1987; molluscum contagiosum virus subtype 1; vaccinia virus, strain Copenhagen; poliovirus type 1, strain Sabin; orf virus; HHV-2, strain 333; hepatitis B virus; Epstein-Barr virus, strain GD1; human parainfluenza 3 virus, strain Wash/47885/57; HHV-2; human enterovirus 71, strain BrCr; human herpesvirus 6A, strain GS; Cercopithecine herpesvirus 1; influenza B virus, strain B/Yamagata/16/1988; and influenza A virus, strain A/Philippines/2/1982 H3N2.

In some embodiments, the plurality of viruses includes at least 10, at least 20, at least 30, at least 40, at least 50 or at least 60 of the viruses listed in Table 5A. In some examples, the plurality of viruses comprises or consists of the 61 viruses listed in Table 5A. In some examples, the plurality of viruses comprises or consists of the 31 viruses listed in Table 6.

In particular embodiments, step (ii) includes determining the presence of the VES in the sample obtained from the subject if (a) antibodies specific for three or more, four or more, five or more, six or more, or seven or more of hepatitis C virus (HCV) genotype 3b, isolate Tr-Kj; HCV genotype 1b, isolate Taiwan; HCV genotype 1a, isolate 1; human cytomegalovirus, strain AD169; HCV genotype 6g, isolate JK046; HCV genotype 1b, isolate BK; HCV genotype 1c, isolate HC-G9; HCV genotype 1b, strain HC-J4; HCV genotype 4a, isolate ED43; hepatitis delta virus; HCV genotype 5a, isolate EUH1480; human cytomegalovirus; Crimean-Congo hemorrhagic fever virus, strain Nigeria/IbAr10200/1970; HCV genotype 1b, isolate HC-J1; influenza A virus, strain A/USSR/90/1977 H1N1; influenza A virus, strain A/Bangkok/1/1979 H3N2; HCV genotype 1c, isolate India; and Chapare virus, isolate Human/Bolivia/810419/2003 are detected in the sample; and/or (b) antibodies specific for three or more, four or more, five or more, six or more, or seven or more of Epstein-Barr virus, strain B95-8; human rhinovirus 23; HCMV, strain Towne; human herpesvirus 2 (HHV-2), strain HG52; human herpesvirus 3; varicella-zoster virus, strain Dumas; Cercopithecine herpesvirus 16; human adenovirus C serotype 2; human astrovirus-1; human respiratory syncytial virus; human herpesvirus 6B, strain Z29; human herpesvirus 7, strain JI; human rhinovirus 14; Lordsdale virus, strain GII/Human/United Kingdom/Lordsdale/1993; human herpesvirus 1, strain KOS; human metapneumovirus, strain CAN97-83; coxsackievirus A16, strain G-10; Epstein-Barr virus, strain AG876; cowpox virus; human herpesvirus 1, strain 17; human adenovirus E serotype 4; human adenovirus F serotype 40; tanapox virus; human adenovirus C serotype 5; rhinovirus B; human herpesvirus 8; human herpesvirus 6A, strain Uganda-1102; human rhinovirus A serotype 89, strain 41467-Gallo; norovirus MD145, isolate GII/Human/United States/MD145-12/1987; molluscum contagiosum virus subtype 1; vaccinia virus, strain Copenhagen; poliovirus type 1, strain Sabin; orf virus; HHV-2, strain 333; hepatitis B virus; Epstein-Barr virus, strain GD1; human parainfluenza 3 virus, strain Wash/47885/57; HHV-2; human enterovirus 71, strain BrCr; human herpesvirus 6A, strain GS; Cercopithecine herpesvirus 1; influenza B virus, strain B/Yamagata/16/1988; and influenza A virus, strain A/Philippines/2/1982 H3N2 are not detected in the sample.

In some embodiments, the sample is a blood or serum sample. In some examples, the method further includes obtaining the biological sample from the subject. In some examples, the subject is a human subject.

The presence of antibodies can be detected using any immunoassay. In some embodiments, the antibodies are detected by phage immunoprecipitation, immunoblot or enzyme-linked immunosorbent assay.

Also provided is a phage display library expressing unique peptide epitopes from each of the viruses listed in Table 5A or Table 6. The phage display library can be used to determine the presence of the VES. In some embodiments, the phage display library expresses the peptides of SEQ ID NOs: 1-61 (see Table 5B). In other examples, the phage display library expresses the peptides of SEQ ID NOs: 62-102 (see Table 3B). In some examples, the phage display library expresses the peptides of SEQ ID NOs: 1-102. In some examples, the phage display library expresses peptides at least 90%, at least 95%, at least 96%, at least 97%, at least 98%, at least 99% or 100% identical to any of SEQ ID NOs: 1-61, SEQ ID NOs: 62-102 and SEQ ID NOs: 1-102.

Further provided is an array including unique peptide epitopes from each of the viruses listed in Table 5A or Table 6. The array can be used to determine the presence of the VES. In some examples the unique peptide epitopes comprise the peptides of SEQ ID NOs: 1-61 (shown in Table 5B), the peptides of SEQ ID NOs: 62-102 (shown in Table 3B), or the peptides of SEQ ID NOs: 1-102. In some examples, the peptides have amino acid sequences at least 90%, at least 95%, at least 96%, at least 97%, at least 98%, at least 99% or 100% identical to any of SEQ ID NOs: 1-61, SEQ ID NOs: 62-102 and SEQ ID NOs: 1-102.

In other embodiments provided herein, the method of identifying a subject as being at risk for developing HCC includes (i) detecting the presence or absence of antibodies specific for a plurality of viruses in a sample obtained from the subject, wherein the plurality of viruses includes hepatitis C virus (HCV) genotype 3b, isolate Tr-Kj; HCV genotype 1b, isolate Taiwan; HCV genotype 1a, isolate 1; human cytomegalovirus (HCMV) strain AD169; HCV genotype 6g, isolate JK046; Epstein-Barr virus (EBV), strain B95-8; human rhinovirus 23; HCMV strain Towne; HCV genotype 1b, isolate BK; and human herpesvirus 2 (HHV-2), strain HG52; and (ii) identifying the subject as being at risk for developing HCC if: (a) antibodies specific for HCV genotype 3b, isolate Tr-Kj; HCV genotype 1b, isolate Taiwan; HCV genotype 1a, isolate 1; HCMV strain AD169; HCV genotype 6g, isolate JK046; and/or HCV genotype 1b, isolate BK, are detected in the sample; and/or (b) antibodies specific for EBV, strain B95-8; human rhinovirus 23; HCMV strain Towne; and/or HHV-2, strain HG52, are not detected in the sample.

In some examples, step (ii) includes identifying the subject as being at risk for developing HCC if (a) antibodies specific for at least two, at least three, at least four, at least five or all six of HCV genotype 3b, isolate Tr-Kj; HCV genotype 1b, isolate Taiwan; HCV genotype 1a, isolate 1; HCMV strain AD169; HCV genotype 6g, isolate JK046; and HCV genotype 1b, isolate BK, are detected in the sample; and/or (b) antibodies specific for at least one, at least two, at least three or all four of EBV strain B95-8; human rhinovirus 23; HCMV strain Towne; and/or HHV-2 strain HG52, are not detected in the sample.

In some examples, the sample is a blood or serum sample. In specific examples, the method further includes obtaining the biological sample from the subject.

In some examples, the antibodies are detected by phage immunoprecipitation, immunoblot or enzyme-linked immunosorbent assay.

In some embodiments of the disclosed methods, the method further includes treating a subject with an appropriate therapy to aid in the prevention or treatment of HCC. In some examples, the appropriate therapy includes vaccination against hepatitis B virus (HBV) (such as administration of Engerix-B®, Recombivax HB®, or Heplisav-B®), antiviral treatment against HBV (such as administration of PEG-IFN, entecavir, tenofovir, lamivudine, adefovir, and/or telbivudine) and/or anti-viral treatment against HCV (such as administration of one or more of glecaprevir, sofobuvir, daclatasvir, grazoprevir, and ombitasvir). Anti-viral drugs include, for example, nucleoside/nucleotide analogs (e.g., entecavir and tenofovir disoproxil fumarate), interferon, and lamivudine. In some examples, the method further includes performing a liver transplant in the subject with early stage HCC. In other examples, the method further includes liver resection of the subject with early stage HCC, with or without radiofrequency ablation (RFA).

In some embodiments, the method further includes active diagnostic monitoring of the subject with early stage HCC. For example, the subject can be monitored on a regular schedule, such as every 2 months, every 3 months, every 4 months, every 5 months or every 6 months, using ultrasound, contrast enhanced computerized tomography (CT) and/or magnetic resonance imaging (MRI).

In some examples, the additional treatment includes lifestyle or diet changes, including programs to reduce intravenous drug use, needle exchange programs, prevention of sexually-transmitted diseases, reducing or eliminating alcohol consumption, reducing obesity-related inflammation (such as by improving diet and increasing exercise), improving insulin resistance, increasing consumption of vegetables, consuming branched-chain amino acids and/or taking vitamin D. For some patients, such as those with hereditary hemochromatosis, iron overload can increase the risk of developing HCC. Thus, in some examples, the appropriate therapy includes treating iron overload. Aflatoxin B1, a known carcinogen produced by fungi of the *Aspergillus* species, is commonly found as a contaminate of grains, nuts, and vegetables in regions such as Asia and Africa. Thus, reducing aflatoxin exposure can also be used to prevent or treat HCC. Additional preventative therapies and treatments are described in Schutte et al., *Gastrointest Tumors* 3(1): 37-43, 2016 and Schutte et al., *Gastrointest Tumors* 2(4): 188-194, 2016.

III. Phage Immunoprecipitation Sequencing

In some embodiments of the present disclosure, the methods of detecting the presence or absence of specific antibodies in patient samples, and thereby determining the presence of the VES, can be performed using phage immunoprecipitation sequencing (PhIP-Seq). This method is a high-throughput method that allows for a comprehensive analysis of a subject's antibody repertoire (see U.S. Publication No. 2016/0320406; Larman et al., *Nat. Biotechnol* 29: 535-541, 2011; and Mohan et al., *Nat Protoc* 13:1958-1978, 2018; each of which is incorporated by reference herein).

PhIP-Seq is one method that can be used to rapidly detect the presence or absence of a plurality of virus-specific antibodies in a patient sample. Briefly, this method includes designing a peptide library that is representative of the viruses that are to be detected. In context of the present disclosure, the library includes, for example, the 61 or 31 unique peptide epitopes of the 61-VES or 31-VES, respectively (see Tables 5A and 6). An oligonucleotide library encoding the peptides is constructed and PCR-amplified with adapters for cloning into a selected phage display vector to produce the phage display library. A patient sample, such as a blood or serum sample, is contacted with the phage display library to allow for phage-antibody complex formation and subsequent immunoprecipitation. The library of peptide-encoding oligonucleotide sequences is amplified by PCR directly from the immunoprecipitate, bar-coded and subjected to deep sequencing. Additional details of this method can be found in U.S. Publication No. 2016/0320406; Larman et al. (*Nat. Biotechnol* 29: 535-541, 2011), Mohan et al. (*Nat Protoc* 13:1958-1978, 2018), and the Novagen T7Select System Manual (available online).

The following examples are provided to illustrate certain particular features and/or embodiments. These examples should not be construed to limit the disclosure to the particular features or embodiments described.

EXAMPLES

Example 1: Methods

This example describes the materials and experimental procedures used for the studies described in Example 2.

Participants and VirScan Analysis

The patient cohort consisted of 899 sequentially enrolled participants (clinicaltrials.gov number: NCT0091375), including 150 HCC cases, 337 CLD as at-risk individuals (HR or AR, used interchangeably) and 412 healthy volunteers as a population control (PC) matched by age and sex (FIG. 1A).

Study Cohorts

UMD cohort. To measure virome-host interplay, 899 participants were recruited. Participants were grouped as (1) population control (PC, n=412) if they were relatively healthy without any diagnosis of liver disease; (2) high-risk (HR, n=337) if they were diagnosed with chronic liver diseases (hepatitis B virus (HBV), hepatitis C virus (HCV), hepatitis delta virus (HDV), aflatoxins from fungal contamination, alcohol, nonalcoholic fatty-liver disease (NAFLD) and nonalcoholic steatohepatitis (NASH)); or hepatocellular carcinoma (HCC, n=150) if they were diagnosed with HCC. All clinic measurements were covered by NCT0091375 (clinicaltrials.gov) with the enrollment criteria as the liver disease status. Serum, matching buffy coat and cheek swab samples were collected from each individual.

NIDDK cohort. This cohort consisted of 173 patients with chronic liver disease that included 44 HCC cases with 129 controls matched by liver disease etiology, age and sex. Patients were enrolled in a natural history protocol (clinicaltrials.gov number; NCT0001971) with longitudinal follow-up, at least annually with serologic testing and imaging, for up to 20 years. Only cases with complete clinical and laboratory data and available longitudinal serologic samples were selected for analysis. The 44 HCC cases were sequentially identified out of 3,067 patients followed in this natural history study on chronic liver disease, and the controls were matched on a 2:1 basis as described above. HCC was diagnosed by radiologic imaging and/or liver biopsy as described by the American Association for the Study of Liver Disease (AASLD) practice guidelines (see Marrero et al., "Diagnosis, Staging and Management of Hepatocellular Carcinoma: 2018 Practice Guidance by the American Association for the Study of Liver Diseases," *Hepatology* 68(2): 723-750, 2018). For the purposes of this analysis, stored serum samples (–80° C.) were analyzed at study entry (baseline) and at recurrent time points until the time of HCC diagnosis.

Sample Collection

Blood samples were collected and stored at –80° C. (n=899 from UMD, n=488 from NIDDK). Buffy coat and cheek swab samples also were collected and stored at –80° C. (n=849 from UMD).

Virscan PhIP-seq

Phage immunoprecipitation and sequencing were performed using a slightly modified version of previously published PhIP-Seq protocols. First, 96-deep-well plates were blocked with bovine serum albumin in TBST overnight on a rotator at 4° C. The diluted 1 ml bacteriophage library was added in each blocked well. Serum samples, containing 2 mg IgG, were mixed with the bacteriophage library. Two technical replicates for each sample were set up. After an overnight rotation, protein A and protein G Dynabeads were added to each well. After another 4-hour incubation on a rotator at 4° C. with a 96-well magnetic stand, the beads were washed three times with 400 ml of PhIP-Seq wash buffer. Next, the beads were resuspended in water and lysed at 95° C. for 10 minutes. Blank PBS samples (instead of serum) were also set up as negative controls on each plate. Two rounds of PCR were performed to amplify and multiplex on the lysed bacteriophage DNA product. After the second round of PCR, PCR products were pooled using equimolar amounts of all 192 samples for gel extraction. After gel extraction, the size and quality of libraries were assessed on a Bioanalyzer instrument from Agilent. The DNA samples were aliquoted and stored at –80° C. until sequencing. Sequencing was performed using 50 bp single read protocol on Illumina HiSeq 4000 platform (1×50 bp), which obtained ~100 million to 200 million reads per lane (around 1,000,000 reads per sample in current setting).

Figure 5A:
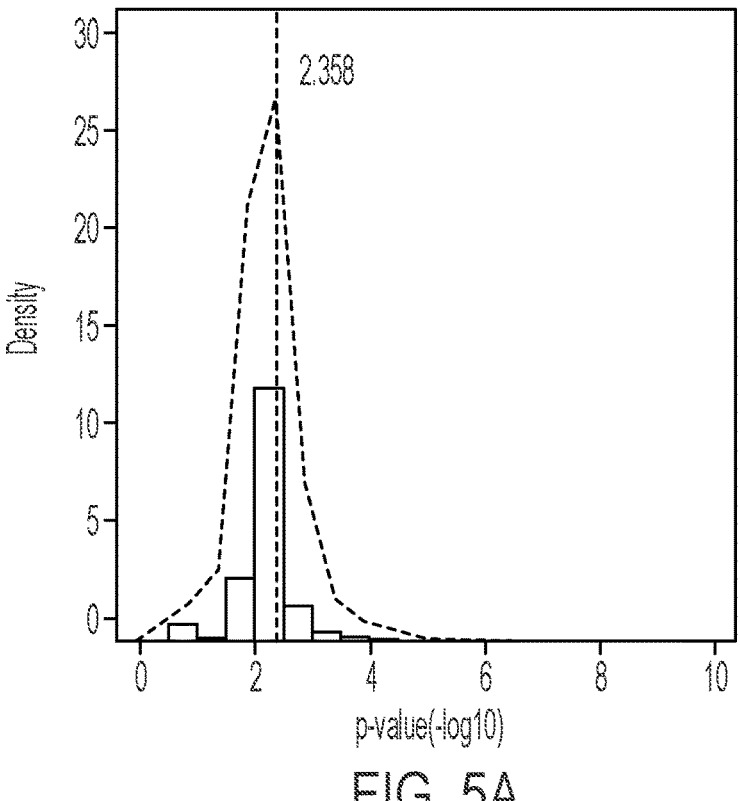
FIGS. 5A-5E: VirScan reproducibility and viral composition at DNA, RNA virus level and viral family level.
Figure 5B:
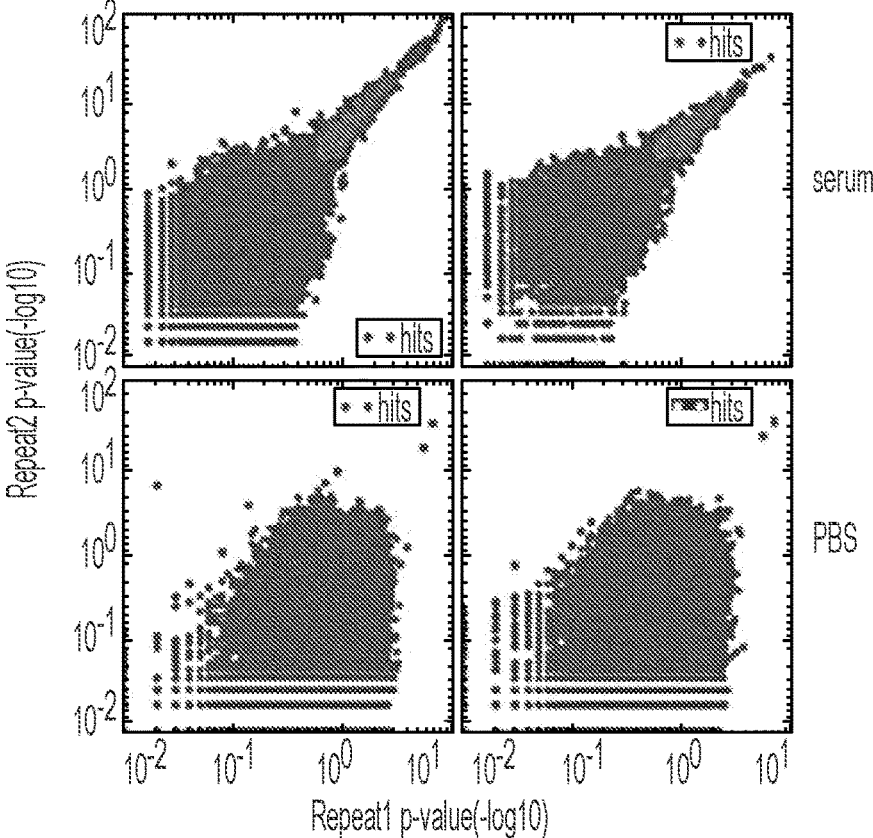

Raw data from Illumina HiSeq 4000 platform was processed by BCL2FASTQ2 for demultiplexing and converting binary base calls and qualities to fastq format. The fastq files were mapped to original virome peptide reference sequences using the Bowtie program. Two sequencing samples were cut off from next-step analysis as their reads were less than 30,000. The initial informatics and statistical analysis were performed using a slightly modified version of the previously published technique and in-house scripts. Briefly, the scatter plots of the log 10 of the –log 10 (P values) and a sliding window of width 0.005 from 0 to 2 across the axis of one replicate were used. It was determined that the distribution of the threshold –log 10 (P value) was centered around a mode of ~2.358 (FIG. 5B). The 593 hits that came up in at least 3 of the 22 immunoprecipitations with PBS beads alone blank sample were eliminated. Also, any peptides that were not enriched in at least two of the samples were filtered out. A threshold number of hits per virus was set based on the size of the virus. If the hit shared a subsequence of at least 7 amino acids with any hit previously observed in any of the viruses from that sample, that hit was considered to be from a cross-reactive antibody and would be ignored for that virus. The peptide hits, which do not share any linear epitopes, were summed to be strain and species score data. The final score was compared for each virus to the threshold for that virus to determine whether the sample is positive for exposure to that viral species. The raw count data were calculate based on –log 10(p-value) 2.358 cutoff.

DNA Sample Extraction

DNA extraction from buffy coat or lymphocyte samples was performed following the manufacturer's instruction (DNeasy Blood & Tissue Kit from Qiagen). The eluted DNA was stored at –20° C. for further analysis.

GWAS Platform

Illumina OmniExpress was applied for the SNP array. Genotyping was performed on 200 ng of genomic DNA using Illumina Infinium HTS Global Screening Arrays on an Illumina iScan system. The raw genotyping data were processed by Illumina GenomeStudio software 2.0. Quality control was performed using PLINK version 2.0 (available online). Samples with a genotyping call rate<95% were removed. SNPs with MAF (Minor Allele Frequency)<0.05, HWE (Hardy-Weinberg equilibrium)<10-4, and call rate<95%, were excluded.

GWAS Analysis

Variant quality control was performed. After filtering, 849 individuals and 713,111 SNPs remained for further analysis, with the total genotyping rate 99.79%. Hardy-Weinberg equilibrium deviation was flagged at p value <0.0001. Independent loci in regions were identified for SNPs associated with virus feature phenotype at P<5×10-7 using PLINK. LocusZoom was used to plot regional signals associated with phenotype with LD and recombination rate calculated from 1000 Genome. LD structure of signals were further investigated with Haploview. A linear regression with additive model was applied to estimate the genotypic effect the SNP contributed to the disease or phenotype.

ELISA Assay

IgG, IgA and IgG4 levels in serum were measured using human ELISA kits (Bethyl and Thermo Fisher) according to the manufacturers' instructions. ELISA result reading was performed using a machine (Biorad).

Statistical Methods

To identify differences between populations, Xgboost and LEfSe were used to calculate the significance of association of virus exposure traits with HCC versus PC.

XGBoost

XGBoost (available online) is software for a machine learning method of regression and classification using ensemble learning with gradient tree boosting. It is designed to increase the scalability and acceleration of optimized computation for practical use. XGBoost includes three types of parameters—general, booster and task. Each of the types has several hyperparmeters, such as maximum depth of the regression trees, number of weak learners, learning rate, and regularization, that need to be tuned. These parameters were tuned using a grid search to maximize the mean AUC value computed from 5-fold cross validation on the training data. After finding the optimal values of the hyperparameters, the model was constructed using the following main parameter setting: max_depth=3, eta=0.1, subsample=1, colsample_bytree=0.5, and min_child_weight=1. Then XGBoost was applied to the entire data set with 200 boosting iterations. To avoid over-fitting, stop model training at least 20 rounds when no improvement was observed in AUC value was set (early_stopping_rounds=20). The best iteration model was used as the final model. XGBoost automatically conducts feature selection and calculates importance for each feature. Multiple subsets of the features were tested to achieve the highest AUC and a decision was made to take all of the output features for further analysis. For each training and testing sample, a virus feature score was also generated based on the features selected and implemented in the XGBoost classification prediction.

LEfSe

The LEfSe method of analysis first compares abundance of all viral clades (in this case between PC and HCC) by Kruskal-Wallis test at a pre-defined a of 0.05. Significantly different vectors resulting from the comparison of relative abundances between PC and HCC are used as input for linear discriminant analysis (LDA), which produces an effect size and a p-value. The LDA threshold on the logarithmic LDA score for discriminative features is set up at 2.0. LEfSe also calculated the hierarchically organized viral taxa. The relative abundance data for Lefse test was prepared based on strain and species score data.

Additional Statistical Methods

All analyses were conducted in R and GraphPad Prism 7 (La Jolla, CA) and used for statistical analyses. Data are presented either as means+/–s.e.m. or medians of continuous values and were analyzed by a two-sided Student's t-test or Mann-Whitney test used for comparison of two groups, respectively. Fisher's exact X2 t-test was used to calculate statistical significance of categorical values between groups. Two-tail P values with no more than 0.05 were considered significant. Linear regression was used to determine the correlation between two different variables.

Viral Feature Level, Clinical Outcome and ROC Curve

Figures 4A, 4B, 4C:
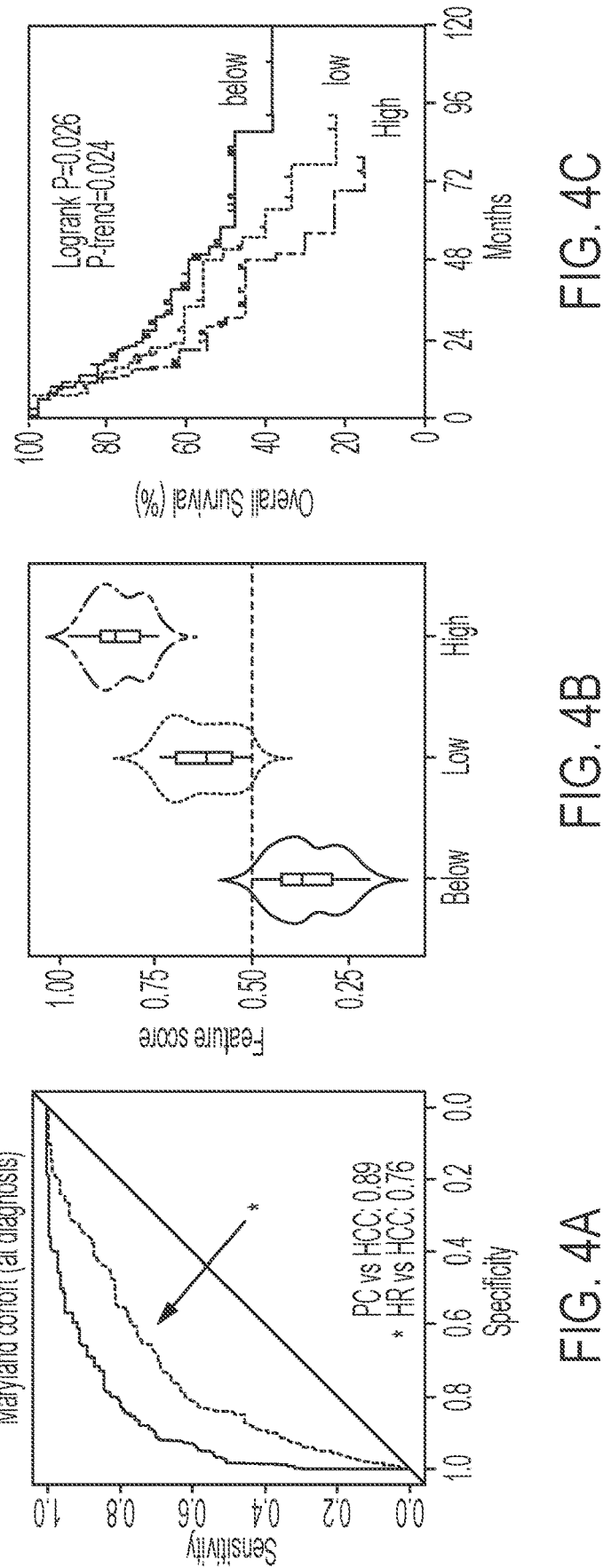
FIGS. 4A-4H: Determination of VES predictive accuracy and association with clinical outcomes.
Figure 6A:
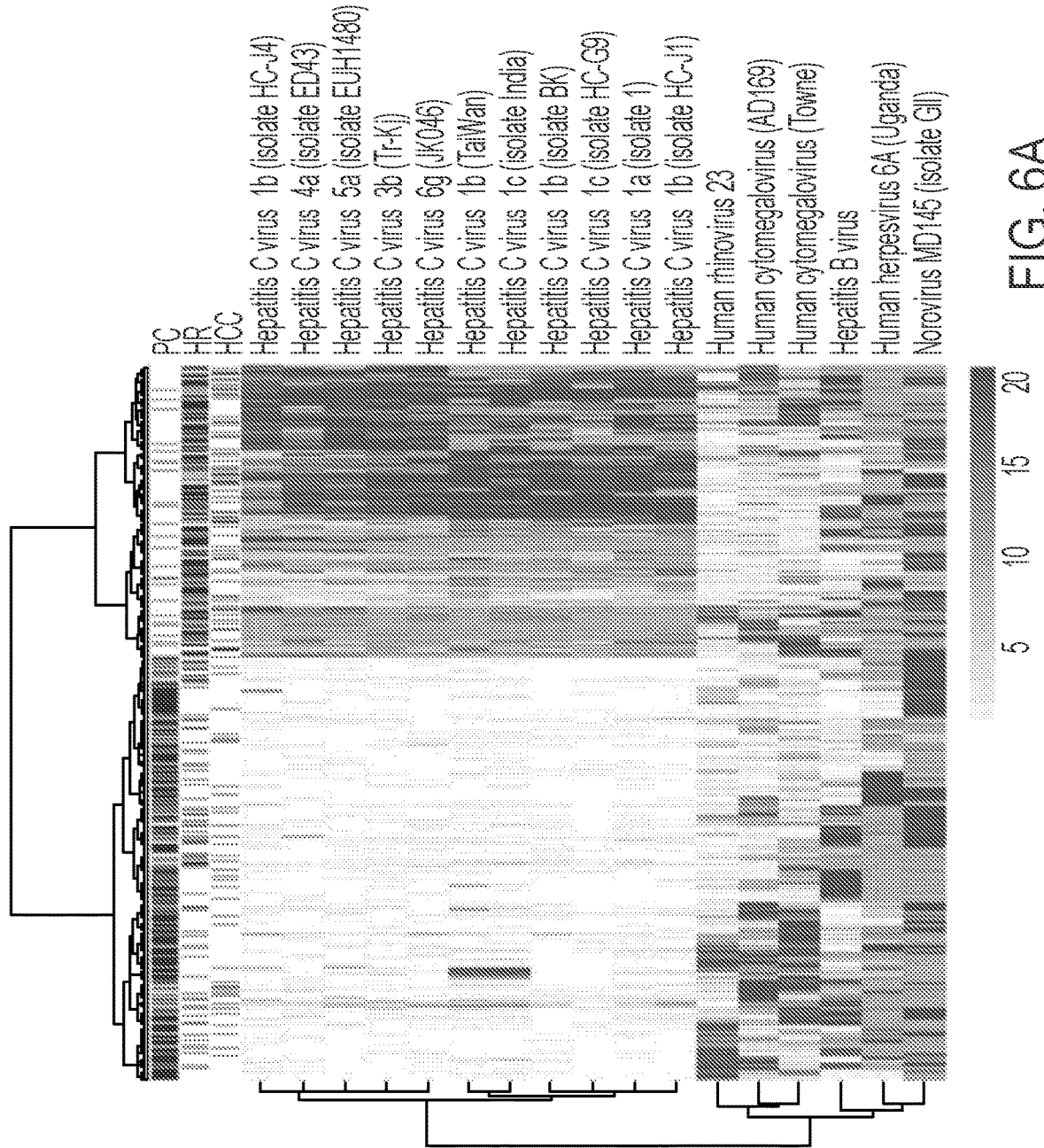
FIGS. 6A-6B: Extended information of composition of viral features in the investigated population.

All HCC patients were classified into high, low or below viral feature score groups based on viral feature levels (FIGS. 4B and 6A). Kaplan-Meier estimates of overall survival were estimated for each group and compared using the log rank test. Hazard ratios and 95% confidence intervals were calculated using univariate and multivariate Cox proportional hazards models to assess associations between different viral feature level along with several clinical factors. The ability of clinical and viral features in predicting HCC was assessed by computing receiver operating characteristic (ROC) curves using the logistic regression in R. Area under the curve (AUC) values were calculated for these variables.

Example 2: Viral Exposure Signature (VES) for Diagnosis of Hepatocellular Carcinoma (HCC)

This example describes the development of two virus exposure signatures—a first VES based on detection of 61 viral strains and a second VES based on detection of 31 viral strains—to identify subject's at risk for developing HCC.

The Landscape of Viral Exposure Profiles

Figures 1B, 1C, 1D:
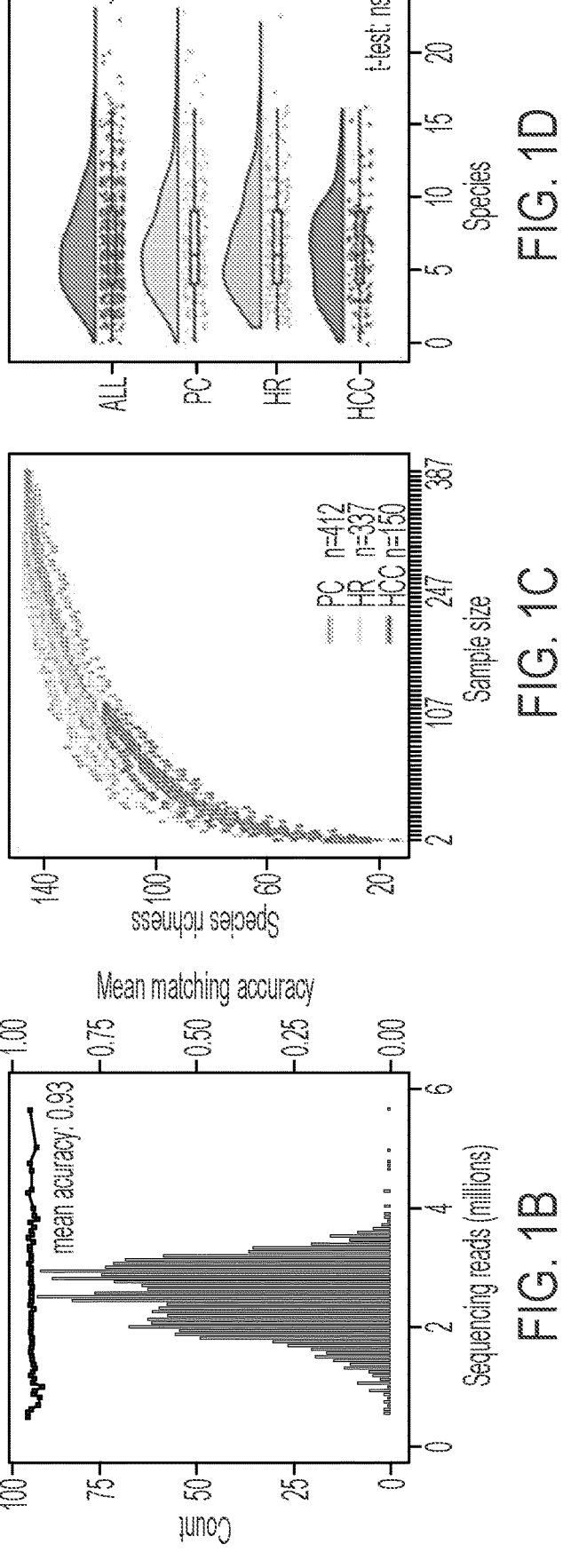
Figure 1E:
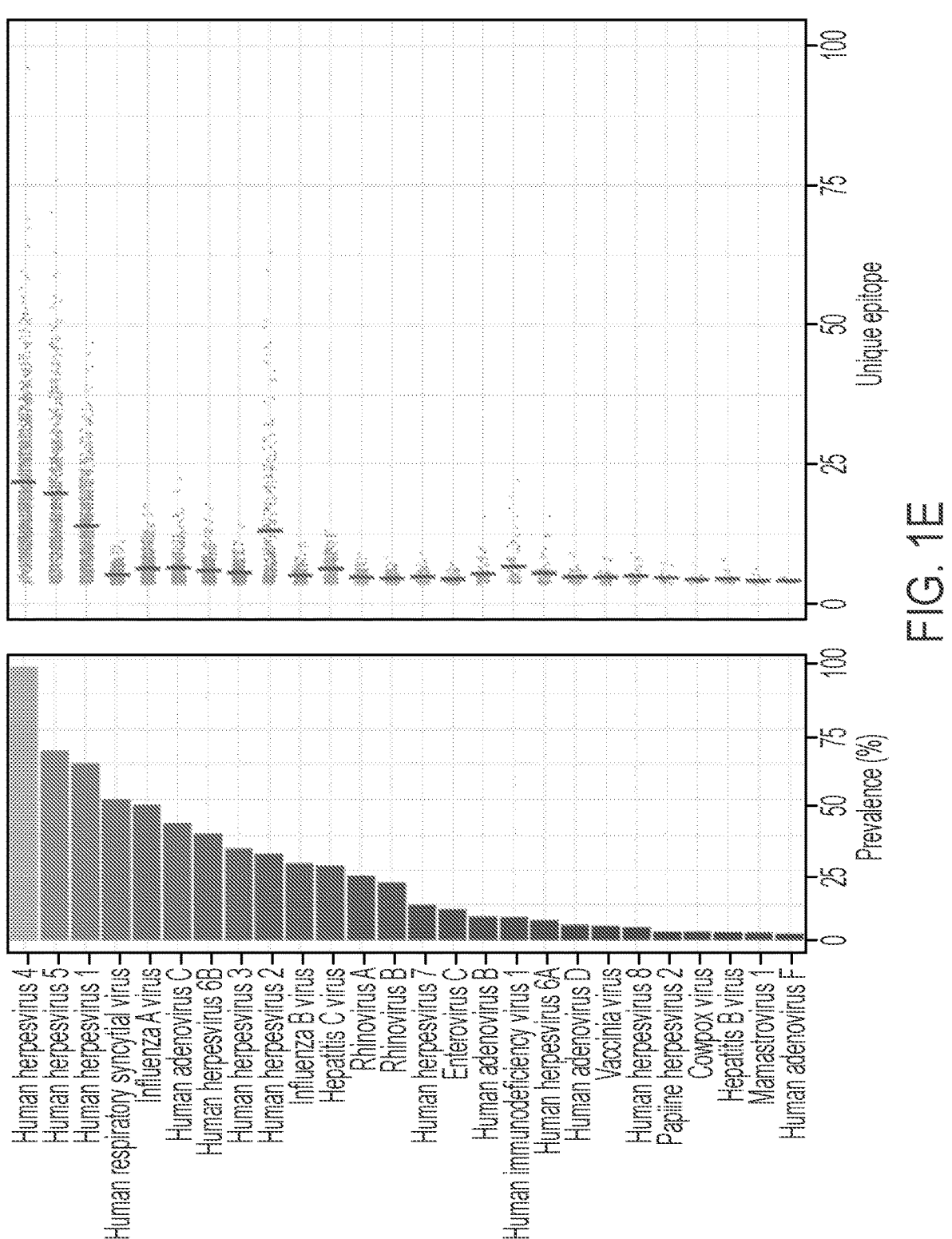
Figure 5C:
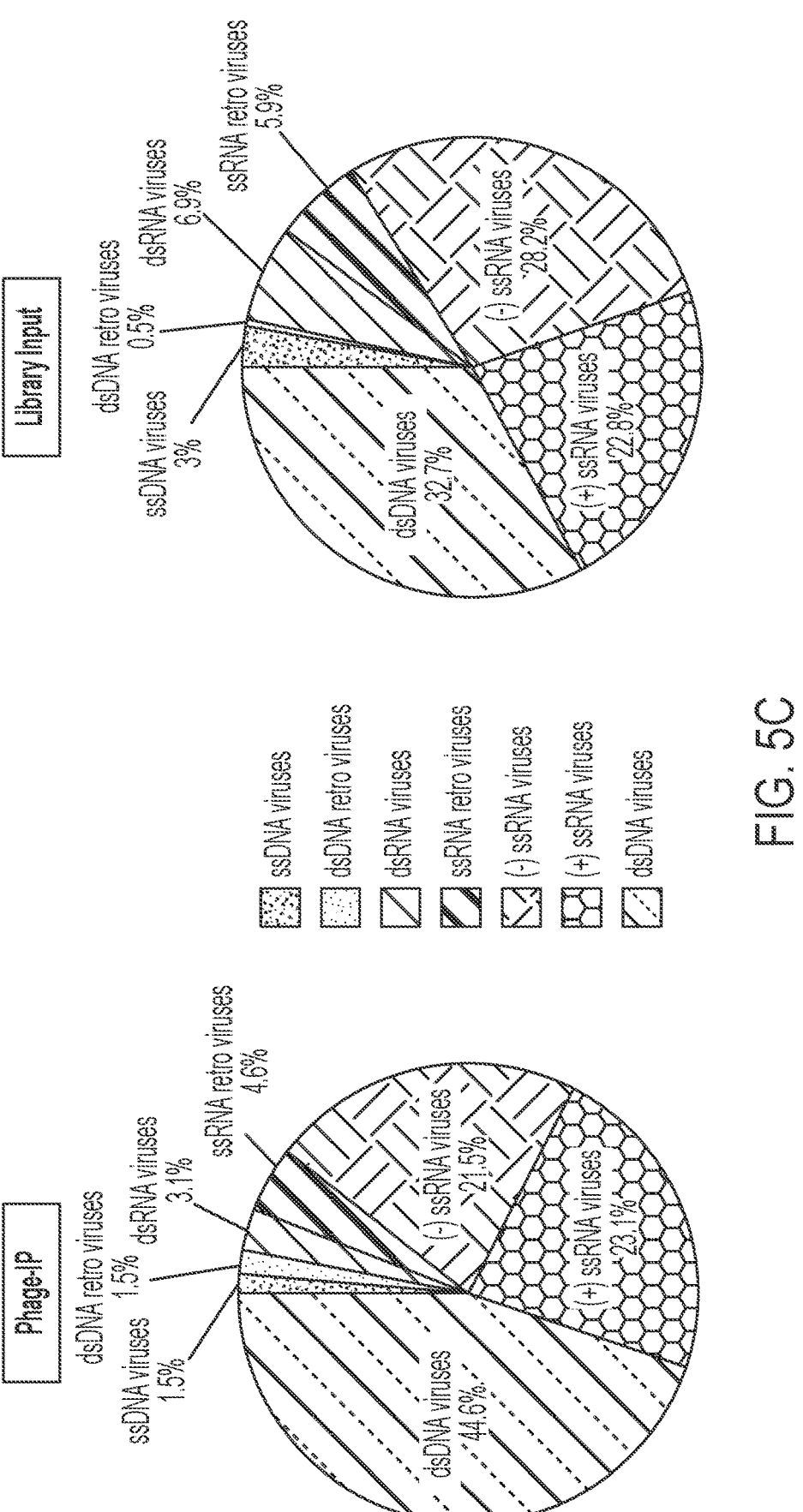
Figure 5D:
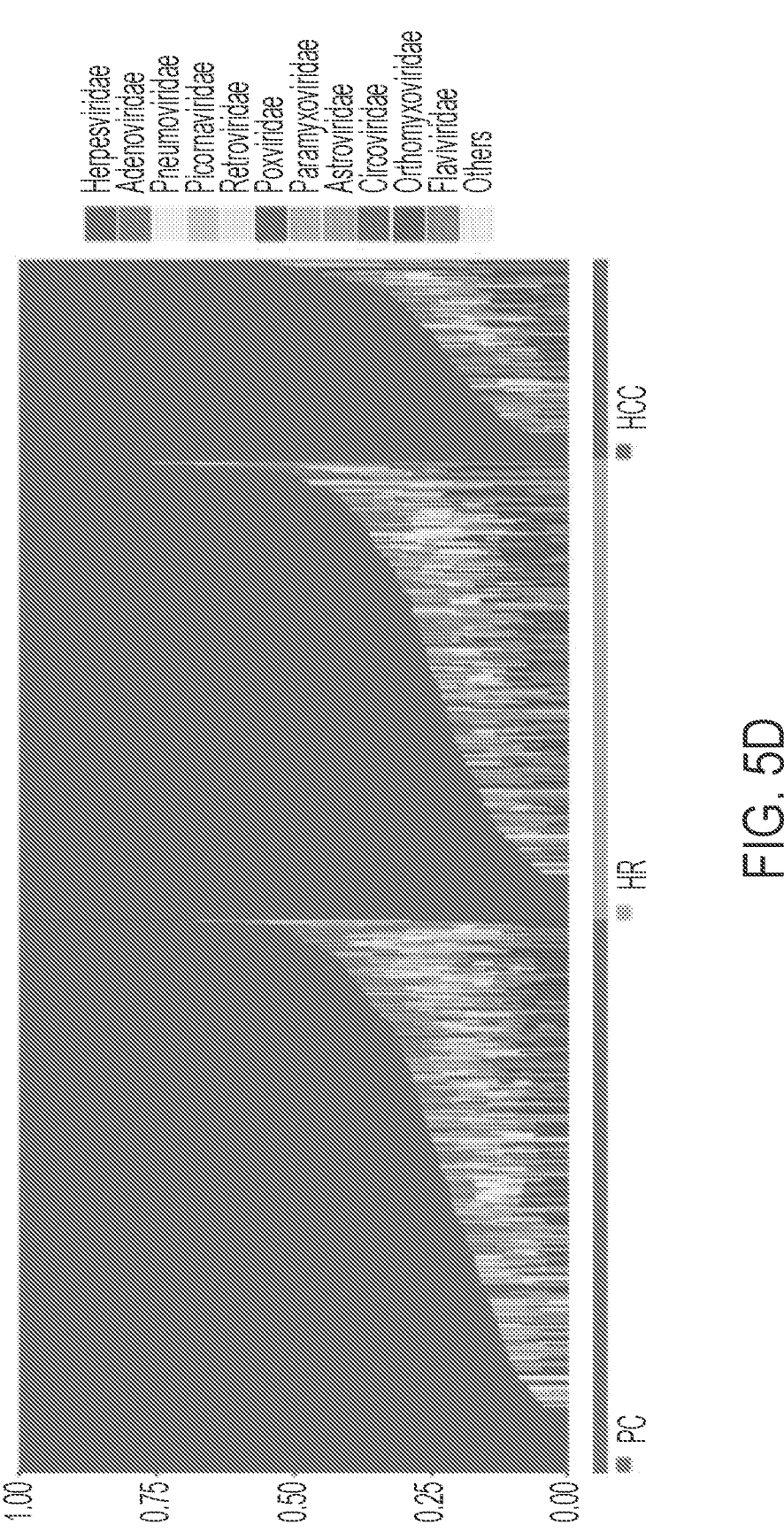
Figure 5E:
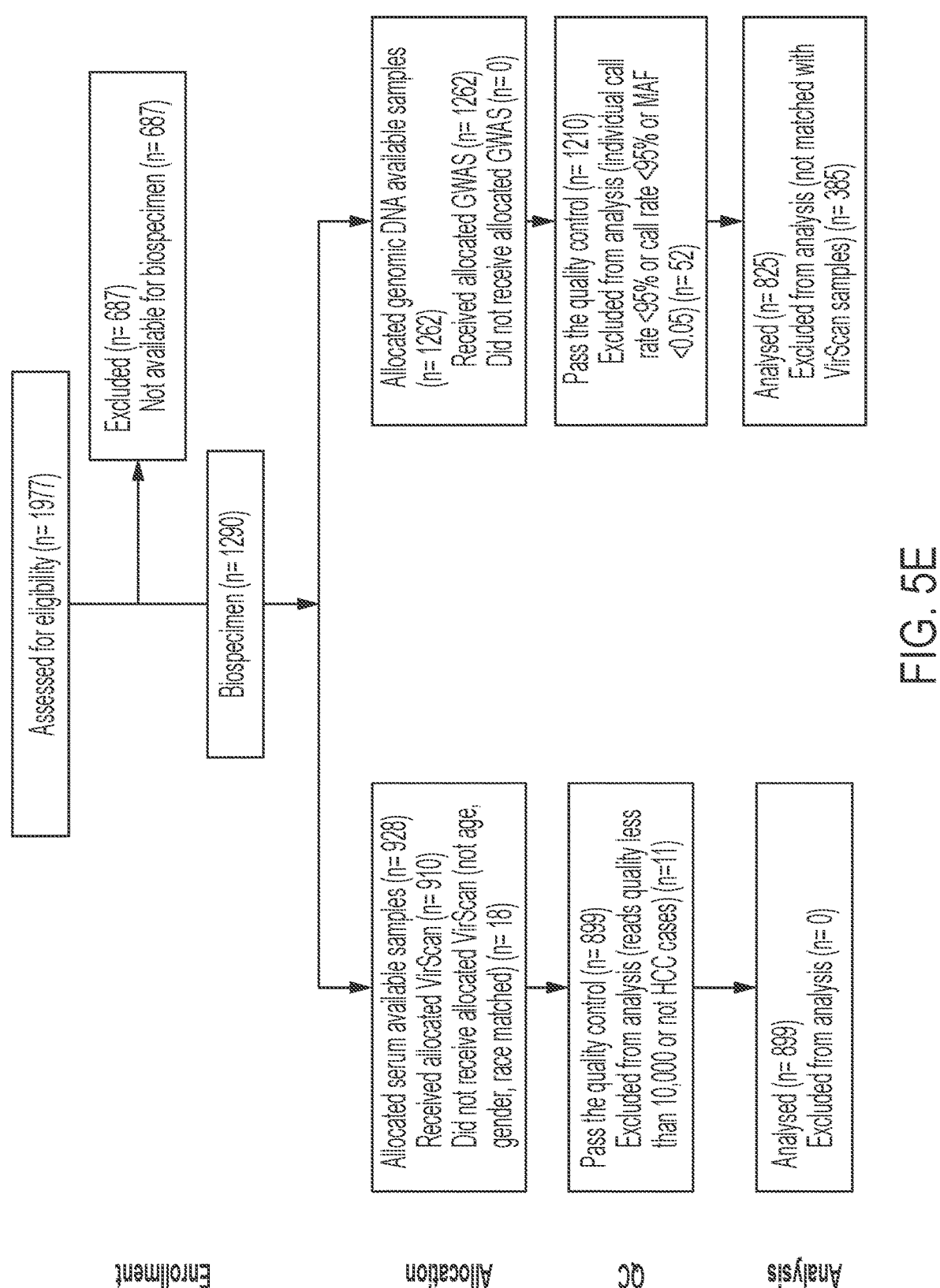
Figure 10:
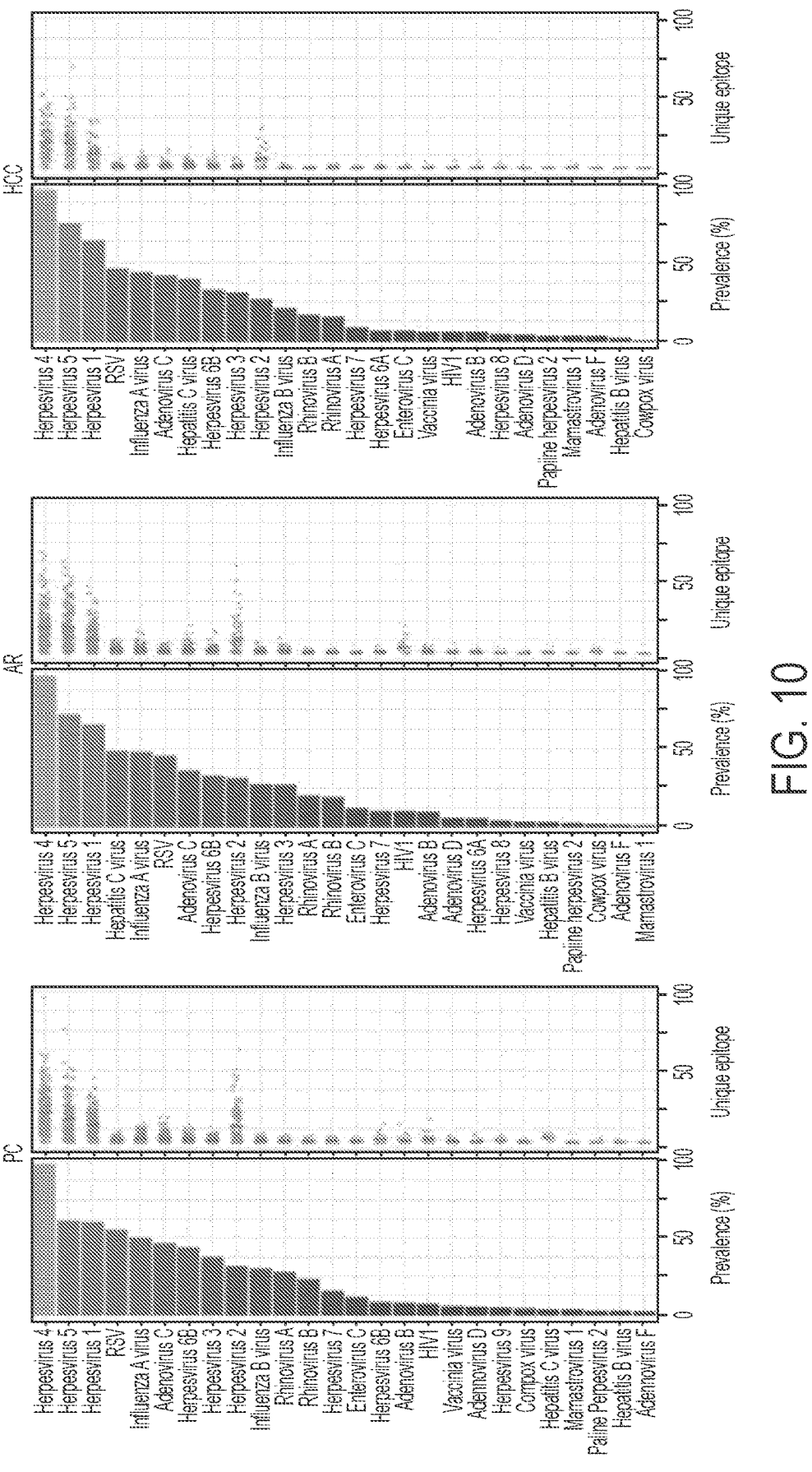
FIG. 10: Viral infection prevalence and unique viral epitope count across population control (PC), at risk group (AR), and HCC group. The viral infection prevalence across all PC, AR and HCC samples is shown on the bar plots. The count of unique epitopes per sample is shown on the dot plot and the vertical lines represent the mean values of the count of unique epitopes.

VirScan applies a phage display library that covers 93,904 viral epitopes, representing 206 human viral species and over 1000 viral strains, to screen for previous exposure history (Xu et al., Science 2015; 348:aaa0698). A phage particle with an epitope that was recognized by a participant's antibody was immunoprecipitated (Phage-IP), and the encoding DNA barcode was then sequenced (FIG. 1A). A case-control design of the Maryland (NCI-UMD) cohort was used for the discovery of viral exposure profiles. The inclusion and enrollment of the study subjects are outlined in FIG. 5E, following the CONSORT guideline (Schulz et al., *BMJ* 340:c332, 2010) (Table 8). For the NCI-UMD cohort, VirScan Phage-IP products yielded 0.5-5 million single-end reads per serum sample, with the mean of the mapped reads rate of 0.93 (FIG. 1B). A total of 30,033 viral epitopes were significantly enriched with a p-value ($-\log 10$) greater than the reproducibility threshold of 2.358 based on both replicates (FIGS. 5A-5B). It was noted that the composition of the viral types at the viral taxonomic level showed small yet noticeable differences between the obtained Phage-IP products and the library input (FIGS. 5D-5E), indicating a measurable difference between patients-derived data and the original input. When assessing viral richness among PC, HR and HCC, it was determined that the numbers of viral infection increased along with the sample size and reached saturation at the sample size over 200 (FIG. 1C). An average of 7 species of virus per sample was detected and more than 20 out of 206 viral species were found in four individuals (FIG. 1D). Overall, the distribution of viral species was similar among PC, HR and HCC (FIG. 1D), indicating no bias in the landscape of overall viral exposure profiles between different groups. The abundance of the most prevalent viral species among all volunteers such as human herpesvirus 4 (EBV) and human herpesvirus 5 (HCMV) was similar to a prior population study (FIG. 1E, Table 2A) (Xu et al., Science 2015; 348:aaa0698), and was consistent with previous epidemiology reports (Straus et al., Ann Intern Med 1993; 118:45-58; Ho, Rev Infect Dis 1990; 12 Suppl 7:S701-S710). However, the HCV infection rate (26.4%) in this study was relatively high, which was mainly contributed by AR (48.4%) and HCC (39.3%) (Table 2A; FIG. 10). A wide range of unique viral epitopes for each viral species that were recognized among different participants was detected, indicating that B-cell antigenicity to the same viral species is diverse among the participants (FIG. 1E, right panel; FIG. 10). Moreover, global compositions of the viral types at the viral taxonomic level show small but noticeable differences between Phage-IP products and the library input (FIGS. 5C-5D).

Figure 2A:
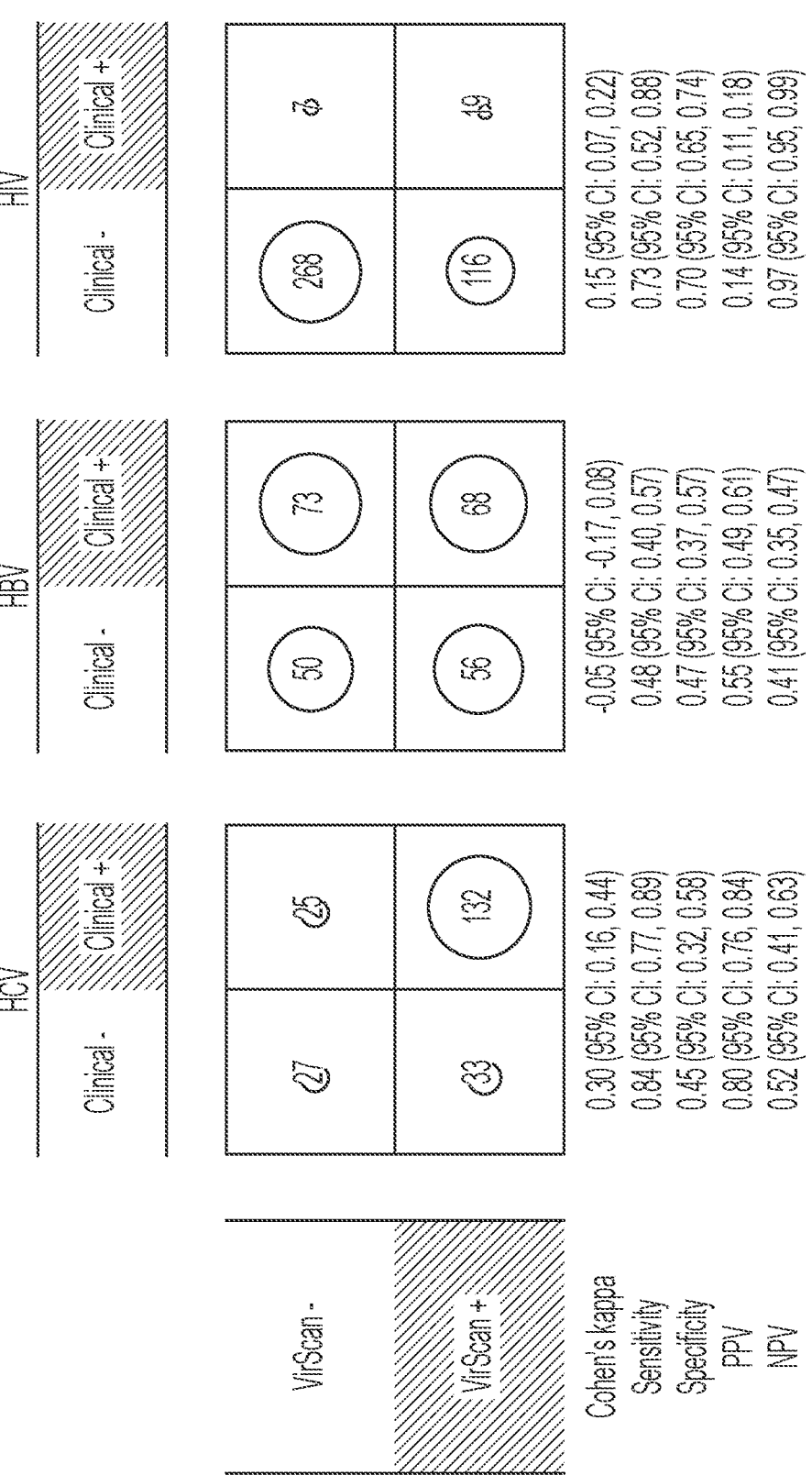
FIGS. 2A-2C: Comparison of VirScan with medical charts, antigenicity of HCV1b and HIV coinfection viruses.
Figure 2B:
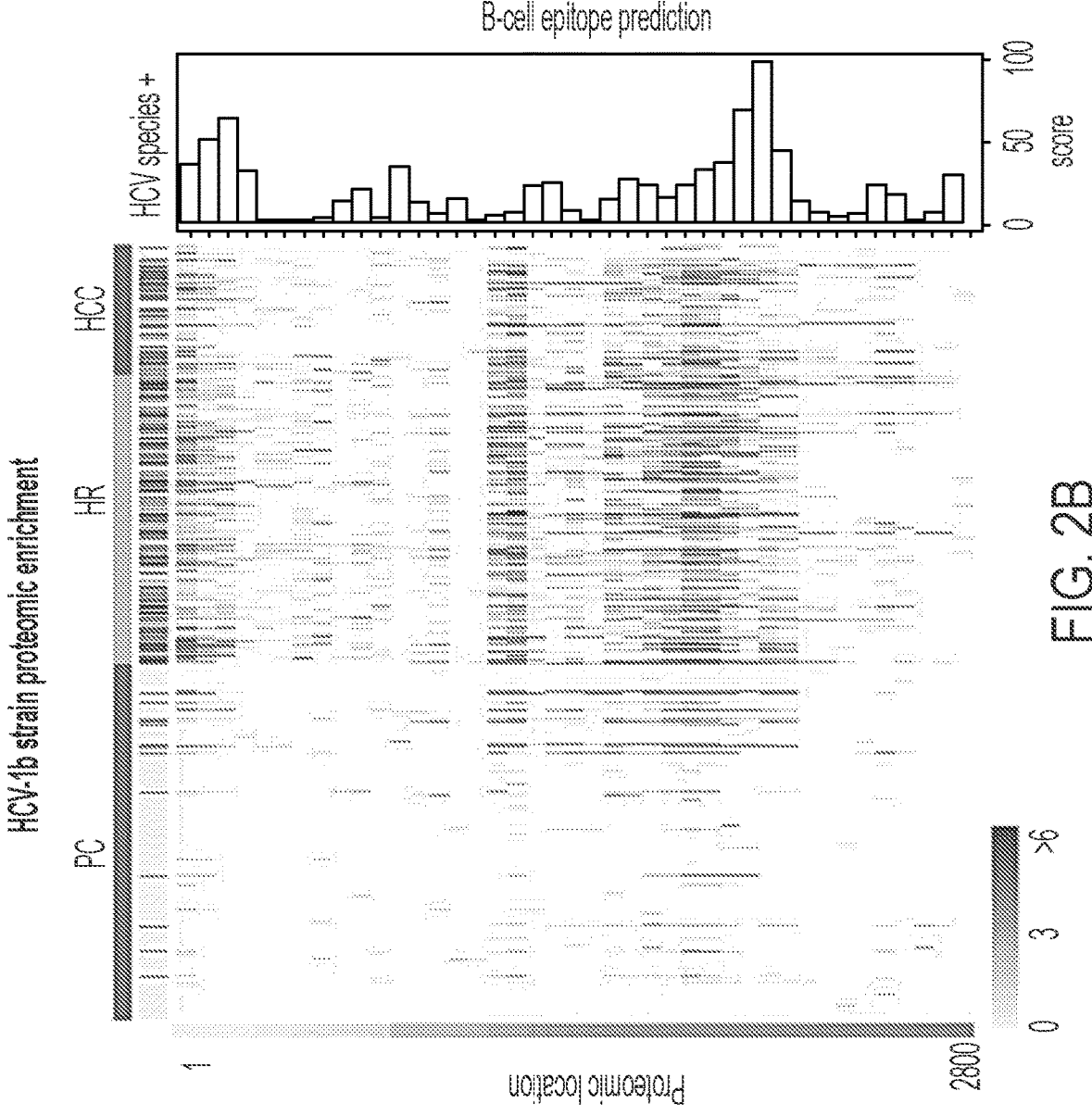
Figure 2C:

To further assess the quality of VirScan, the results of VirScan were compared to available medical chart entries for HCV, HBV and HIV testing results and found that VirScan had 45%, 47% and 70% specificity in detecting HCV, HBV and HIV, respectively, when compared to these medical record data (FIG. 2A). In contrast, its sensitivity was 84% for HCV, 48% for HBV and 73% for HIV. A majority of viral status data from medical charts was unknown or missing (Table 2B), which makes this comparison suboptimal. Epitope enrichment of HCV1b, a major type associated with HCC (Bruno et al., Hepatology 2007; 46:1350-1356), was also examined. Consistently, an increase in peptide enrichment, corresponding mainly to the core, NS4 and NS5A of HCV1b, was observed among AR and HCC compared to PC, and these regions were consistent with the prediction score of B-cell antigenicity (FIG. 2B). The presence of HIV and other viruses known to have co-infection with HIV (Xu et al., Science 2015; 348: aaa0698; Chang et al., Immunol Rev 2013; 254:114-142; Echavarria, Clin Microbiol Rev 2008; 21:704-715; Stover et al., J Infect Dis 2003; 187:1388-1396) was also examined. A significant increase of co-infection between HIV and human herpesvirus 5, human adenovirus C, human adenovirus D, human herpesvirus B or HBV was found, with a false discovery rate (FDR)<0.05 (FIG. 2C). Taken together, the above results revealed that VirScan is a reliable method to capture a broad spectrum of viral exposures with a serological test.

HCC-Associated VES

Figures 3A, 3B:
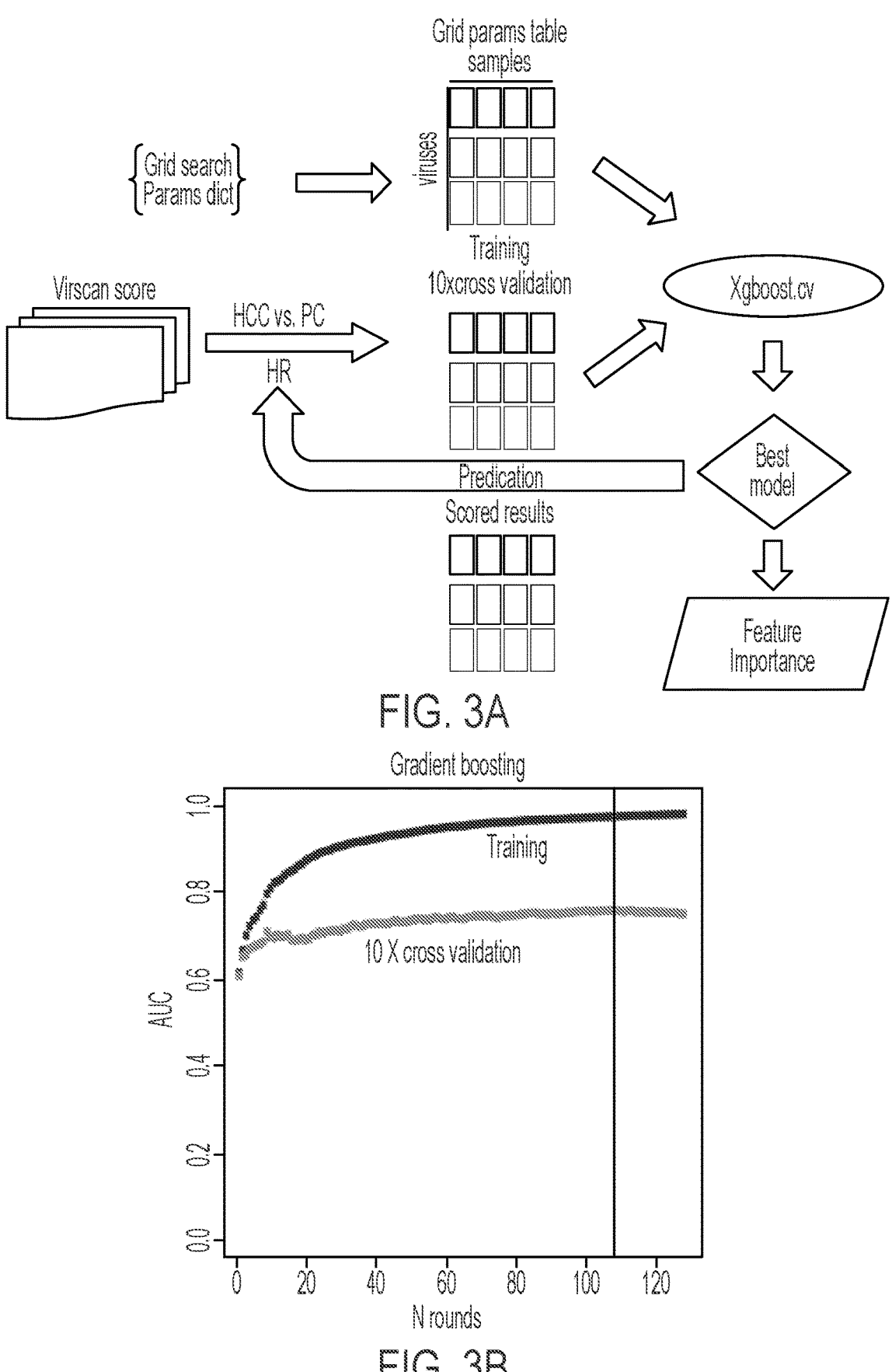
FIGS. 3A-3F: Composition of VES associated with HCC.
Figure 3C:
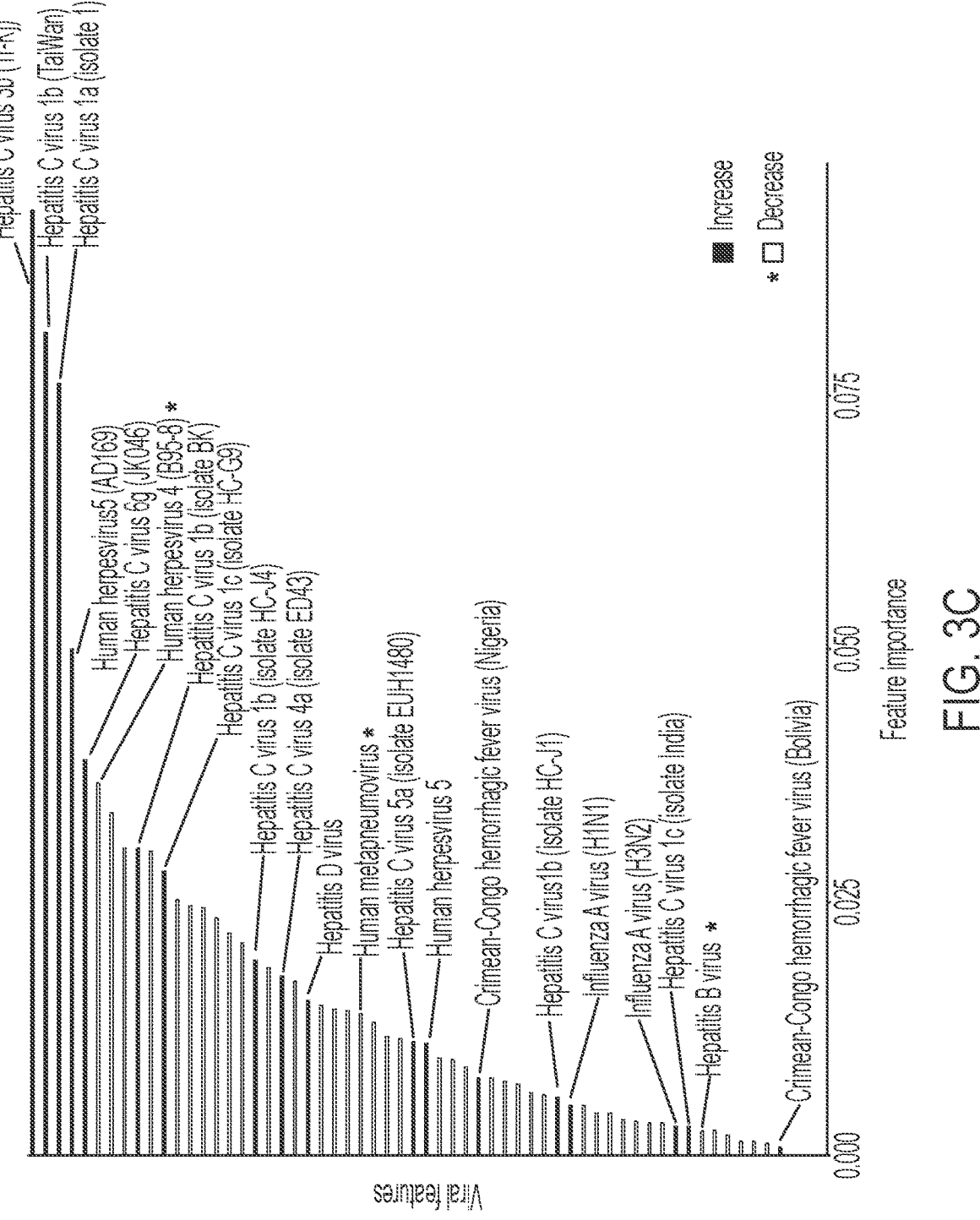
Figure 3D:
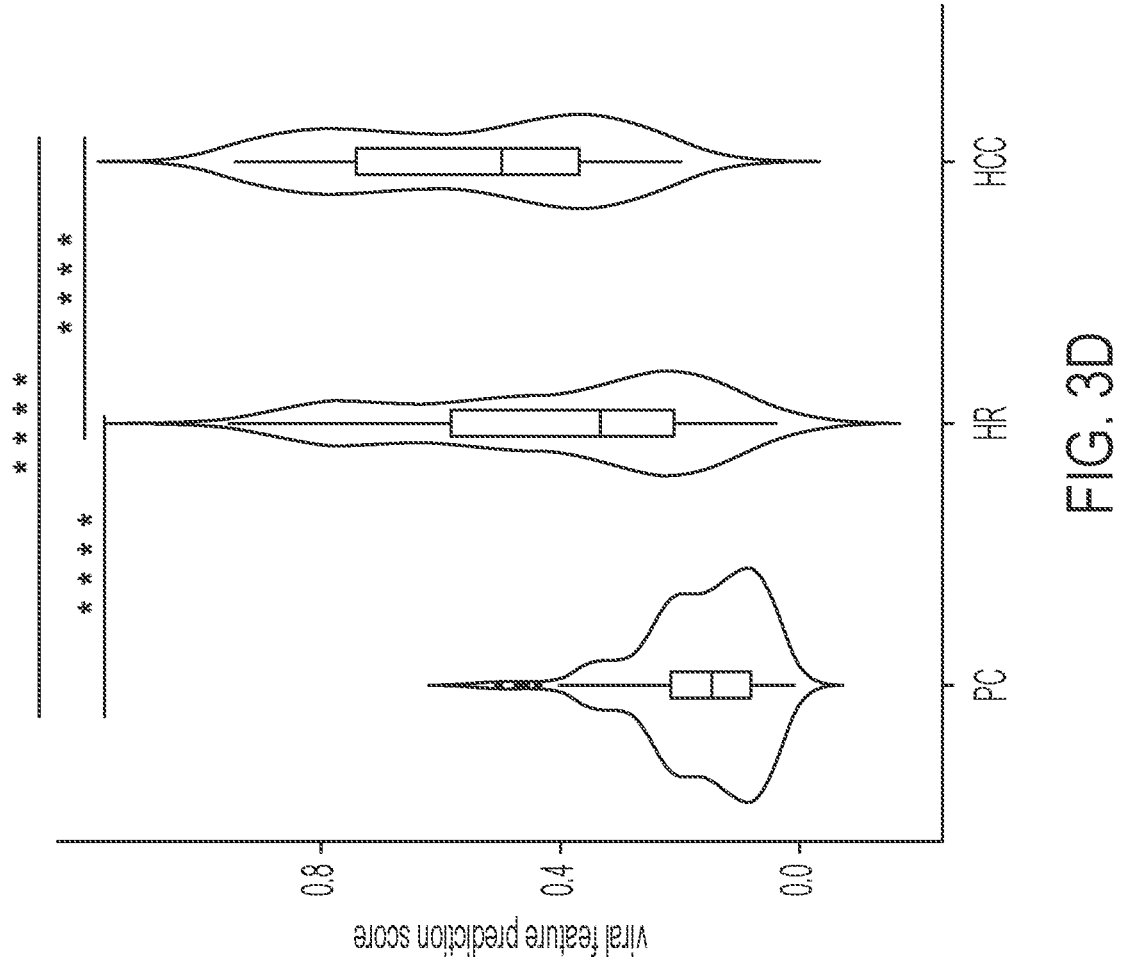

A gradient boosting approach was applied to search for the best-fit virus composition that can discriminate HCC from PC (FIG. 3A). Using 10-fold cross validation and 1,000 random permutations, it was found that a VES can significantly discriminate HCC from PC with an AUC value of 0.9 and 0.7 for training and cross validation, respectively (FIG. 3B). This signature consisted of unique peptides corresponding to 61 viral strains (FIG. 3C). Among them, 18 viruses were positively associated, while the remaining viruses were negatively associated, with HCC. HCV, including 11 unique variants such as 3b or Taiwan 1b among others, was the main contributing virus in the signature. This was not surprising since 39.3% of HCC cases from this cohort were HCV+. It was also found that herpesvirus 5, HDV, influenza virus H1N1 and influenza virus H3N2 were enriched in the HCC group. In contrast, 43 viruses, such as human respiratory syncytial virus and human rhinovirus 23, were preferentially depleted in the HCC group (Table 5A, FIG. 3C). Weighed VES scores of the 61 viruses differed significantly between HCC and PC (p<0.0001), as well as HCC and HR (p<0.0001), or HR and PC (p<0.0001) (FIG. 3D). There was a significant increase among PC, HR and HCC (ptrend<0.0001), suggesting that the VES was positively linked to hepatocarcinogenesis.

Figure 3E:
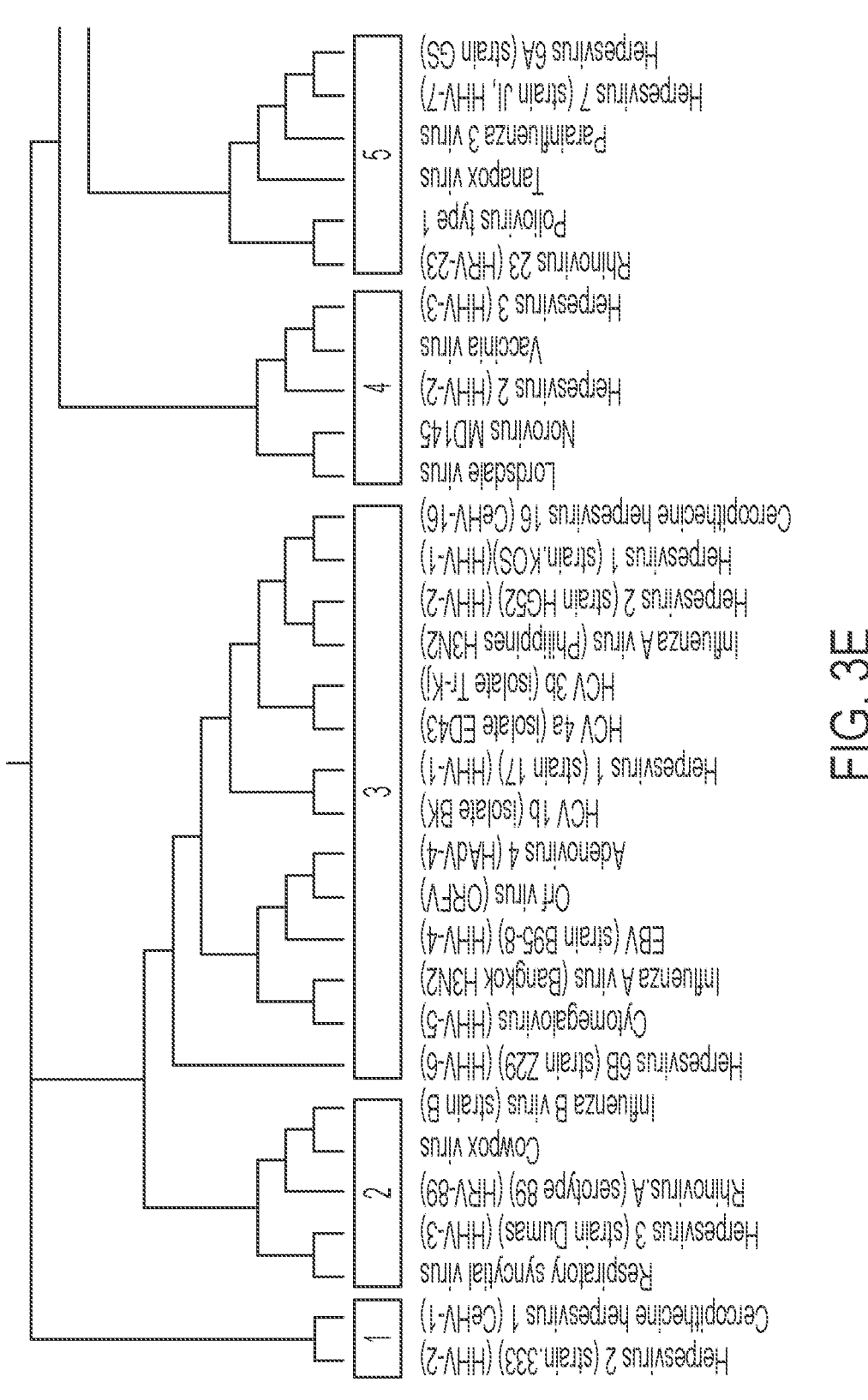
Figure 3F:
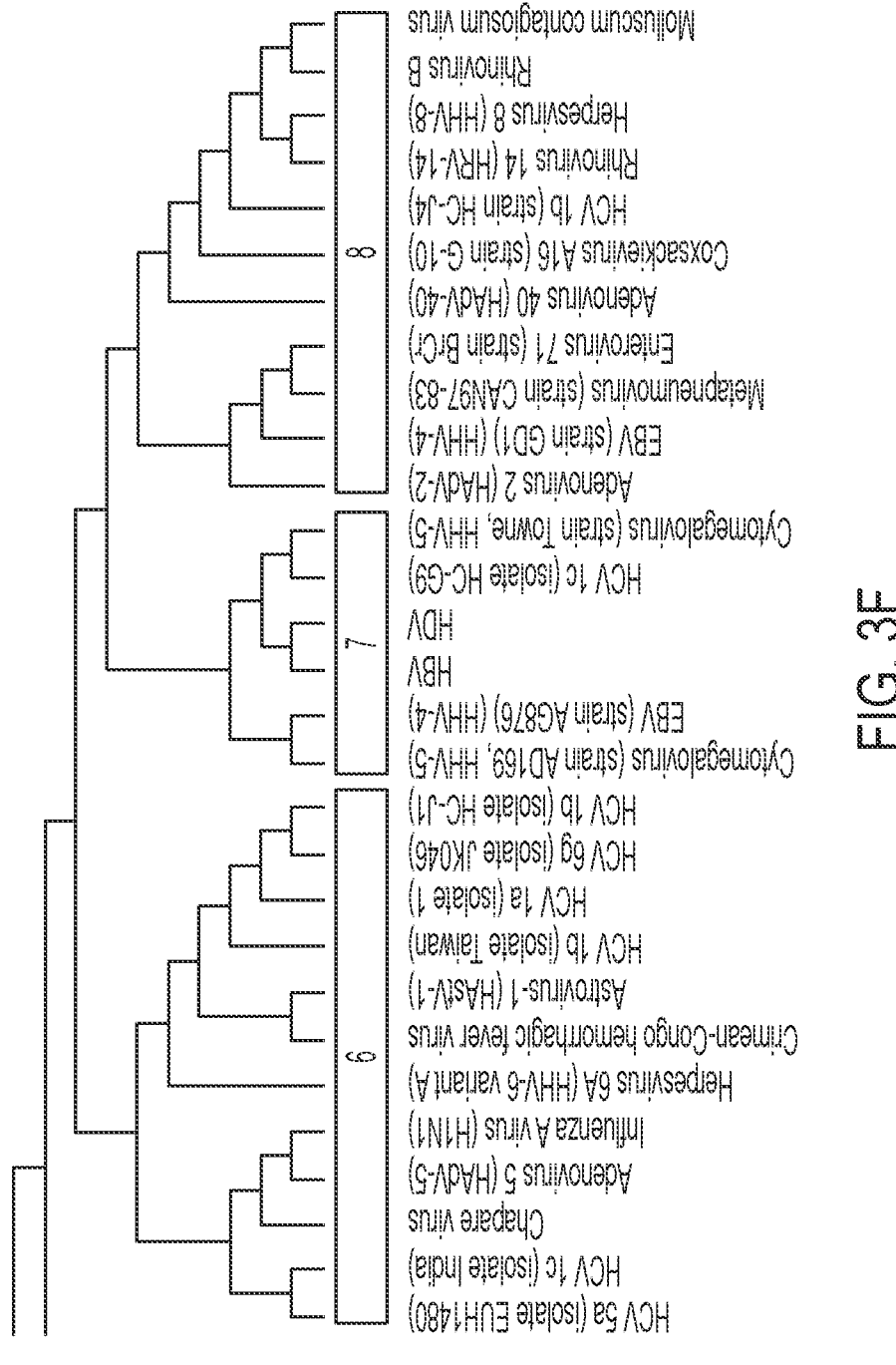
Figures 11A, 11B, 11C:
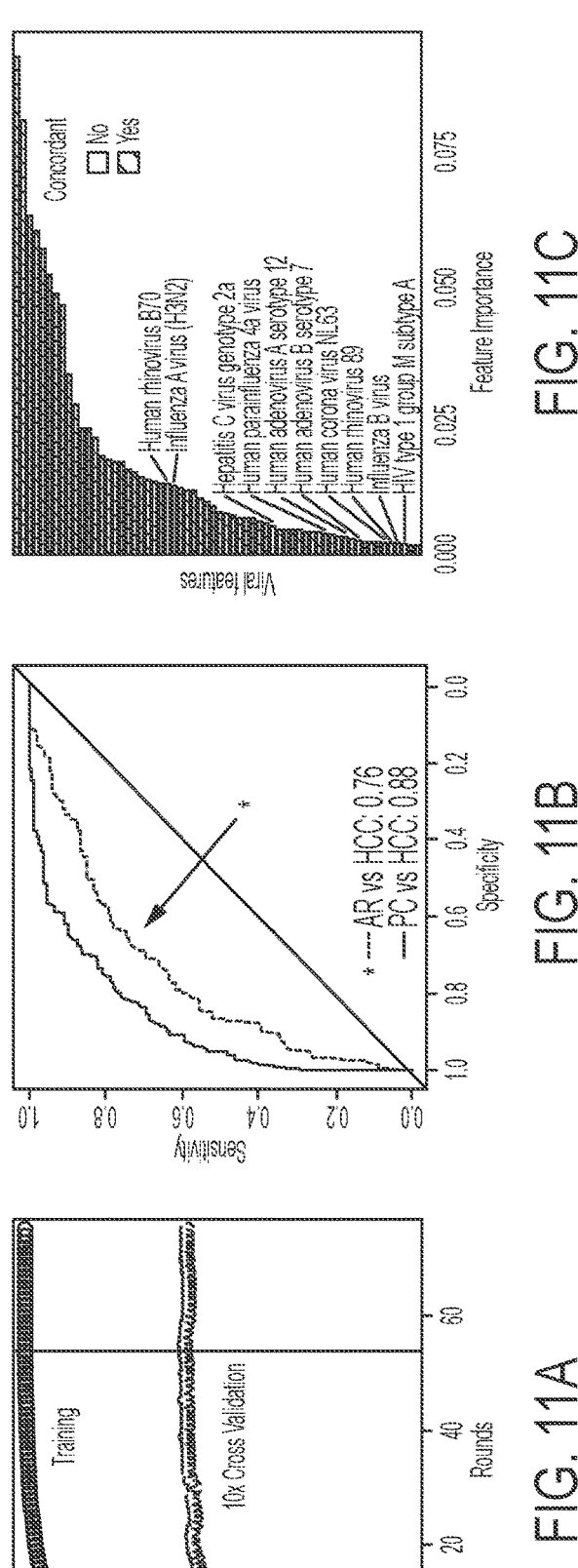
FIGS. 11A-11J: Further validation of robustness of the 61-VES.
Figures 11D, 11E, 11F:
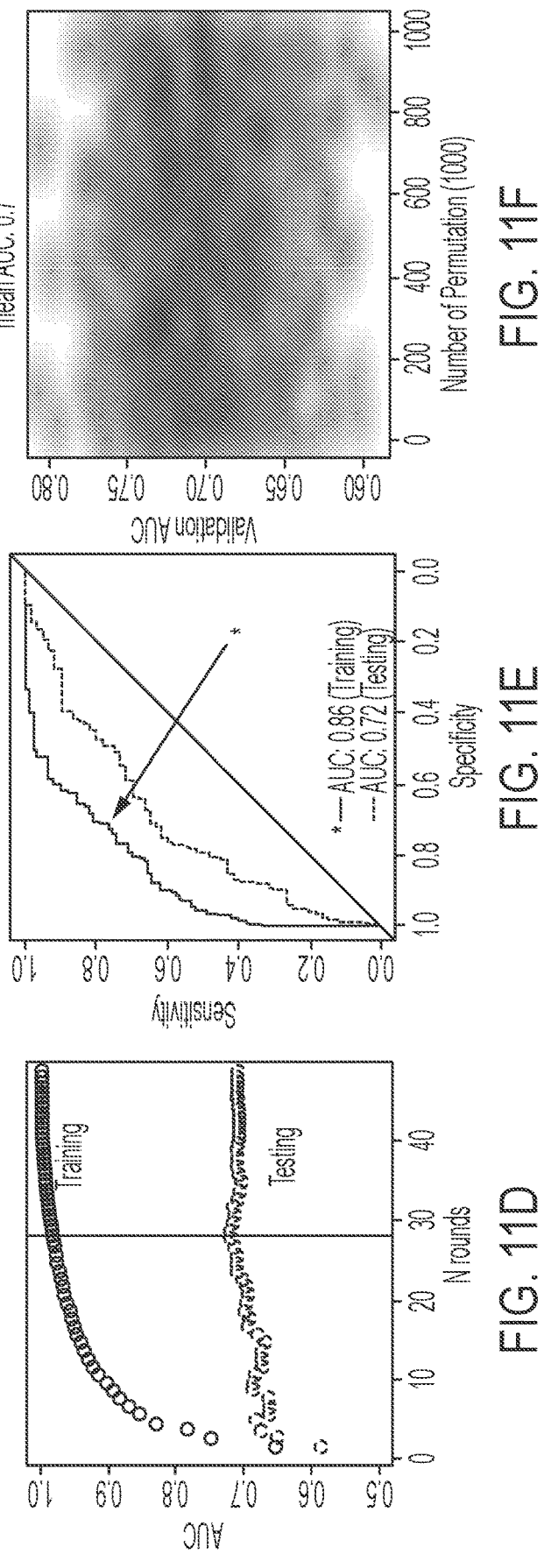
Figure 11G:
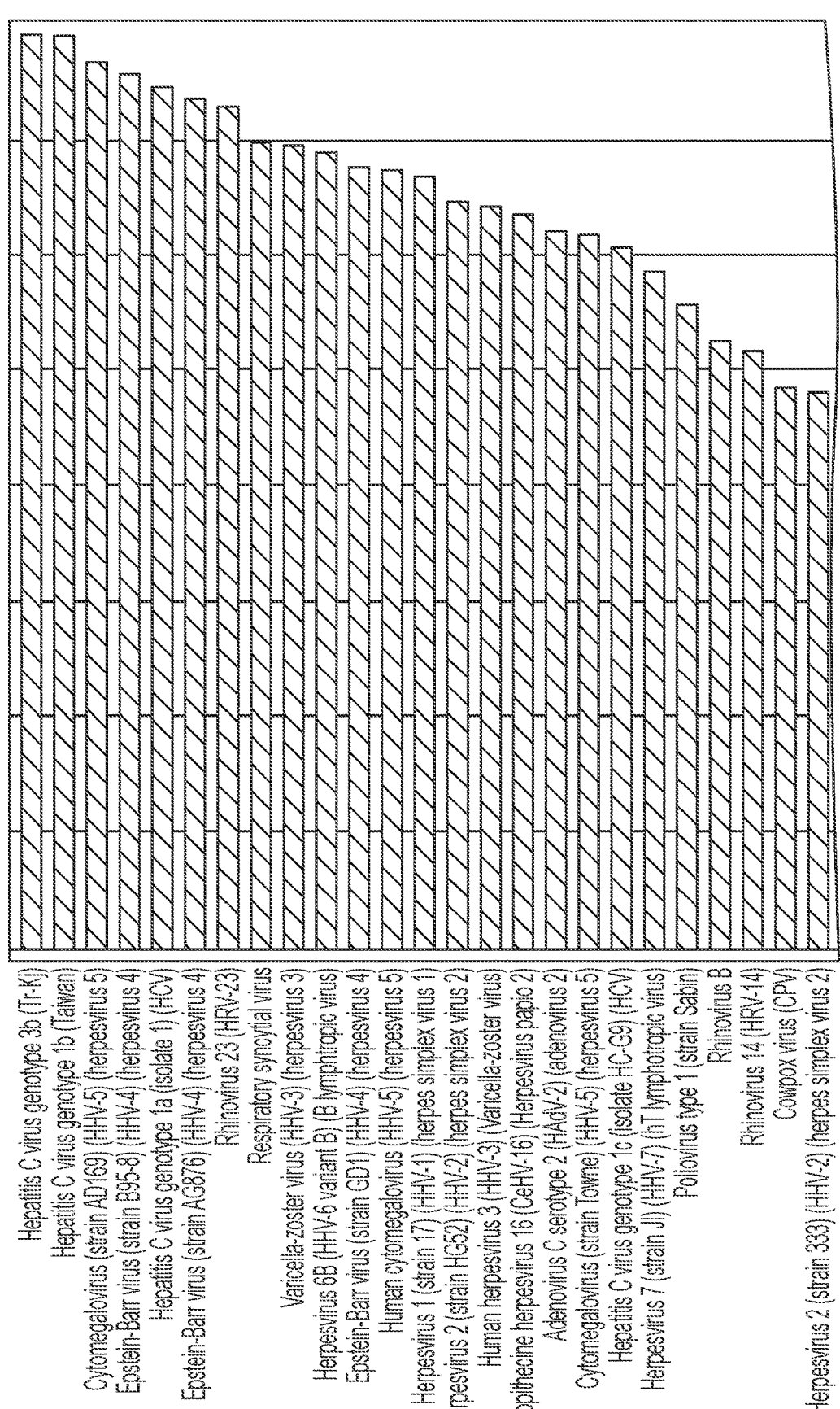
Figure 11H:
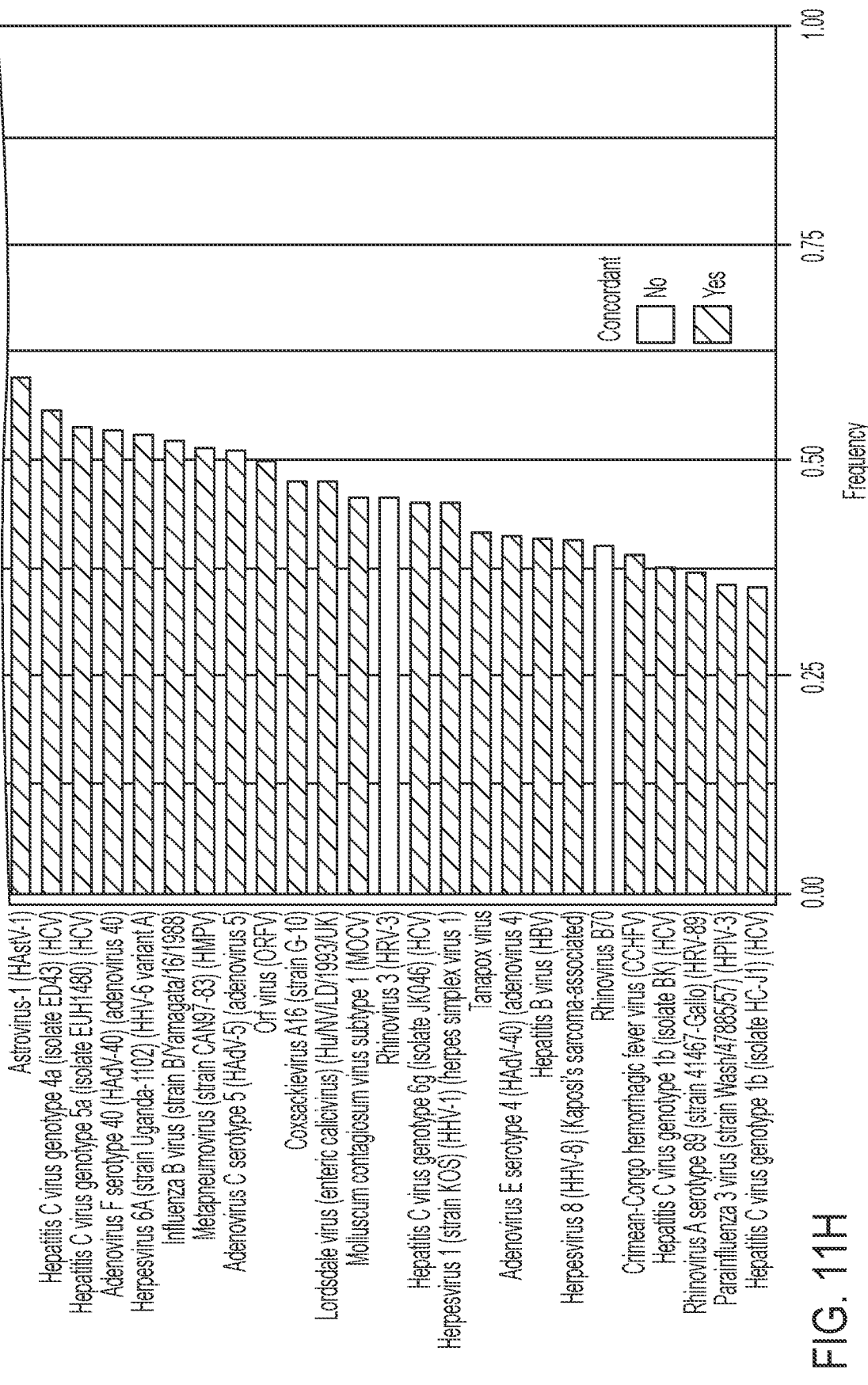
Figure 11I:
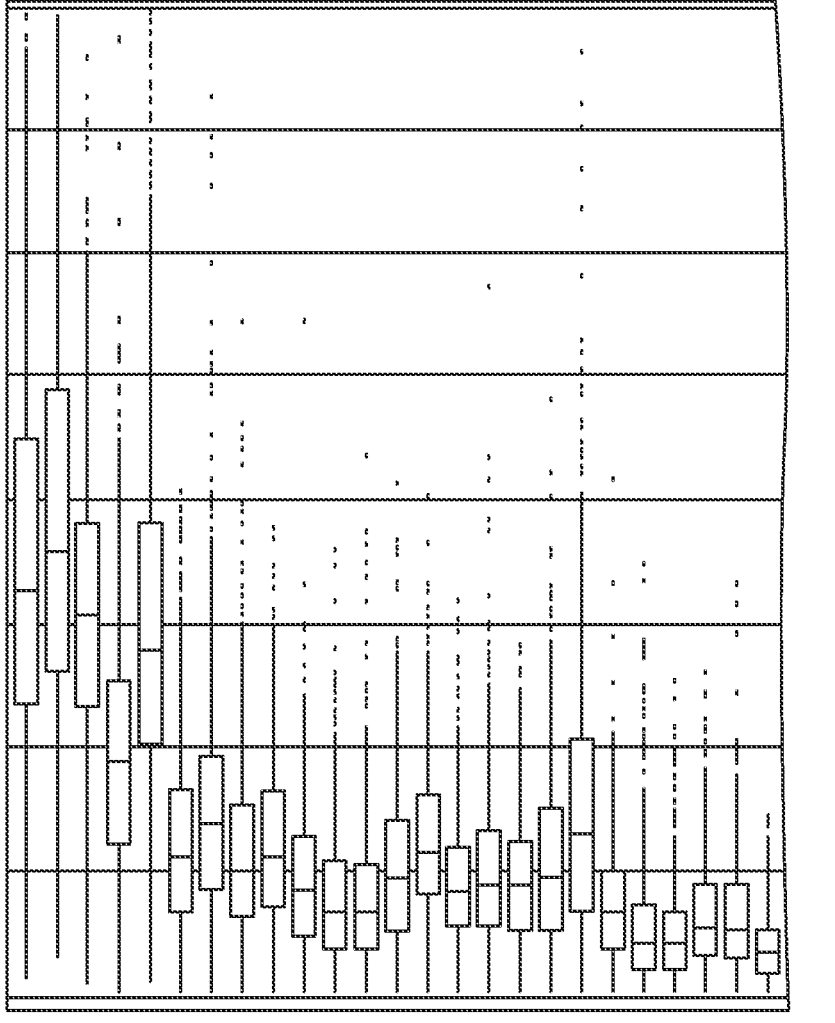
Figure 11J:
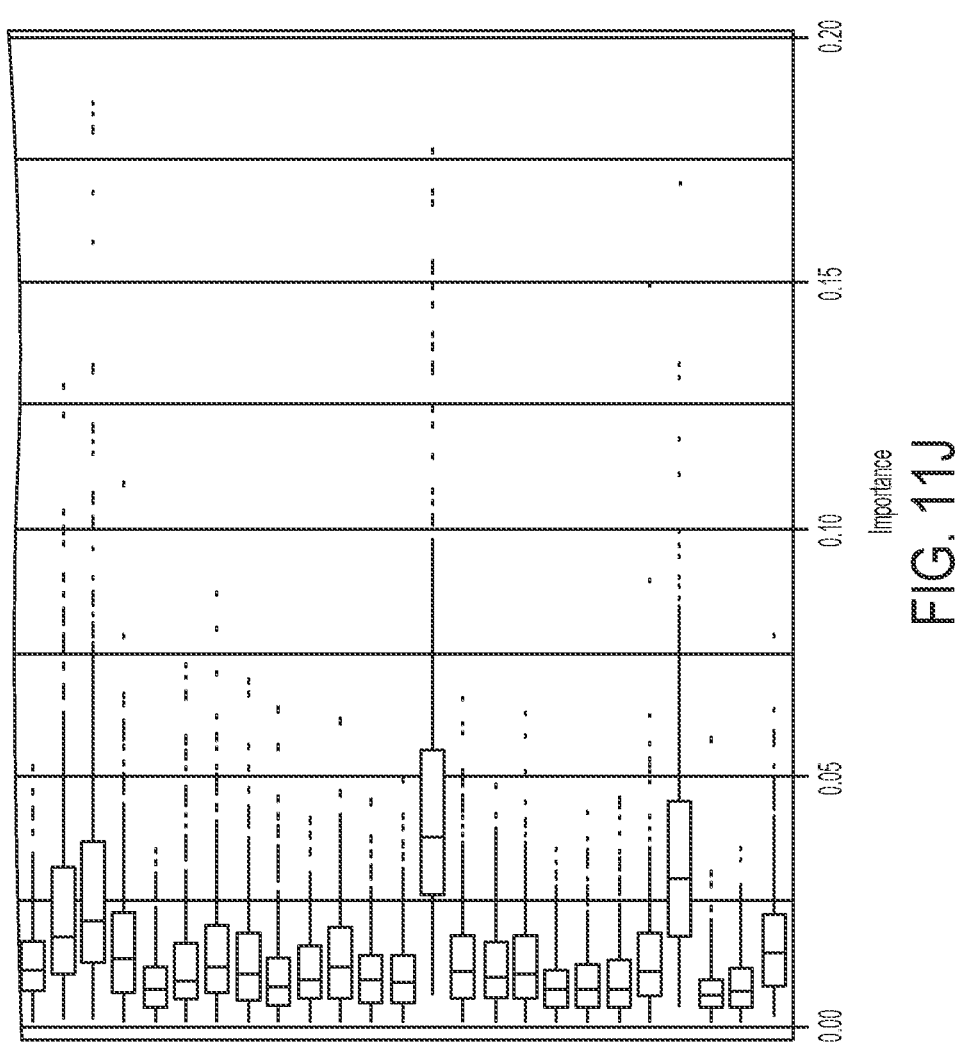

A phylogenetic analysis of the reactive epitopes of the 61 viral strains was performed to determine similarity among these HCC-related viruses (FIGS. 3E-3F). To search common reactive viral epitopes either enriched or depleted in HCC, viral epitopes that rank at the top for their association with HCC were restricted. These viruses can be divided into eight main branches where different HCV epitopes are clustered together with other viral epitopes, with an exception of cluster #6, which contains six HCV variants (out of 12 viruses) (FIGS. 3E-3F; Table 5B). In general, there was no clear enrichment within each branch for increased or decreased viruses, suggesting that varying viral epitopes involved in immunoreactivity are commonly shared among HCC. Since a majority of HCC patients have evidence of CLDs, to avoid this confounding variable, AR was also compared to HCC using the same gradient-boosting approach. It was found that an AR versus HCC VES can significantly discriminate HCC from AR or PC with AUC values similar to VES for training and cross validation (FIGS. 11A-11B). A majority of these VES-related viral strains overlap (FIG. 11C). To further test the robustness of VES, a 60/40 split was performed where 60% of cases were used for VES discovery while the remaining 40% of cases were used for an independent prediction. In total, 1,000 permutations of the split were performed to establish the confidence interval (CI). Again, similar VES was found with a mean of AUC 0.7 for prediction (FIGS. 11D-11J).

Figure 6B:
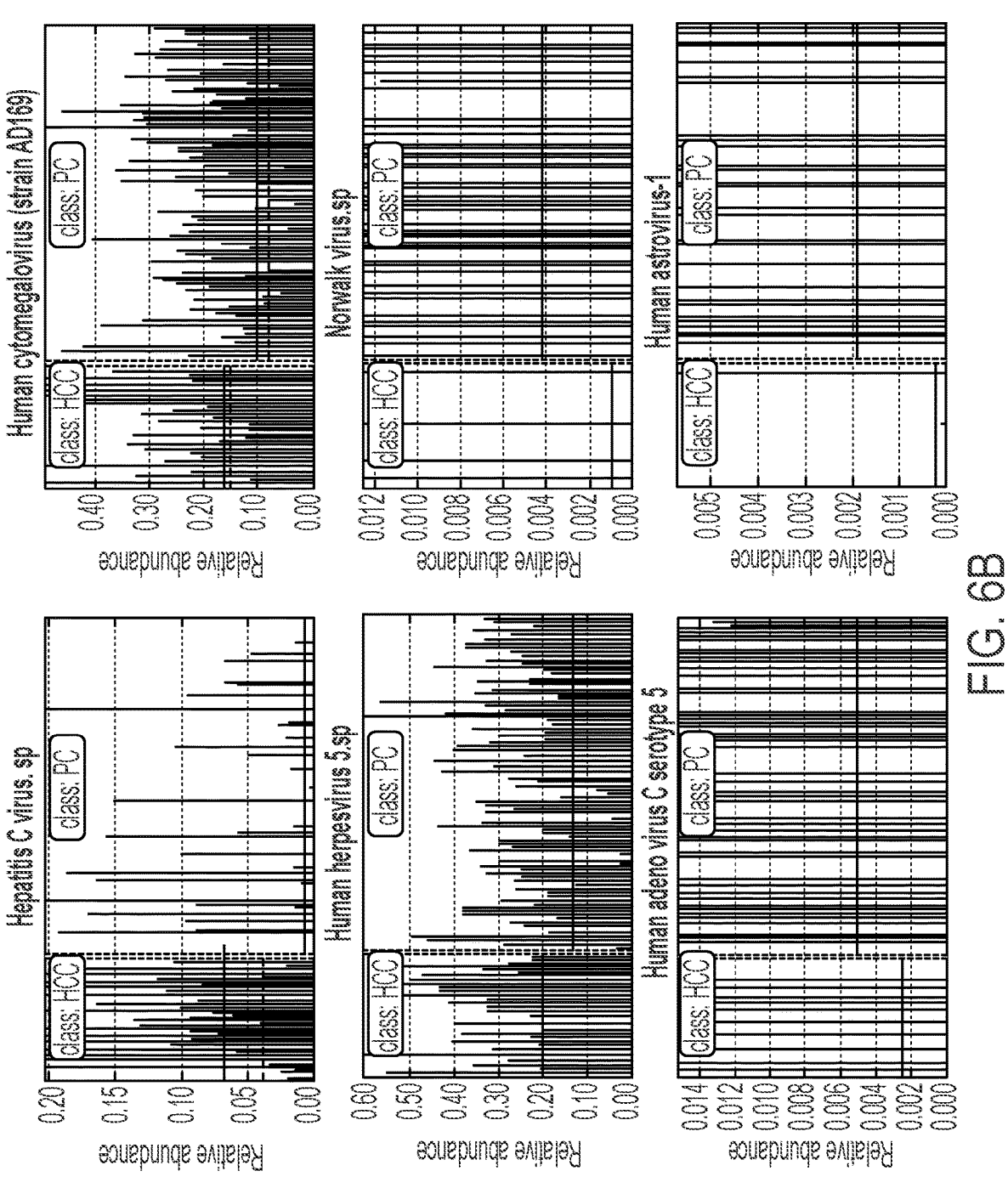

Another statistically conserved method, the linear discriminant analysis of effect size (LEfSe, or LDA) (Segata et al., Genome Biol 2011; 12:R60), was used to search for HCC associated viruses. Furthermore, pairwise comparisons were performed for viral taxa at all levels including DNA/RNA viruses, viral families, viral species and viral strains between HCC and PC. In addition to VES at the strain level, this analysis also identified the viral taxonomic differences by viral families, such as Flaviviridae of positive single-strand RNA viruses, Pneumoviridae of negative single-strand RNA viruses and Circoviridae of single-strand DNA viruses. These analyses resulted in 341 viruses that can significantly distinguish HCC from PC. Among them, several HCV variants, herpesvirus 5 variants, Norwalk virus variants, cytomegalovirus, adenovirus variant and astrovirus-1 were uniquely different between PC and HCC (FIG. 6B). A total of 31 viruses were overlapping between Xgboost and LEfSe (Table 6) and were different between PC and HCC. Unsupervised hierarchical clustering of the abundances of the top-ranking viruses revealed that HCC were more closely related to HR than PC, consistent with the VES prediction score (FIG. 6A, FIG. 3D). Collectively, these results indicate that a unique set of VES is robust in defining HCC.

Validation of the VES in HCC

Figure 7B:
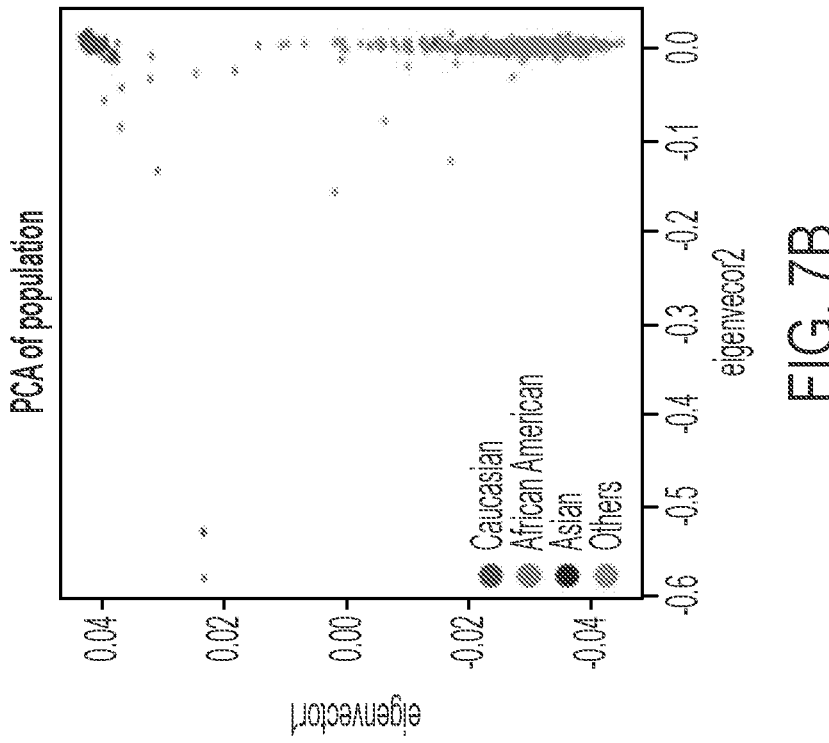
FIGS. 7A-7C: Quality control of the GWAS study.
Figure 7A:
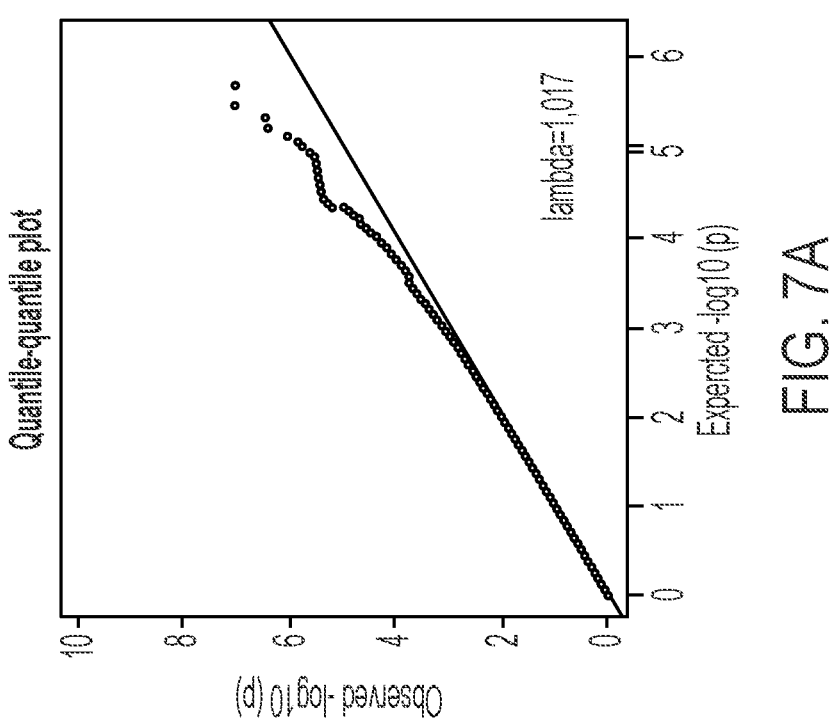
Figure 7C:
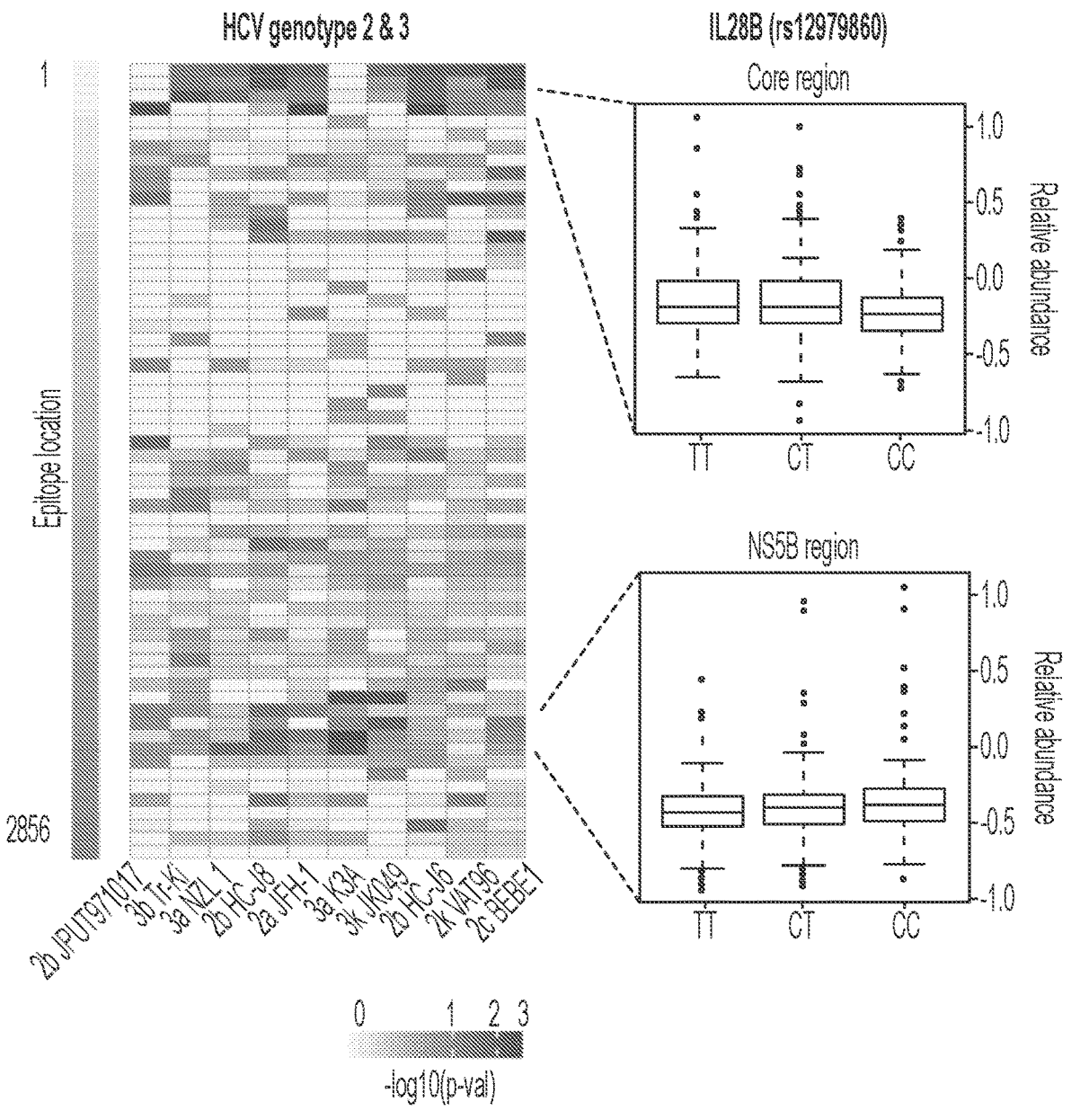

To further validate the two VES identified above for their clinical utility, VirScan profiles in the at-risk NIDDK cohort for HCC was analyzed. This cohort consisted of 173 CLD patients (NIDDK-HR) who were enrolled for a natural history study for liver disease with a follow-up of up to 20 years (Table 1; FIG. 8A). Among them, 44 individuals developed HCC. This cohort contained serum samples collected at enrollment (baseline) and at various follow-up time points until a diagnosis of HCC (diagnosis). Logistic regression analysis was performed using the VES from either all 61 viruses (FIG. 4) or the overlapping 31 viruses (FIG. 7) and receiver-operating characteristic (ROC) curves were generated corresponding to the Maryland cohort or the NIDDK-HR cohort, respectively. The areas under the curve (AUC) were 0.89, 95% CI (0.86-0.92) for 61-VES (FIG. 4A) and 0.85, 95% CI (0.81-0.88) for 31-VES in the Maryland cohort (FIG. 7A). It was observed that levels of 61-VES scores varied among HCC cases in the Maryland cohort with some having below the detection limit and others having either low or high levels (FIG. 4B). Patients with a high level had a significantly worse survival compared to patients with a low level or below the detection limit (log rank p=0.026, and p-trend=0.033) (FIG. 4C). Similar results were observed with the 31-VES. Among patients from the NIDDK cohort, VirScan data were available for 40 HCC cases at baseline, 129 controls at baseline, 44 HCC cases at diagnosis and 106 controls at diagnosis (n=106). The average number of viral species in each case of NIDDK cohort were 6.

Figures 4D, 4E, 4F:
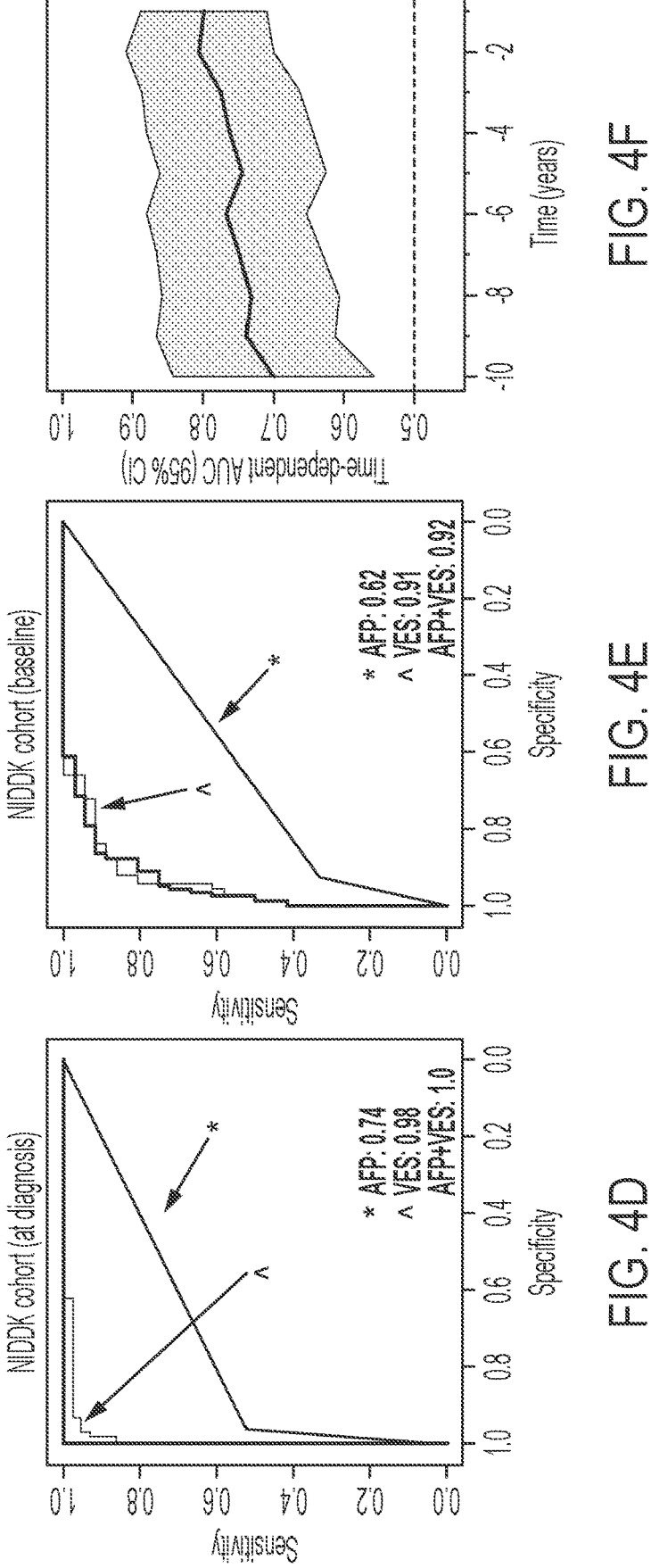
Figure 4G:
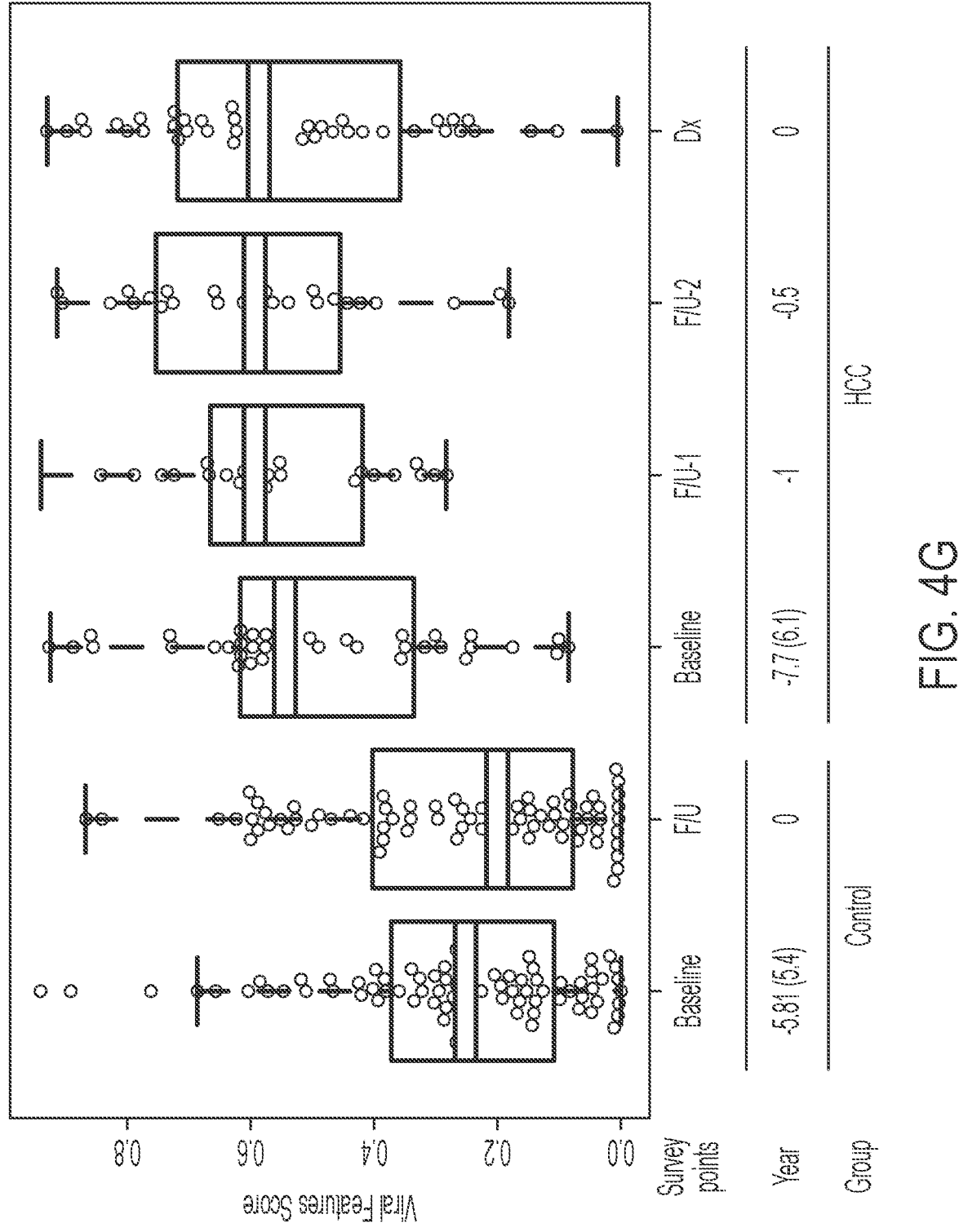
Figure 4H:
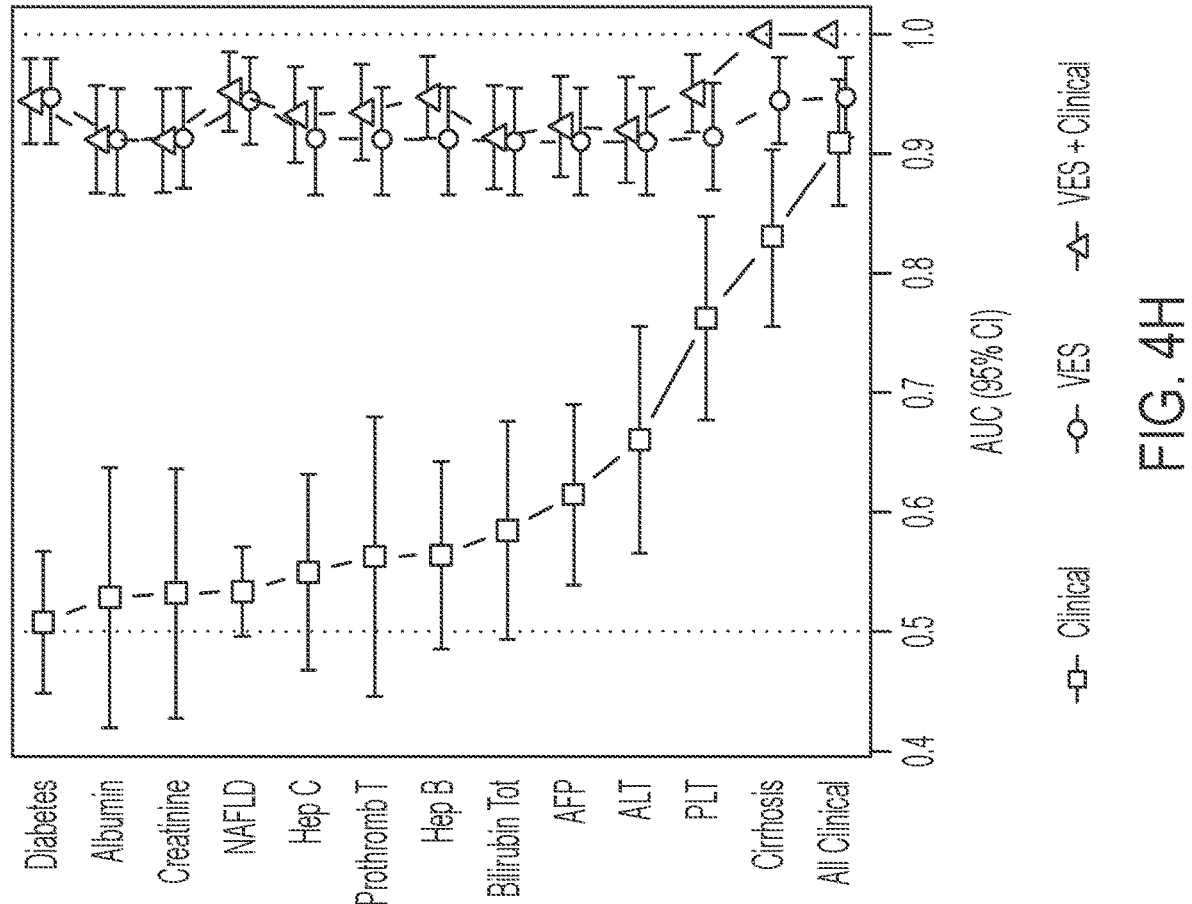
Figures 8B, 8C:
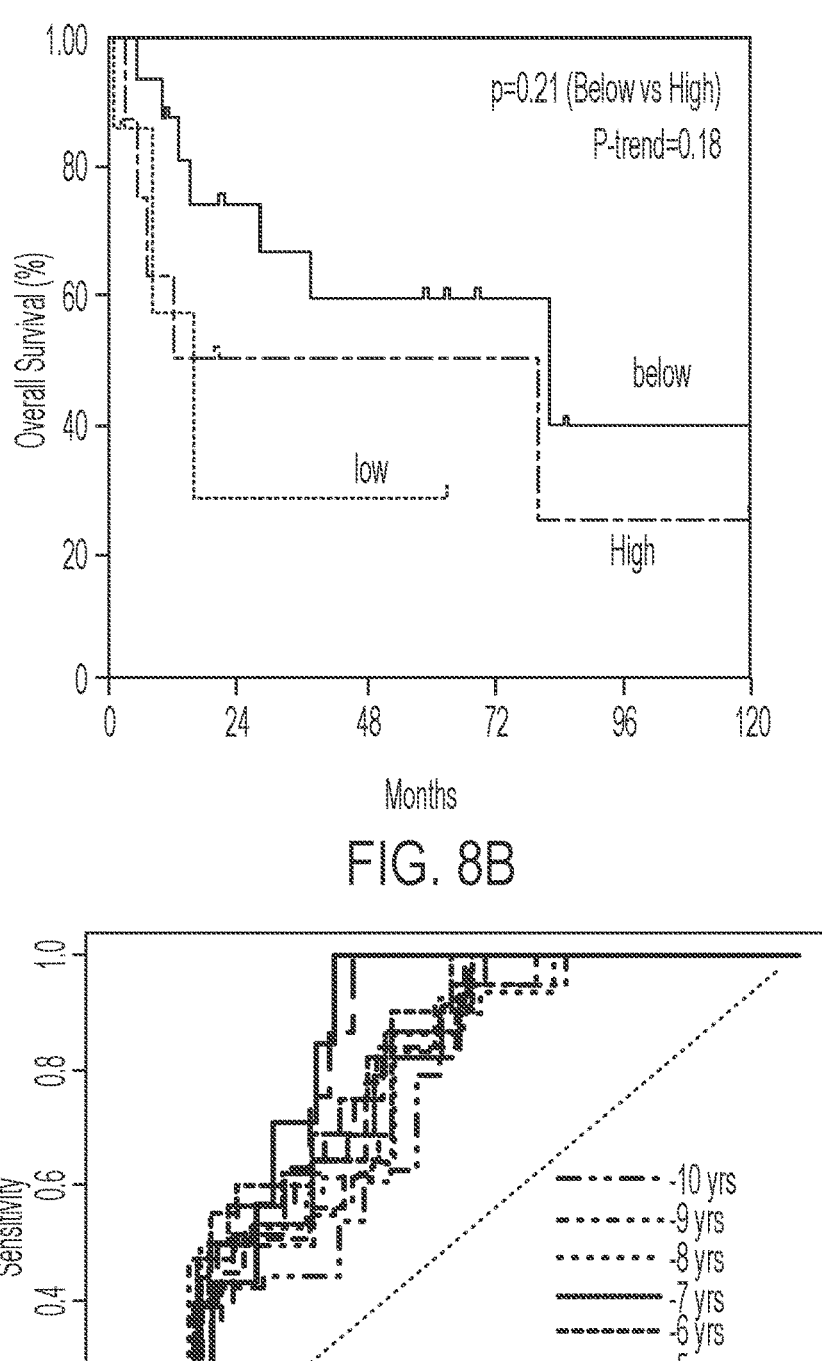
Figure 8E:
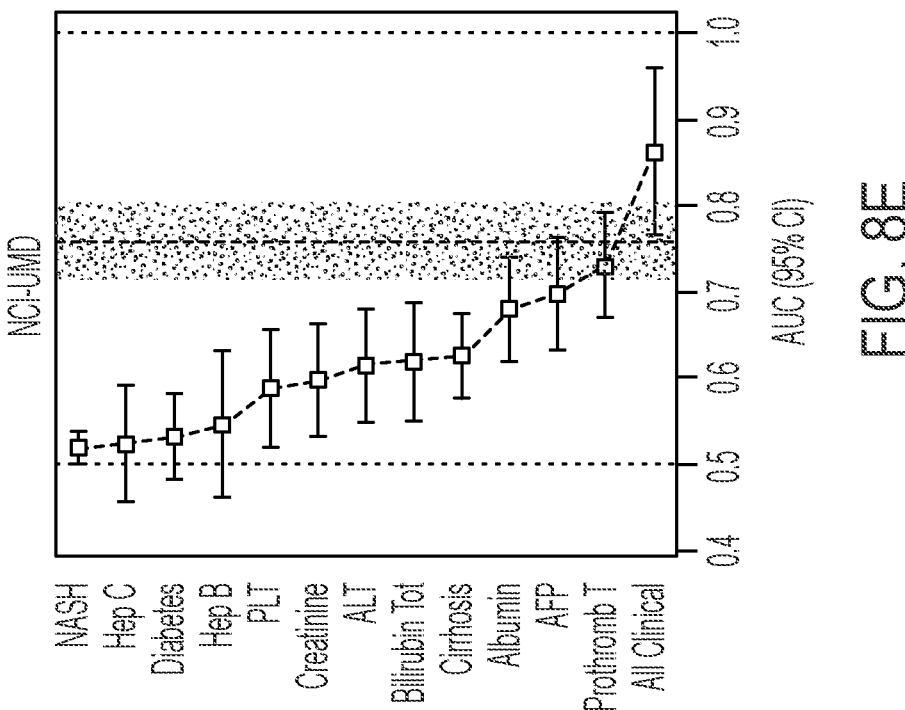
Figure 8D:
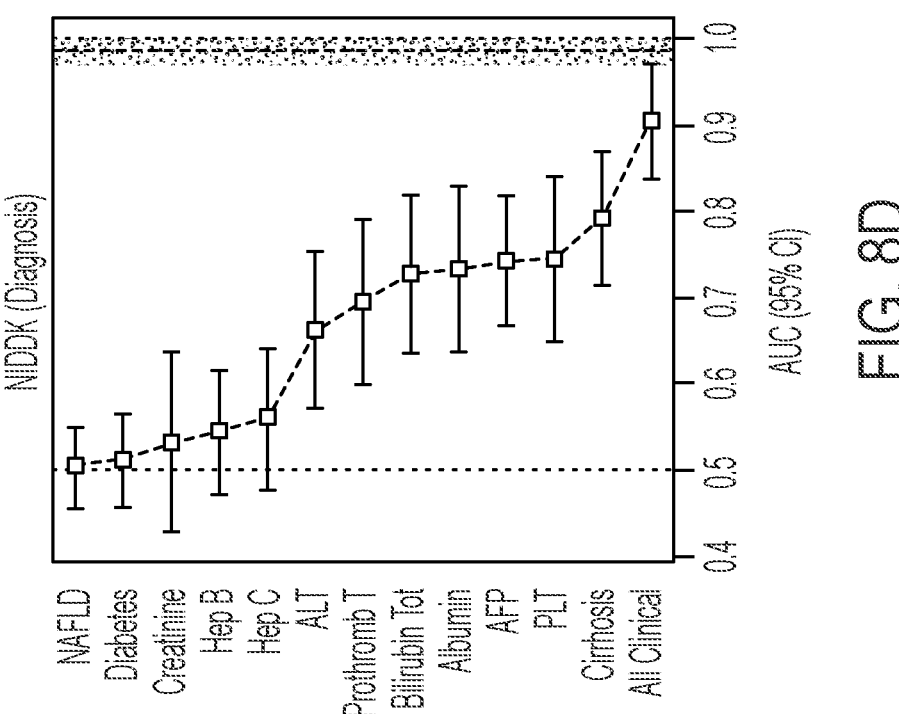

Table 9A shows the results from univariable and multivariable Cox model survival analysis on several clinicopathologic variables to clarify the independent and additional prognostic value of VES. Among patients from the NIDDK cohort, VirScan data were available for 40 HCC cases at baseline, 129 controls at baseline, 44 HCC cases at diagnosis and 106 controls at diagnosis. It was found that the AUC values were 0.98, 95% CI (0.97-1.00) at diagnosis (FIG. 4D) and 0.91, 95% CI (0.87-0.96) at baseline (FIG. 4E) with 61-VES. Similar results were obtained with 31-VES. The performance of the VES was superior to alpha-fetoprotein (AFP), a known HCC diagnostic marker used in the clinic. The 31-VES yielded AUC values of 0.92, 95% CI (0.87-0.97) and 0.81, 95% CI (0.74-0.89) at diagnosis and at baseline, respectively, when combined with AFP. The DeLong test showed a significant improvement between VES and AFP (p values $4\times10^{-12}$ and $8\times10^{-10}$ at baseline and diagnosis, respectively) (FIGS. 4D and 4E). Similar trends (p-trend=0.19) were also found between the levels of VES and overall survival among 44 patients in the NIDDK cohort (FIG. 8B). In order to assess the time-dependent performance of VES to predict the onset of HCC, 104 cancer-free controls and 40 HCC cases (from the NIDDK validation cohort) for which at least two time points were available were analyzed. In the context of survival modeling, an event was defined as the occurrence of an HCC diagnosis. Under this interpretation, censoring time was defined as the time difference between baseline and follow-up within the cancer-free control group, whereas event time was defined as the time difference between baseline and HCC diagnosis within the HCC group. Table 9B shows results from a multivariable Cox regression model generated to predict the occurrence of HCC diagnosis based on VES scores at baseline, adjusted for clinical prognostic variables. Moreover, a time-dependent ROC curve analysis (Bansal and Heagerty, Diagn Progn Res 3:14, 2019; Blanche et al., Stat Med 32: 5381-5397, 2013) was performed to assess the performance of VES over a range of landmark time points from 1 to 10 years relative to baseline (FIGS. 4F and 8C), which appears very robust and stable across this range. It was found that patients who developed HCC had, on average, much higher VES scores at baseline and at different times of follow-up until HCC diagnosis, when compared to cancer-free at-risk patients who were followed up at a similar time interval without developing HCC (FIG. 4G). A statistically significant increase in viral exposures (p<0.05) was observed only for patients who developed HCC over time during the surveillance period in the NIDDK cohort. It appears that HCC cases with a high viral exposure had a more aggressive disease than those with a low viral exposure, and that VES was a robust indicator of early onset of HCC in this prospective cohort. Furthermore, the prediction performance of AR versus HCC based on VES was superior to other clinical indicators from the patient charts, such as AFP, alanine transaminase (ALT), cirrhosis and platelet counts, as well as the combination of all key clinical variables, as shown by analyses of the NIDDK cohort at baseline (FIG. 4H), which agree qualitatively with those of NIDDK at diagnosis (FIG. 8D) and the NCI-UMD cohort (FIG. 8E). An association of VES and HCC was similarly found in both HCV-positive and HCV-negative patients (Table 9C).

TABLE 1

Clinical Characteristics of the Patients*

| Variable | Without HCC (N = 129) | With HCC (N = 44) | P Value |
|---|---|---|---|
| Age-year | | | 0.12 |
| Median (Range) | 51 (23-79) | 54 (23-79) | |
| Missing data | 1 | 0 | |
| Sex-no. (%) | | | |
| Female | 40 (31.0) | 14 (31.8) | 1.00 |
| Male | 89 (69.0) | 30 (68.2) | |
| Missing data | 0 | 0 | |
| Race-no. (%) | | | 0.69 |
| European American | 63 (48.8) | 22 (50.0) | |
| African American | 29 (22.5) | 12 (27.3) | |
| Asian American | 26 (20.2) | 8 (18.2) | |
| Other | 2 (1.6) | 0 | |
| Missing data | 9 (7.0) | 2 (4.6) | |
| HCV only-no. (%) | 98 (76.0) | 27 (61.4) | 0.61 |
| HBV only-no. (%) | 18 (14.0) | 7 (15.9) | |
| HBV + HCV-no. | 2 (1.6) | 1 (2.3) | |
| HBV + HDV-no. | 4 (3.1) | 3 (6.8) | |
| Others not hepatitis | 7 (5.4) | 6 (13.6) | |
| Cirrhosis-no. (%) | 15 (11.6) | 28 (63.6) | <0.001 |
| Missing data | 2 (1.6) | 4 (9.1) | |
| Alanine aminotransferase-no. (%) | | | <0.01 |
| Elevated (>50 U/L) | 84 (65.1) | 28 (63.6) | |
| Normal (≤50 U/L) | 45 (34.9) | 16 (36.4) | |
| Alpha-fetoprotein-no. (%) | | | <0.001 |
| >20 ng/mL | 9 (7.0) | 21 (47.7) | |
| ≤20 ng/mL | 120 (93.0) | 23 (52.3) | |
| Missing data | 0 | 0 | |
| Survival (months) | | | |
| Median | NA | 15.2 | |
| Range | NA | 0.07-131.8 | |
| Missing data (%) | NA | 1 (2.3) | |

*The clinical characteristics of the 173 at-risk patients in the prospective NIDDK cohort.

Phenotype-Genotype Association with VES

To determine if host genetic background may be linked to VES, a genome-wide association study (GWAS) in the Maryland cohort was performed, as this approach may help identifying susceptibility variants related to viral infection and cancer (McKay J et al., Nat Genet 2017; 49:1126-1132; Pharoah et al., Nat Genet 2013; 45:362-370; Fumagalli et al., PLoS Genet 2010; 6:e1000849). After assessment using the genetic quality control measures, 849 participants (PC, n=402; HR, n=323; HCC, n=124) were included in the analysis. Following the removal of monoallelic SNPs and the ones that deviate away from Hardy-Weinberg equilibrium, an association test was performed for all the remaining SNPs. To further assess the quality of the GWAS data, it was determined whether there was an association between an SNP, rs12979860 in IL28B, and HCV infection. As its favorable genotype, CC has been shown to be associated with better HCV treatment response or natural clearance. It was found that rs12979860-CC was significantly associated with HCV genotype 3 with odds ratio (OR) 2.74 (95% CI 1.14-7.97) in a dominant model manner (Table 3A). Furthermore, the SNP associated with 375 epitopes abundances of HCV genotype 2 and 3 was evaluated. The CC allele was found to be associated with a decreased abundance of core epitopes but an increased abundance of NS5B epitopes in the HCV genome (FIG. 7C; Table 3B), consistent with a recent study (Ansari et al., *Nat Genet* 49:666-673, 2017). To assess VES-associated SNPs, HCC and PC groups were combined and then divided into two groups based on dichotomization of VES scores. In the associated quantile-quantile plots (FIG. 8B), a wider spread with small differences in allele frequencies was evident with increased slope of the line. Principal-component analysis based on genotyping revealed differences in ethnicity (FIG. 7B).

Figure 9A:
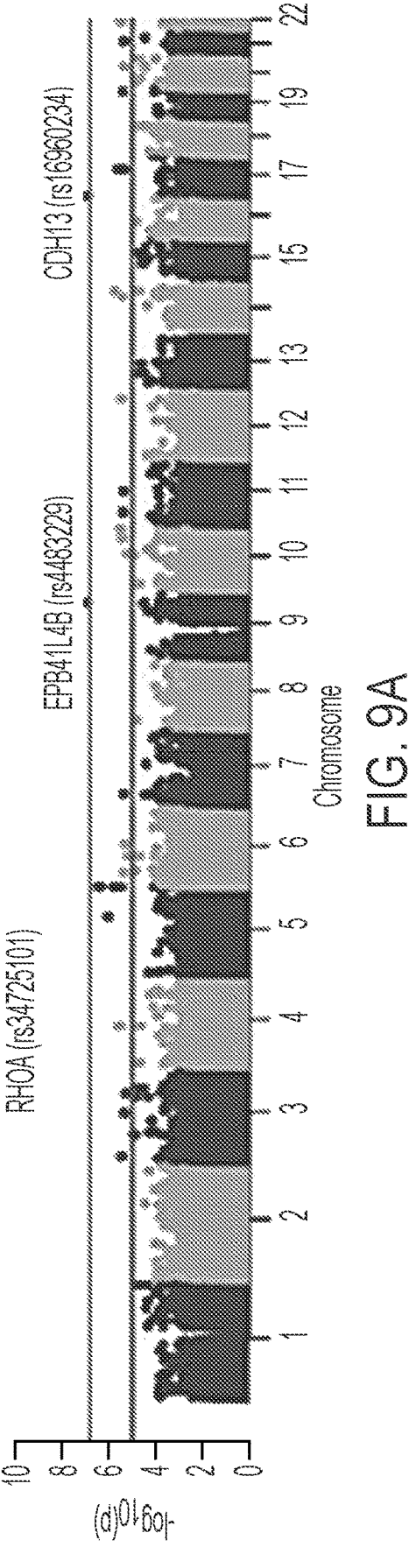
FIGS. 9A-9G: Genome-wide scan identifies specific genetic variants linked to VES.
Figures 9B, 9C:
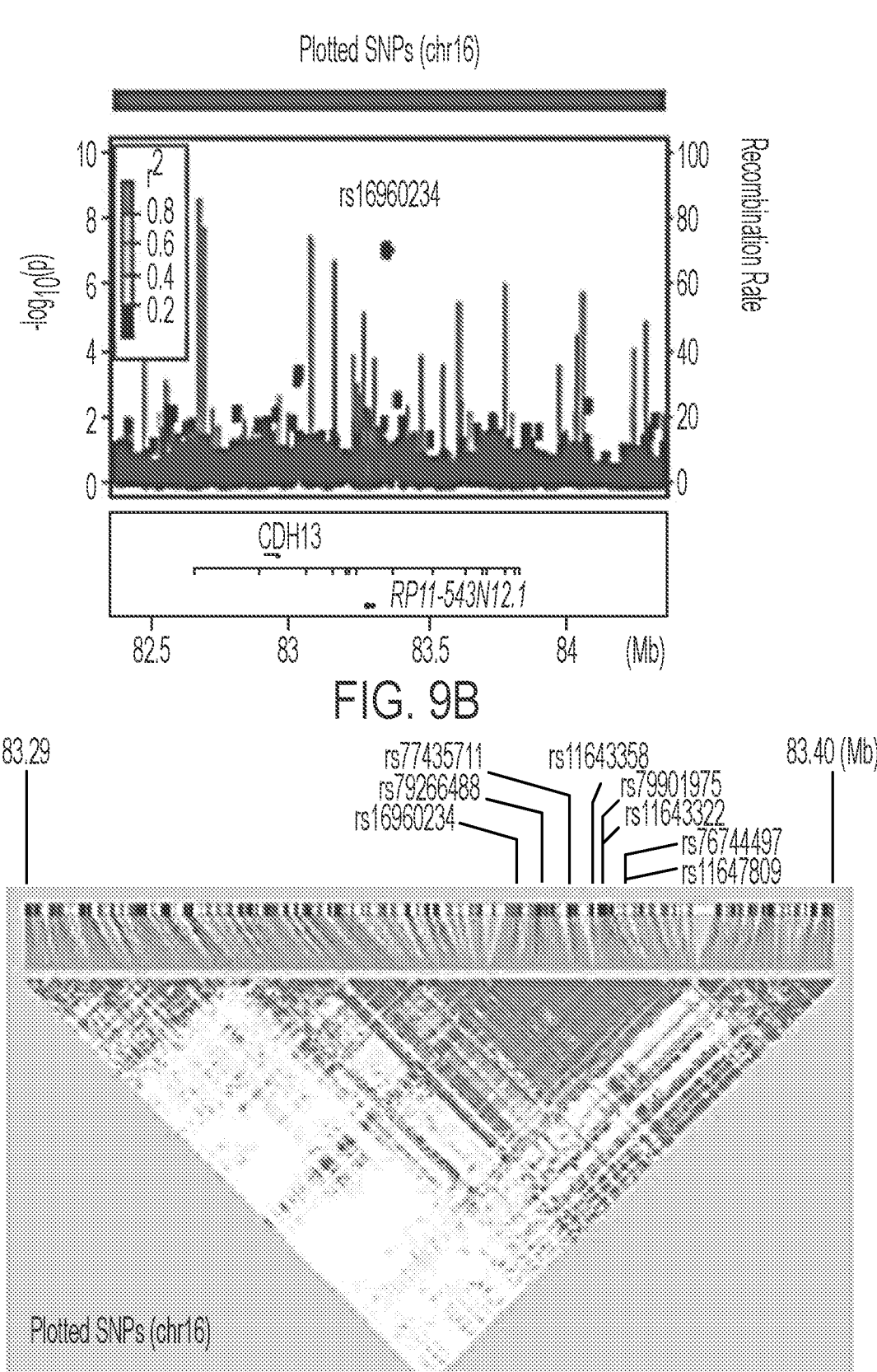
Figures 9D, 9E, 9F:
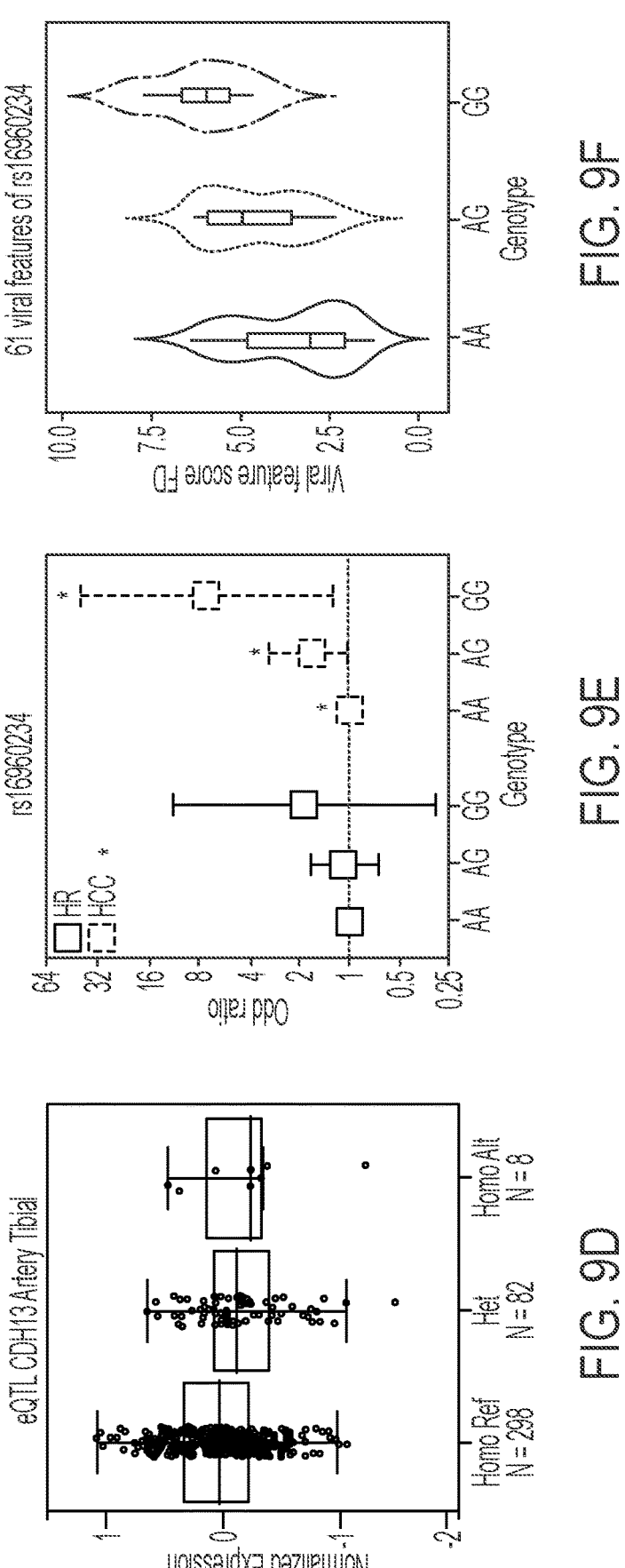
Figure 9G:
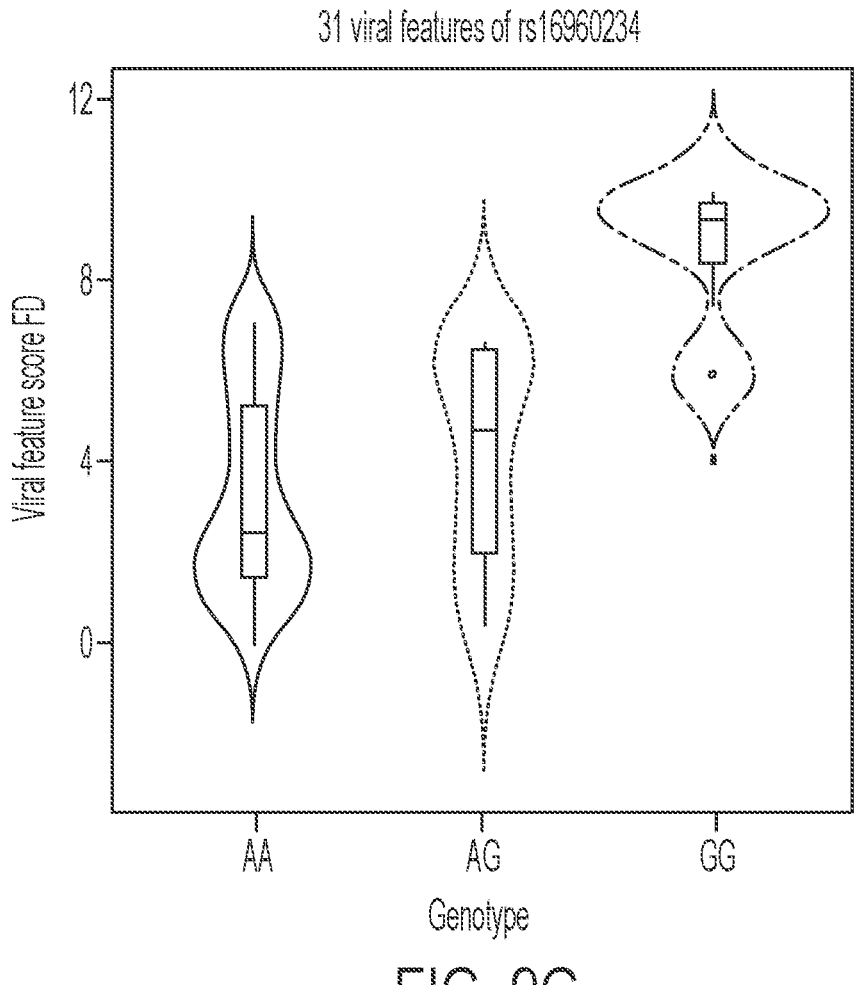

Manhattan plot analysis revealed several SNPs with much larger differences between high and low VES scores having the p-values $<10^{-5}$ (FIG. 9A). Three SNPs, rs34725101, rs4483229, and rs16960234, in three different genomic regions corresponding to RHOA, EPB41L4B and CDH13, respectively, had the p-values <10-7, an acceptable standard for common-variant GWAS, to be linked to VES (Table 3C and FIG. 9A). Among them, rs16960234 was further analyzed because both major and minor alleles of this variant could be detected in this cohort. High linkage disequilibrium (LD) SNPs ($r2>0.6$) were also found for rs16960234, but not rs34725101 and rs4483229 (FIGS. 9B-9C; Table 7). Seven of the high LD SNPs of rs16960234 showed the expression profile of CDH13 as expression quantitative trait loci (eQTL) in genotype-tissue expression (GTEx) database (McKay J et al., Nat Genet 2017; 49:1126-1132). The CDH13 expression levels in the artery tibial tissues from the carriers with risk/protective G/G genotype of rs16960234 were significantly higher than the carriers with protective/risk genotype A/A (FIG. 9D). To obtain the genotypic effects of rs16960234 in HCC or HR, logistic regression was constructed and the genotypic odds ratio of this SNP in HR or HCC was calculated and compared to PC (FIG. 9E). rs16960234 genotyping G/G showed significant increase risk in HR vs. PC, OR; 1.89 (0.30-11.4) and risk was even higher in HCC vs. PC, OR: 7.22 (1.30-40.0) (FIG. 9E; Table 4). Consistent with genotypic effect in HCC, the VES score also showed gradual increases in heterogeneous A/G and G/G compared with A/A (FIGS. 9F-9G). Thus, rs16960234 and its linked gene CDH13 may be associated with VES and contributed to the disease risk.

Diagnostic Applications

Detecting cancer at an early stage preferably before it is symptomatic may provide an opportunity in achieving a cure and improving outcomes on cancer-related mortality. Evidence suggests that earlier detection of cancer improves survival for some cancer types, such as cervical and colon cancers. A conventional approach is to develop biomarkers specific for cancer cells to aid in early cancer diagnosis. CancerSEEK is an emerging platform successful in achieving a good sensitivity and specificity to clinically-detected multiple cancer types by profiling circulating cell-free DNA (ctDNA) presumably shed from tumor cells (Cohen et al., Science 2018; 359:926-930). A recent study offers a cautionary note for measuring cancer gene panels using ctDNA because of its high false positivity among healthy individuals (Liu et al., Ann Oncol 2019; 30:464-470). Molecular and biological heterogeneity of cancer cells contributed by complex etiological landscape creates a dilemma as how best to design cancer-specific diagnostic panels effective for early cancer detection. As such, a continuous debate has been carried out in recent decades for many malignant diseases including HCC as whether available methods are adequate in achieving this goal (Sherman et al., Hepatology 2012; 56:793-796; Shieh et al., Nat Rev Clin Oncol 2016; 13:550-56).

HCC is a unique malignancy for which most major causative etiologies are known (Wang and Thorrgeirsson, Oncology 2014; 1:5). However, defining biomarkers specific for HCC cells has been challenging because of its complex genomic landscape with extensive intratumor and intertumor heterogeneities. Are there common features shared among HCC patients to be used as a surrogate for early detection? An emerging concept is that an interplay between viral infection and host genetic background is crucial for maintaining virome homeostasis or causing human disease (Virgin, Cell 2014; 157:142-150). The study disclosed herein assessed how a history of viral exposures by an individual is associated with their risk of developing HCC. Using a synthetic viral scan technology (VirScan) with a simple blood test (Xu et al., Science 2015; 348:aaa0698), a VES was identified that could discriminate HCC with a high confidence from individuals with chronic liver diseases or from healthy volunteers. Remarkably, this signature was able to identify individuals at a medium follow-up year of 8.8 prior to a clinical diagnosis of HCC. Thus, these results offer a sensitive tool applicable to the HCC surveillance program to improve early diagnosis.

The current study took the advantage of a simple tool to profile serological samples to link an individual's history of viral infection and corresponding response to early onset HCC. The strategy was first to search VES using a case control design that include HCC cases as well as at-risk individuals with chronic liver diseases and healthy volunteers matched by age and sex. A VES that can discriminate HCC from at-risk and healthy individuals was then validated using a prospective cohort of sequentially enrolled at-risk patients who were followed up for the development of HCC. The VES consists of known HCC etiologies such as HCV, HBV and HDV, but also includes other viruses such as herpesviruses 4 and 5, Crimean-Congo hemorrhagic fever virus, cytomegalovirus, and influenza A virus, among others. A few features are noted. First, HCV appears to be a major etiology driving VES but an extended heterogeneity in various HCV subtypes are noted in both Maryland and NIDDK cohorts. Second, a set of viruses are enriched while many others including HBV are depleted in HCC patients.

The current method of VirScan is based on the phage immunoprecipitation sequencing (PhIP-Seq) technology that provides a powerful approach for analyzing antibody-repertoire binding specificities with high throughput and at low cost to all known human viruses (Mohan et al., Nat Protoc 2018; 13:1958-1978). Comparing VirScan results with HCV and HBV status from medical chart of the UMD cohort, it was found that VirScan shows great specificity for both HCV and HBV, and good sensitivity for HCV but to a lesser extent for HBV. HCV encodes a large polyprotein consisting of ~3,000 amino acids, which is cleaved co- and post-translationally into ten different proteins associated with intracellular membranes (Bartenschlager et al., Nat Rev Microbiol 2013; 11:482-496). Consistently, HCV antigen reactivity largely overlapped with the predicted antigenicity score by the B-cell epitope prediction method coinciding with peptides to be presented at the surface of the cellular membrane. Consistent with early reports for the likelihood of coinfection of HIV and other viruses associated with AIDS and non-AIDS diseases (Xu et al., Science 2015; 348:aaa0698; Slyker et al., J Infect Dis 2013; 207:1798-1806; Lichtner et al., J Infect Dis 2015; 211:178-186), evidence of coinfection between HIV and viruses such as HBV, herpesvirus 8 and adenovirus D, influenza B virus, adenovirus C, and herpesvirus 5 was found in patients enrolled in the Maryland cohort. History of HCV infection is prevalent among at-risk (48%), HCC patients (39%) and healthy volunteers (4%) who reside in Maryland. This is in contrast to an estimated prevalence of about 4.6 million persons (~1.5%) infected with HCV in the U.S. (Edlin et al., Hepatology 2015; 62:1353-1363). It should be noted that 7.5%-44% of incarcerated individuals and 4%-38% of hospitalized patients tested positive for HCV (Edlin et al., Hepatology 2015; 62:1353-1363), suggesting that the current surveys underestimate the prevalence of HCV infection. In contrast, while 2.6% of the Maryland healthy individuals showed evidence of HBV infection, more than 800,000 chronic HBV carriers were detected during 2011-2012 in the noninstitutionalized U.S. population (Roberts et al., Hepatology 2016; 63:388-397). The current survey methods may underestimate the prevalence of HBV and HCV. This is important as both HBV and HCV are major causative factors for HCC. Collectively, VirScan is a reliable method for profiling viral exposure and is scalable regarding to sample throughput and relatively low cost per analysis amenable for surveillance and early detection of HCC.

TABLE 2A

| Viral Frequency in 899 patients and volunteers from NCI-UMD cohort | | | | |
|---|---|---|---|
| Viral Species | Total (N = 899) | PC (N = 412) | HR (N = 337) | HCC (N = 150) |
| Human herpesvirus 4 | 97.00% | 97.82% | 96.74% | 95.33% |
| Human herpesvirus 5 | 67.30% | 60.92% | 72.11% | 74.00% |
| Human herpesvirus 1 | 62.85% | 60.44% | 65.58% | 63.33% |
| Human respiratory syncytial virus | 50.06% | 55.10% | 45.70% | 46.00% |
| Influenza A virus | 48.16% | 50.00% | 48.07% | 43.33% |
| Human adenovirus C | 41.60% | 46.36% | 35.91% | 41.33% |
| Human herpesvirus 6B | 37.82% | 43.93% | 32.64% | 32.67% |
| Human herpesvirus 3 | 32.59% | 37.86% | 27.00% | 30.67% |
| Human herpesvirus 2 | 30.59% | 31.55% | 31.16% | 26.67% |
| Influenza B virus | 27.47% | 30.10% | 27.30% | 20.67% |
| Hepatitis C virus | 26.36% | 3.64% | 48.37% | 39.33% |
| Rhinovirus A | 22.80% | 27.91% | 19.88% | 15.33% |
| Rhinovirus B | 20.47% | 23.06% | 18.99% | 16.67% |
| Human herpesvirus 7 | 12.35% | 15.53% | 10.09% | 8.67% |
| Enterovirus C | 10.79% | 11.65% | 11.57% | 6.67% |
| Human adenovirus B | 8.23% | 8.01% | 9.50% | 6.00% |
| Human immunodeficiency virus 1 | 8.01% | 7.28% | 9.79% | 6.00% |
| Human herpesvirus 6A | 6.90% | 8.25% | 5.34% | 6.67% |
| Human adenovirus D | 5.23% | 5.34% | 5.64% | 4.00% |
| Vaccinia virus | 4.89% | 5.83% | 3.26% | 6.00% |
| Human herpesvirus 8 | 4.34% | 4.61% | 3.86% | 4.67% |
| Cowpox virus | 2.78% | 4.37% | 1.78% | 0.67% |
| Papiine herpesvirus 2 | 2.78% | 2.91% | 2.37% | 3.33% |

TABLE 2A-continued

| | Total | PC | HR | HCC |
|---|---|---|---|---|
| Viral Species | (N = 899) | (N = 412) | (N = 337) | (N = 150) |
| Hepatitis B virus | 2.56% | 2.67% | 2.67% | 2.00% |
| Mamastrovirus 1 | 2.45% | 3.40% | 0.89% | 3.33% |
| Human adenovirus F | 2.11% | 2.43% | 1.19% | 3.33% |
| Orf virus | 1.89% | 1.94% | 1.48% | 2.67% |
| Human parainfluenza virus 3 | 1.78% | 2.67% | 0.59% | 2.00% |
| Macacine herpesvirus 1 | 1.78% | 1.70% | 2.37% | 0.67% |
| Molluscum contagiosum virus | 1.67% | 1.94% | 1.48% | 1.33% |
| Human metapneumovirus | 1.56% | 2.18% | 1.19% | 0.67% |
| Human adenovirus A | 1.45% | 0.97% | 2.08% | 1.33% |
| Rotavirus A | 1.45% | 1.70% | 1.48% | 0.67% |
| Torque teno virus | 1.45% | 0.49% | 2.67% | 1.33% |
| Influenza C virus | 1.11% | 1.21% | 0.59% | 2.00% |
| Enterovirus A | 1.00% | 1.46% | 0.89% | 0.00% |
| Norwalk virus | 1.00% | 1.46% | 0.89% | 0.00% |
| Alphapapillomavirus 9 | 0.89% | 0.73% | 1.19% | 0.67% |
| Betapapillomavirus 1 | 0.78% | 0.73% | 1.19% | 0.00% |
| Tanapox virus | 0.78% | 1.21% | 0.59% | 0.00% |
| Aichivirus A | 0.67% | 1.21% | 0.00% | 0.67% |
| Enterovirus B | 0.67% | 0.97% | 0.30% | 0.67% |
| Human coronavirus HKUl | 0.56% | 0.73% | 0.30% | 0.67% |
| Human parainfluenza virus 2 | 0.44% | 0.73% | 0.30% | 0.00% |
| Variola virus | 0.44% | 0.24% | 0.59% | 0.67% |
| Betapapillomavirus 2 | 0.33% | 0.49% | 0.30% | 0.00% |
| Human immunodeficiency virus 2 | 0.33% | 0.49% | 0.30% | 0.00% |
| Ross River virus | 0.33% | 0.49% | 0.30% | 0.00% |
| Venezuelan equine encephalitis virus | 0.33% | 0.24% | 0.30% | 0.67% |
| Betacoronavirus 1 | 0.22% | 0.00% | 0.59% | 0.00% |
| Hepatitis E virus | 0.22% | 0.24% | 0.30% | 0.00% |
| Human adenovirus E | 0.22% | 0.49% | 0.00% | 0.00% |
| Measles virus | 0.22% | 0.24% | 0.00% | 0.67% |
| Rubella virus | 0.22% | 0.00% | 0.30% | 0.67% |
| Yaba monkey tumor virus | 0.22% | 0.24% | 0.30% | 0.00% |
| Alphapapillomavirus 10 | 0.11% | 0.00% | 0.30% | 0.00% |
| Crimean-Congo hemorrhagic fever virus | 0.11% | 0.24% | 0.00% | 0.00% |
| Hendra virus | 0.11% | 0.24% | 0.00% | 0.00% |
| Hepatitis delta virus | 0.11% | 0.00% | 0.30% | 0.00% |
| Human parainfluenza virus 1 | 0.11% | 0.24% | 0.00% | 0.00% |
| Human parainfluenza virus 4 | 0.11% | 0.00% | 0.30% | 0.00% |
| Marburg marburgvirus | 0.11% | 0.24% | 0.00% | 0.00% |
| Primate T-lympho tropic virus 1 | 0.11% | 0.00% | 0.30% | 0.00% |
| Pseudocowpox virus | 0.11% | 0.24% | 0.00% | 0.00% |
| Rotavirus B | 0.11% | 0.00% | 0.30% | 0.00% |

[1]PC: population control
[2]HR: high risk group
[3]HCC: hepatocellular carcinoma

TABLE 2B

Comparison of VirScan with HBV, HCV,
and HIV from medical charts

| Clinical Variable | Virscan Negative | Virscan Positive |
|---|---|---|
| Hepatitis B Virus (HBV) HBV surface antibody | | |
| Negative | 88 | 75 |
| Positive | 48 | 27 |
| Unknown/Missing | 132 | 117 |
| HBV core antibody | | |
| Negative | 80 | 18 |
| Positive | 82 | 10 |
| Unknown/Missing | 250 | 47 |
| Hepatitis C Virus (HCV) HCV IgG antibody | | |
| Not detected | 27 | 34 |
| Detected | 24 | 123 |
| Unknown/Missing | 95 | 184 |

TABLE 2B-continued

Comparison of VirScan with HBV, HCV,
and HIV from medical charts

| Clinical Variable | Virscan Negative | Virscan Positive |
|---|---|---|
| HCV RNA PCR | | |
| Negative | 2 | 2 |
| Positive | 2 | 18 |
| Unknown/Missing | 142 | 321 |
| Human Immunodeficiency Virus (HIV) | | |
| Negative | 268 | 116 |
| Positive | 7 | 19 |
| Unknown/Missing | 58 | 19 |

TABLE 3A

The association between SNP in IL28B gene
(rs12979860) and HCV genotype 2 & genotype 3

| Genotype | NO | YES | OR[a] (95% CI) | P |
|---|---|---|---|---|
| | | | HCV-2 status | |
| TT | 206 | 13 | ref | |
| CT + CC | 575 | 53 | 1.46 (0.77-2.98) | 0.30 |
| | | | HCV-3 status | |
| TT | 213 | 6 | ref | |
| CT + CC | 583 | 45 | 2.74 (1.14-7.97) | 0.020 |

TABLE 3A-continued

The association between SNP in IL28B gene
(rs12979860) and HCV genotype 2 & genotype 3

| Genotype | NO | YES | OR[a] (95% CI) | P |
|---|---|---|---|---|
| | | | HCV-2 & 3 status | |
| TT | 201 | 18 | ref | |
| CT + CC | 539 | 89 | 1.84 (1.07-3.34) | 0.024 |

[a]OR: Odds Ratio

TABLE 3B

SNP in IL28B gene (rs12979860) association with the epitopes of HCV genotype 2 & 3

| HCV genotype 2 & 3 | HCV amino acid position (start to end) | Viral protein | -log10 (p-value) | Epitope sequence | SEQ ID NO: |
|---|---|---|---|---|---|
| HCV-2c (isolate BEBE1) | 1-56 | Core | 2.496 | MSTNPKPQRKTKRNTNRRPQDV KFPGGGQIVGGVYLLPRRGPRL GVRAARKTSERS | 62 |
| HCV-2b (isolate HC-J8) | 1-56 | Core | 2.453 | MSTNPKPQRKTKRNTNRRPQDV KFPGGGQIVGGVYLLPRRGPRL GVRATRKTSERS | 63 |
| HCV-2k (isolate VAT96) | 1-56 | Core | 2.334 | MSTNPKPQRKTKRNTNRRPQDV KFPGGGQIVGGVYLLPRRGPRL GVRATRKTSERS | 64 |
| HCV-2a (isolate HC-J6) | 1-56 | Core | 2.218 | MSTNPKPQRKTKRNTNRRPQDV KFPGGGQIVGGVYLLPRRGPRL GVRATRKTSERS | 65 |
| HCV-2a (isolate JFH-1) | 1-56 | Core | 2.105 | MSTNPKPQRKTKRNTNRRPEDV KFPGGGQIVGGVYLLPRRGPRL GVRTTRKTSERS | 66 |
| HCV-3a (isolate NZL1) | 1-56 | Core | 1.776 | MSTLPKPQRKTKRNTIRRPQDV KFPGGGQIVGGVYVLPRRGPRL GVRATRKTSERS | 67 |
| HCV-3k (isolate JK049) | 1-56 | Core | 1.771 | MSTLPKPQRITKRNINRRPQDV KFPGGGQIVGGVYVLPRRGPKL GVRAVRKTSERS | 68 |
| HCV-3b (isolate Tr-Kj) | 1-56 | Core | 1.483 | MSTLPKPKRQTKRNTLRRPKNV KFPAGGQIVGEVYVLPRRGPQL GVREVRKTSERS | 69 |
| HCV-2c (isolate BEBE1) | 29-84 | Core | 2.470 | QIVGGVYLLPRRGPRLGVRAAR KTSERSQPRGRRQPIPKDRRST GKSWGRPGYPWP | 70 |
| HCV-2b (isolate HC-J8) | 29-84 | Core | 2.438 | QIVGGVYLLPRRGPRLGVRATR KTSERSQPRGRRQPIPKDRRST GKSWGKPGYPWP | 71 |
| HCV-2a (isolate HC-J6) | 29-84 | Core | 2.116 | QIVGGVYLLPRRGPRLGVRATR KTSERSQPRGRRQPIPKDRRST GKSWGKPGYPWP | 72 |
| HCV-3b (isolate Tr-Kj) | 29-84 | Core | 1.548 | QIVGEVYVLPRRGPQLGVREVR KTSERSQPRGRRQPTPKARPRE GRSWAQPGYPWP | 73 |
| HCV-2a (isolate JFH-1) | 29-84 | Core | 1.370 | QIVGGVYLLPRRGPRLGVRTTR KTSERSQPRGRRQPIPKDRRST GKAWGKPGRPWP | 74 |

TABLE 3B-continued

SNP in IL28B gene (rs12979860) association with the epitopes of HCV genotype 2 & 3

| HCV genotype 2 & 3 | HCV amino acid position (start to end) | Viral protein | -log10 (p-value) | Epitope sequence | SEQ ID NO: |
|---|---|---|---|---|---|
| HCV-3b (isolate Tr-Kj) | 57-112 | Core | 2.551 | QPRGRRQPTPKARPREGRSWAQ PGYPWPLYGNEGCGWAGWLLPP RGSRPSWGQNDP | 75 |
| HCV-2a (isolate HC-J6) | 57-112 | Core | 1.902 | QPRGRRQPIPKDRRSTGKSWGK PGYPWPLYGNEGLGWAGWLLSP RGSRPSWGPNDP | 76 |
| HCV-3a (isolate NZL1) | 57-112 | Core | 1.798 | QPRGRRQPIPKARRSEGRSWAQ PGYPWPLYGNEGCGWAGWLLSP RGSRPSWGPNDP | 77 |
| HCV-2a (isolate JFH-1) | 85-140 | Core | 2.926 | LYGNEGLGWAGWLLSPRGSRPS WGPTDPRHRSRNVGKVIDTLTC GFADLMGYIPVV | 78 |
| HCV-2a (isolate HC-J6) | 85-140 | Core | 2.829 | LYGNEGLGWAGWLLSPRGSRPS WGPNDPRHRSRNVGKVIDTLTC GFADLMGYIPVV | 79 |
| HCV-2b (isolate JPUT971017) | 85-140 | Core | 2.733 | LYGNEGCGWAGWLLSPRGSRPT WGPSDPRHRSRNLGRVIDTITC GFADLMGYIPVV | 80 |
| HCV-2k (isolate VAT96) | 85-140 | Core | 1.321 | LYGNEGLGWAGWLLSPRGSRPS WGPTDPRHRSRNLGKVIDTLTC GFADLMGYIPVV | 81 |
| HCV-2c (isolate BEBE1) | 421-476 | E2 | 1.596 | HINRTALNCNDSLETGFLAALF YTSSFNSSGCPERLAACRSIES FRIGWGSLEYEE | 82 |
| HCV-2c (isolate BEBE1) | 645-700 | E2 | 2.197 | QAACNFTRGDRCNLEDRDRSQL SPLLHSTTEWAILPCSYTDLPA LSTGLLHLHQNI | 83 |
| HCV-2c (isolate BEBE1) | 505-560 | E3 | 1.908 | CGPVYCFTPSPVVVGTTDRAGA PTYNWGENETDVFLLNSTRPPK GAWFGCTWMNGT | 84 |
| HCV-2k (isolate VAT96) | 505-560 | E4 | 1.879 | CGPVYCFTPSPVVVGTTDRRGV PTYTWGENDTDVFLLNSTRPPR GAWFGCTWMNST | 85 |
| HCV-2b (isolate JPUT971017) | 505-560 | E5 | 1.563 | CGPVYCFTPSPVVVGTTDRQGV PTYNWGDNETDVFLLNSTRPPR GAWFGCTWMNGT | 86 |
| HCV-2b (isolate HC-J8) | 561-616 | E6 | 1.735 | GFTKTCGAPPCRIRKDYNSTID LLCPTDCFRKHPDATYLKCGAG PWLTPRCLVDYP | 87 |
| HCV-2b (isolate JPUT971017) | 1681-1736 | NS4A | 2.035 | TGCISIIGRIHLNDQVVVAPDK EILYEAFDEMEECASKAALIEE GQRMAEMLKSKI | 88 |
| HCV-2b (isolate HC-J8) | 2101-2156 | NS5A | 1.726 | GSFSYVTGLTSDNLKVPCQVPA PEFFSWVDGVQIHRFAPVPGPF FRDEVTFTVGLN | 89 |
| HCV-2b (isolate JPUT971017) | 2157-2212 | NS5A | 1.518 | SLVVGSQLPCDPEPDTEVLASM LTDPSHITAETAARRLARGSPP SQASSSASQLSA | 90 |
| HCV-3a (isolate k3a) | 2437-2492 | NS5B | 2.676 | TGALITPCSAEEEKLPISPLSN SLLRHHNLVYSTSSRSASQRQK KVTFDRLQVLDD | 91 |

TABLE 3B-continued

| SNP in IL28B gene (rs12979860) association with the epitopes of HCV genotype 2 & 3 | | | | | |
|---|---|---|---|---|---|
| HCV genotype 2 & 3 | HCV amino acid position (start to end) | Viral protein | -log10 (p-value) | Epitope sequence | SEQ ID NO: |
| HCV-3k (isolate JK049) | 2437-2492 | NS5B | 2.533 | ALITPCAAEEEKLPISPLSNSL LRHHNLVYSTSSRSAAQRQKKV TFDRLQVLDDHY | 92 |
| HCV-2b (isolate HC-J8) | 2465-2520 | NS5B | 1.586 | INPLSNSLMRFHNKVYSTTSRS ASLRAKKVTFDRVQVLDAHYDS VLQDVKRAASKV | 93 |
| HCV-3k (isolate JK049) | 2493-2548 | NS5B | 2.245 | NTTLKEIKELASGVKAELLSVE EACRLVPSHSARSKFGYGAKEV RSLSSKAINHIN | 94 |
| HCV-3a (isolate k3a) | 2521-2576 | NS5B | 3.065 | LVPPHSARSKFGYSAKDVRSLS SKAINQIRSVWEDLLEDTTTPI PTTIMAKNEVFC | 95 |
| HCV-2b (isolate HC-J8) | 2521-2576 | NS5B | 1.878 | SARLLTVEEACALTPPHSAKSR YGFGAKEVRSLSRRAVNHIRSV WEDLLEDQHTPI | 96 |
| HCV-2a (isolate JFH-1) | 2521-2576 | NS5B | 1.422 | SARLLTLEEACQLTPPHSARSK YGFGAKEVRSLSGRAVNHIKSV WKDLLEDPQTPI | 97 |
| HCV-3a (isolate k3a) | 2549-2604 | NS5B | 2.591 | IRSVWEDLLEDTTTPIPTTIMA KNEVFCVDPAKGGRKAARLIVY PDLGVRVCEKRA | 98 |
| HCV-3a (isolate NZL1) | 2549-2604 | NS5B | 2.062 | IRSVWEDLLEDTTTPIPTTIMA KNEVFCVDPAKGGRKPARLIVY PDLGVRVCEKRA | 99 |
| HCV-2b (isolate HC-J8) | 2549-2604 | NS5B | 1.767 | EVRSLSRRAVNHIRSVWEDLLE DQHTPIDTTIMAKNEVFCIDPT KGGKKPARLIVY | 100 |
| HCV-2b (isolate HC-J8) | 2661-2716 | NS5B | 1.409 | YDTRCFDSTVTERDIRTEESIY QACSLPQEARTVIHSLTERLYV GGPMTNSKGQSC | 101 |
| HCV-2a (isolate HC-J6) | 2745-2800 | NS5B | 1.565 | CKAAGIIAPTMLVCGDDLVVIS ESQGTEEDERNLRAFTEAMTRY SAPPGDPPRPEY | 102 |

TABLE 3C

| The top significant SNPs associated with VES with p-value $< 10^{-7}$ | | | | | | | |
|---|---|---|---|---|---|---|---|
| Chromosome | SNP | Position(hg19) | Gene Symbol | Allele[1] | VES | nonVES | P value | OR[2] |
| 3 | rs34725101 | 49401262 | RHOA | A/C | 0.15 | 0.03 | 1.23E-10 | 6.03 |
| 9 | rs4483229 | 111980234 | EPB41L4B | A/G | 0.32 | 0.14 | 9.14E-08 | 2.96 |
| 16 | rs16960234 | 83356008 | CDH13 | G/A | 0.19 | 0.06 | 9.20E-08 | 3.75 |

[1]Allels: Minor/Major allele
[2]OR: Odd Ratio

TABLE 4

| VES linked SNPs were associated with disease risk | | | | | | | | |
|---|---|---|---|---|---|---|---|---|
| | Genotype | PC[1](%) | HR[2](%) | HCC[3](%) | OR[4] (95% CI) HCC vs. PC | P-value HCC vs. PC | OR[4] (95% CI) HR vs. PC | P-value HR vs. PC |
| rs34725101 | CC | 391 (97.3%) | 269 (83.3%) | 88 (71.0%) | Ref | Ref | Ref | Ref |
| | CA | 11 (2.7%) | 54 (16.7%) | 36 (29.0%) | 14.5 (7.12-29.7) | 6.32E-16 | 7.14 (3.70-13.9) | 2.64E-11 |
| | AA | 0 | 0 | 0 | | | | |

TABLE 4-continued

VES linked SNPs were associated with disease risk

| | Genotype | PC[1](%) | HR[2](%) | HCC[3](%) | OR[4] (95% CI) HCC vs. PC | P-value HCC vs. PC | OR[4] (95% CI) HR vs. PC | P-value HR vs. PC |
|---|---|---|---|---|---|---|---|---|
| | | (0.0%) | (0.0%) | (0.0%) | | | | |
| | Ptrend[5] | | | | | 0.44 | | 0.72 |
| rs4483229 | GG | 292 (72.6%) | 217 (67.2%) | 75 (60.5%) | Ref | Ref | Ref | Ref |
| | GA | 102 (25.4%) | 96 (29.7%) | 46 (37.1%) | 1.76 (1.14-2.70) | 0.01 | 1.27 (0.90-1.80) | 0.18 |
| | AA | 8 (2.0%) | 10 (3.1%) | 3 (2.4%) | 1.46 (0.38-5.64) | 0.70 | 1.68 (0.70-4.30) | 0.34 |
| | Ptrend | | | | | 0.02 | | 0.09 |
| rsl6960234 | AA | 354 (88.1%) | 281 (87.0%) | 98 (79.0%) | Ref | Ref | Ref | Ref |
| | AG | 46 (11.4%) | 39 (12.1%) | 22 (17.7%) | 1.73 (0.99-3.01) | 0.06 | 1.07 (0.70-1.70) | 0.82 |
| | GG | 2 (0.5%) | 3 (0.9%) | 4 (3.2%) | 7.22 (1.30-40.0) | 0.02 | 1.89 (0.30-11.4) | 0.66 |
| | Ptrend | | | | | 0.003 | | 0.58 |

[1]PC: population control;
[2]HR: high risk group;
[3]HCC: hepatocellular carcinoma;
[4]OR: Odd Ratio
[5]Ptrend: Calculated by wald test from logistic regression

TABLE 5A

Viruses in the 61-VES

| Rank | Feature | Regulation[1] | Importance score[2] |
|---|---|---|---|
| 1 | Hepatitis C virus genotype 3b (isolate Tr-Kj) (HCV) | increased | 9.33% |
| 2 | Hepatitis C virus genotype 1b (isolate Taiwan) (HCV) | increased | 8.13% |
| 3 | Hepatitis C virus genotype 1a (isolate 1) (HCV) | increased | 7.64% |
| 4 | Human cytomegalovirus (strain AD 169) (HHV-5) (Human herpesvirus 5) | increased | 5.01% |
| 5 | Hepatitis C virus genotype 6g (isolate JK046) (HCV) | increased | 3.91% |
| 6 | Epstein-Barr virus (strain B95-8) (HHV-4) (Human herpesvirus 4) | decreased | 3.70% |
| 7 | Humanrhinovirus 23 (HRV-23) | decreased | 3.38% |
| 8 | Human cytomegalovirus (strain Towne) (HHV-5) (Human herpesvirus 5) | decreased | 3.04% |
| 9 | Hepatitis C virus genotype 1b (isolate BK) (HCV) | increased | 3.04% |
| 10 | Human herpesvirus 2 (strain HG52) (HHV-2) (Human herpes simplex virus 2) | decreased | 3.01% |
| 11 | Hepatitis C virus genotype 1c (isolate HC-G9) (HCV) | increased | 2.81% |
| 12 | Human herpesvirus 3 (HHV-3) (Varicella-zoster virus) | decreased | 2.53% |
| 13 | Varicella-zoster virus (strain Dumas) (HHV-3) (Human herpesvirus 3) | decreased | 2.46% |
| 14 | Cercopithecine herpesvirus 16 (CeHV-16) (Herpesvirus papio 2) | decreased | 2.45% |
| 15 | Human adenovirus C serotype 2 (HAdV-2) (Human adenovirus 2) | decreased | 2.34% |
| 16 | Human astrovirus-1 (HAstV-1) | decreased | 2.19% |
| 17 | Human respiratory syncytial virus | decreased | 2.10% |
| 18 | Hepatitis C virus genotype lb (strain HC-J4) (HCV) | increased | 1.92% |
| 19 | Human herpesvirus 6B (strain Z29) (HHV-6 variant B) (Human B lymphotropic virus) | decreased | 1.86% |
| 20 | Hepatitis C virus genotype 4a (isolate ED43) (HCV) | increased | 1.77% |
| 21 | Human herpesvirus 7 (strain JI) (HHV-7) (Human T lymphotropic virus) | decreased | 1.72% |
| 22 | Hepatitis delta virus (HDV) | increased | 1.52% |
| 23 | Human rhino virus 14(HRV-14) | decreased | 1.48% |
| 24 | Lordsdale virus (strain GII/Human/United Kingdom/Lordsdale/1993) (Human enteric calicivirus) (Hu/NV/LD/1993/UK) | decreased | 1.44% |
| 25 | Human herpesvirus 1 (strain KOS) (HHV-1) (Human herpes simplex virus 1) | decreased | 1.42% |
| 26 | Human metapneumovirus (strain CAN97-83) (HMPV) | decreased | 1.40% |
| 27 | Coxsackievirus A16 (strain G-10) | decreased | 1.31% |
| 28 | Epstein-Barr virus (strain AG876) (HHV-4) (Human herpesvirus 4) | decreased | 1.17% |
| 29 | Cowpox virus (CPV) | decreased | 1.14% |
| 30 | Hepatitis C virus genotype 5a (isolate EUH1480) (HCV) | increased | 1.12% |
| 31 | Human cytomegalovirus (HHV-5) (Human herpesvirus 5) | increased | 1.11% |
| 32 | Human herpesvirus 1 (strain 17) (HHV-1) (Human herpes simplex virus 1) | decreased | 0.96% |
| 33 | Human adenovirus E serotype 4 (HAdV-4) (Human adenovirus 4) | decreased | 0.94% |
| 34 | Human adenovirus F serotype 40 (HAdV-40) (Human adenovirus 40) | decreased | 0.87% |
| 35 | Crimean-Congo hemorrhagic fever virus (strain Nigeria/IbArl0200/1970) (CCHFV) | increased | 0.77% |
| 36 | Tanapox virus | decreased | 0.76% |
| 37 | Human adenovirus C serotype 5 (HAdV-5) (Human adenovirus 5) | decreased | 0.72% |

TABLE 5A-continued

Viruses in the 61-VES

| Rank | Feature | Regulation[1] | Importance score[2] |
|---|---|---|---|
| 38 | Rhinovirus B | decreased | 0.70% |
| 39 | Human herpesvirus 8 (HHV-8) (Kaposi's sarcoma-associated herpesvirus) | decreased | 0.61% |
| 40 | Human herpesvirus 6A (strain Uganda-1102) (HHV-6 variant A) (Human B lymphotropic virus) | decreased | 0.59% |
| 41 | Hepatitis C virus genotype lb (isolate HC-JI) (HCV) | increased | 0.57% |
| 42 | Influenza A virus (strain A/USSR/90/1977 H1N1) | increased | 0.50% |
| 43 | Human rhinovirus A serotype 89 (strain 41467-Gallo) (HRV-89) | decreased | 0.50% |
| 44 | Norovirus MD145 (isolate GII/Human/United States/MD 145-12/1987) (Hu/NLV/GII/MD145-12/1987/US) | decreased | 0.42% |
| 45 | Molluscum contagiosum virus subtype 1 (MOCV) (MCVI) | decreased | 0.41% |
| 46 | Vaccinia virus (strain Copenhagen) (VACV) | decreased | 0.36% |
| 47 | Poliovirus type 1 (strain Sabin) | decreased | 0.33% |
| 48 | Orf virus (ORFV) | decreased | 0.32% |
| 49 | Human herpesvirus 2 (strain 333) (HHV-2) (Human herpes simplex virus 2) | decreased | 0.32% |
| 50 | Influenza A virus (strain A/Bangkok/l/1979 H3N2) | increased | 0.30% |
| 51 | Hepatitis C virus genotype 1c (isolate India) (HCV) | increased | 0.26% |
| 52 | Hepatitis B virus (HBV) | decreased | 0.26% |
| 53 | Epstein-Barr virus (strain GDI) (HHV-4) (Human herpesvirus 4) | decreased | 0.25% |
| 54 | Human parainfluenza 3 virus (strain Wash/47885/57) (HPIV-3) (Human parainfluenza 3 virus (strain NIH 47885)) | decreased | 0.21% |
| 55 | Human herpesvirus 2 (HHV-2) (Human herpes simplex virus 2) | decreased | 0.15% |
| 56 | Human enterovirus 71 (strain BrCr) (Ev 71) | decreased | 0.13% |
| 57 | Human herpesvirus 6A (strain GS) (HHV-6 variant A) (Human B lymphotropic virus) | decreased | 0.12% |
| 58 | Chapare virus (isolate Human/Bolivia/8 10419/2003) | increased | 0.10% |
| 59 | Cercopithecine herpesvirus 1 (CeHV-1) (Simian herpes B virus) | decreased | 0.05% |
| 60 | Influenza B virus (strain B/Yamagata/16/1988) | decreased | 0.04% |
| 61 | Influenza A virus (strain A/Philippines/2/1982 H3N2) | decreased | 0.02% |

[1]Regulation: the frequency of the virus feature is higher in disease population (increased) or lower (decreased)

[2]Importance score: the improvement in accuracy brought by a feature to the decision tree branches it is on. The higher the score is, the more important the feature is to the module prediction

TABLE 5B

Most frequent epitopes from the 61-VES

| Virus Name | Epitope sequence | SEQ ID NO: |
|---|---|---|
| Herpesvirus 2 (strain 333) (HHV-2) (Human herpes simplex vims 2) | ELSDTTNATQPELVPEDPEDSALLEDPAGTV SSQIPPNWHIPSIQDVAPHHAPAAP | 1 |
| Cercopithecine herpesvirus 1 (CeHV-1) (Simian herpes B virus) | EVVETANVTRPELAPEERGTSRTPGDEPAPA VAAQLPPNWHVPEASDVTIQGPAPA | 2 |
| Herpesvirus 3 (strain Dumas) (HHV-3) | EKPNATDTPIEEIGDSQNTEPSVNSGFDPDKF REAQEMIKYMTLVSAAERQESKAR | 3 |
| Human respiratory syncytial virus | TPSAESTPQSTTVKTKNTTTTQIQPSKPTTKQ RQNKPQNKPNNDFHFEVFNFVPCS | 4 |
| Cowpox virus (CPV) | IDYDDNKDDDKDDDKDDNKDDDKDDNKD DDKDDKDDNKDDDSDSDSDSDSDSDSDD | 5 |
| Rhinovirus A (serotype 89 strain 41467-Gallo) (HRV-89) | LYSHIKEEDRRRSSAAQAMEAIFQGIDLQSPP PPAIADLLRSVKTPEIIKYCQDNN | 6 |
| Influenza B virus (strain B/Yamagata/ 16/1988) | MSNMDIDGINTGTIDKTPEEITSGTSGTTRPII RPATLAPPSNKRTRNPSPERATT | 7 |
| HCV 3b (isolate Tr-Kj) | LYQQYDEMEECSQSAPYIEQAQAIAQQFKD KVLGLLQRASQQEAEIRPIVQSQWQK | 8 |
| HCV 1b (isolate BK) | YPGHVSGHRMAWDMMMNWSPTTALVVSQ LLRIPQAVVDMVAGAHWGVLAGLAYYSM | 9 |
| HCV 4a (isolate ED43) | RRKRTVQLTESVVSTALAELAAKTFGQSEPS SDRDTDLTTPTETTDSGPIVVDDAS | 10 |
| Cytomegalovirus (HHV-5) | LTVTYSSHTTSAAHSRSGSVSQRVTSSQTVS HGVNETIYNTTLKYGDVVGVNTTKY | 11 |

TABLE 5B-continued

Most frequent epitopes from the 61-VES

| Virus Name | Epitope sequence | SEQ ID NO: |
|---|---|---|
| Influenza A virus (Bangkok H3N2) | CITPNGSIPNDKPFQNVNKITYGACPKYVKQ NTLKLATGMRNVPEKQTR | 12 |
| EBV (strain B95-8) (HHV-4) | TSGATAAASAAAAVDTGSGGGGQPHDTAPR GARKKQ | 13 |
| Herpesvirus 2 (strain HG52) (HHV-2) | MTSRPADQDSVRSSASVPLYPAASPVPAEAY YSESEDEAANDFLVRMGRQQSVLRR | 14 |
| Cercopithecine herpesvirus 16 (CeHV-16) | MEPPRPPDADSLLSDATSVIPLTPPAQGAEAY YTESDDETAADFLMRMGRQQTALR | 15 |
| Human herpesvirus 6B (strain Z29) (HHV-6 variant B) | NFIKISLGETMGITPKEPTNPTQLLNVKNQTE YANETHSTEVQTVKTFKEDRFQRT | 16 |
| Herpesvirus 1 (strain KOS) (HHV-1) | EDEYLSEEMMELTARALERGNGEWSTDAAL EVAHEAEALVSQLGNAGEVFNFGDFG | 17 |
| Herpesvirus 1 (strain 17) (HHV-1) | RRHTQKAPKRIRLPHIREDDQPSSHQPLFY | 18 |
| Adenovirus E serotype 4 (HAdV-4) | QPPLEAPYVPPRYLAPTEGRNSIRYSELTPLY DTTRLYLVDNKSADIASLNYQNDH | 19 |
| Orf virus (ORFV) | SGSRESGSRESGSRESGSREVRESGVRETEVQ VVRVRQESGGRVTAPSESRKKFLD | 20 |
| Influenza A virus (Philippines H3N2) | QNLPGNDNSTATLCLGHHAVPNGTLVKTITN DQIEVTNATELVQSSSTGRICDSPH | 21 |
| Herpesvirus 3 (HHV-3) (Varicella-zoster virus) | TELYTSAASRKPDPAVAPTSAASRKPDPAVA PTSAATRKPDPAVAPTSAATRKPDP | 22 |
| Lordsdale virus (Human enteric calicivirus) (Hu/NV/LD/1993/UK) | LSSMAVTFKRALGGRAKQPPPRETPQRPPRP PTPELVKKIPPPPPNGEDELVVSYS | 23 |
| Norovirus MD 145 | MKMASNDASAAAVANSNNDTAKSSSDGVL SSMAITFKRALGARPKQPPPREILQRP | 24 |
| Vaccinia virus (strain Copenhagen) (VACV) | MDGTLFPGDDDLAIPATEFFSTKADKKPEAK REAIVKADEDDNEETLKQRLTNLEK | 25 |
| Herpesvirus 2 (HHV-2) | DADDHAASFGGLAAAAAGAAGVARKRAFH GDDPFGEGPPEKKDLTLDML | 26 |
| Humanrhinovirus 23 (HRV-23) | KGIIAQNPIENYVDEVLNEVLVVPNINSSHPT TSNSAPALDAAETGHTSNVQPEDV | 27 |
| Herpesvirus 7 (strain JI) (HHV-7) | MGSKCCKTIHGGIFSKAEDTLVDYKGKYINL EKEFSALSDTESEEELQLEKPLLNK | 28 |
| Tanapox virus | MDFMSKYSKELVLTAKNIKDEEPNLNKKET SFDLSTYLKTKETHYQKKIRDQLAEK | 29 |
| Poliovirus type 1 (strain Sabin) | IDNTVRETVGAATSRDALPNTEASGPAHSKE IPALTAVETGATNPLVPSDTVQTRH | 30 |
| Human parainfluenza 3 virus (HPIV-3) (Human parainfluenza 3 virus (strain NIH 47885)) | RLNKRLNDKKKQGSQPSTNPTNRTNQDEID DLFNAFGSN | 31 |
| Human herpesvirus 6A (strain GS) (HHV-6 variant A) | TTNATQKIESTTFTTIGIKEINGNTYSSPKNSI YLKSKSQQSTTKFTDAEHTTPIL | 32 |
| HCV 1b (isolate Taiwan) | MSTNGKPQRKTKRNTNRRPQDVKFPGGGQI VGGVYLLPRRGPRLGVRATRKTWERS | 33 |
| HCV 1a (isolate 1) | MSTNPKPQKKNKRNTNRRPQDVKFPGGGQI VGGVYLLPRRGPRLGVRATRKTSERS | 34 |
| HCV 6g (isolate JK046) (HCV) | MSTNPKPQRQTKRNTNRRPQDVKFPGGGQI VGGVYLLPRRGPRLGVRATRKTSERS | 35 |
| HCV 5a (isolate EUH1480) | NITRVEAENKVEILDCFKPLKEEEDDREISVS ADCFKKGPAFPPALPVWARPGYDP | 36 |

TABLE 5B-continued

Most frequent epitopes from the 61-VES

| Virus Name | Epitope sequence | SEQ ID NO: |
|---|---|---|
| Crimean-Congo hemorrhagic fever virus (strain Nigeria/IbAr10200/1970) (CCHFV) | VRLPHIYHEGVFIPGTYKIVIDKKNKLNDRCT LFTDCVIKGREVRKGQSVLRQYKT | 37 |
| HCV 1b (isolate HC-JI) | MSTIPKPQRKTKRNTNRRPQDVKFPGGGQIV GGVYLLPRRGPRLGVRATRKTSERS | 38 |
| Influenza A virus (strain A/USSR/90/ 1977 H1N1) | SSAGLKNDLLENLQAYQKRMGVQMQRFK | 39 |
| HCV 1c (isolate India) | ITRVESENKIVVLDSFDPLVAEEDDREISIPAE ILRKFKQFPPAMPIWARPDYNPP | 40 |
| Chapare virus (isolate Human/Bolivia/ 810419/2003) | VKKRENMFIDERPGNRNPYENLLYKLCLSGE GWPYIGSRSQVKGRSWENTTVDLSL | 41 |
| Astro virus-1 (HAstV-1) | EDIETDTDIESTEDEDEADRFDIIDTSDEEDEN ETDRVTLLSTLVNQGMTMTRATR | 42 |
| Adenovirus C serotype 5 (HAdV-5) | MAPKKKLQLPPPPTDEEEYWDSQAEEVLDE EEEDMMEDWESLDEEASEVEEVSDET | 43 |
| Human herpesvirus 6A (strain Uganda-1102) (HHV-6 variant A) | EPPAGILAGPQVKPQEKPPAEPPAGLPAGPQ AKPPVKPQAKPPAEPPVGILAGPQA | 44 |
| Cytomegalovirus (strain AD169) (HHV-5) | TASGEEVAVLSHHDSLESRRLREEEDDDDDE DFEDA | 45 |
| HCV 1e (isolate HC-G9) | GSSTTSGVTSGEAAESSPAPSCDGELDSEAES YSSMPPLEGEPGDPDLSDGSWSTV | 46 |
| Cytomegalovirus (strain Towne) (HHV-5) | LDGQTGTQDKGQKPNLLDRLRHRKNGYRH LKDSDEEENV | 47 |
| EBV (strain AG876) (HHV-4) | TGSSQAAPSSSSVAPVASLSGDLEEEEEGSRE SPSLPSSKKGADEFEAWLEAQDAN | 48 |
| HBV | QHFRKLLLLDEEAGPLEEELPRLADEGLNRR VAEDLNLGNLNVSIPWTHKVGNFTG | 49 |
| HDV | PSMQGIPESRFTRTGEGLDVRGSRGFPQDILF PSDPPFSPQSCRPQ | 50 |
| HCV 1b (strain HC-J4) | VIVGRIILSGKPAVVPDREVLYQEFDEMEEC ASQLPYIEQGMQLAEQFKQKALGLL | 51 |
| Adenovirus C serotype 2 (HAdV-2) | GGNNSGSGAEENSNAAAAAMQPVEDMNDH AIRGDTFATRAEEKRAEAEAAAEAAAP | 52 |
| Rhino virus 14 (HRV-14) | TGQVYLLSFISACPDFKLRLMKDTQTISQTV ALTEGLGDELEEVIVEKTKQTVASI | 53 |
| Metapneumovirus (strain CAN97-83) (HMPV) | NFSSLGLTDEEKEAAEHFLNVSDDSQNDYE | 54 |
| Coxsackievirus A16 (strain G-10) | QVEPTAANTNASEHRLGTGLVPALQAAETG ASSNAQDENLIETRCVLNHHSTQETT | 55 |
| Adenovirus F serotype 40 (HAdV-40) | EGVLRCYHGLEMIQKEQLVEMDVASENAQR ALKEHPSRAKVVQNRWGRSVVQLKND | 56 |
| Rhinovirus B | TGQVHLLSFISACPDFKLRLMKDTQTISQTD ALTEGLGDELEEVIVEKTKQTLASV | 57 |
| Herpesvirus 8 (HHV-8) (Kaposi's sarcoma-associated herpesvirus) | EEQEQELEEQEQELEEQEQELEEQEQELEEQ EQELEEQEQELEEQEQELEEQEQEL | 58 |
| Molluscum contagiosum virus subtype 1 (MOCV) (MCVI) | AQAQQAQQAQAQQAQQAQQAQQAQQAQQ AQQAQAQQAQQAQQAQAQQAQAQQAQAQ | 59 |
| EBV (strain GD1) (HHV-4) | SGSGPRHRDGARRPPKRPSCIGC | 60 |
| Enterovirus 71 (strain BrCr) (Ev 71) | SAIGNTIEALFQGPPKFRPIRISLEEKPAPDAIS DLLASVDSEEVRQYCREQGWII | 61 |

TABLE 6

| Viruses in the 31-VES | | | |
|---|---|---|---|
| Viral Strains | Group[1] | LDA score[2] | P-value |
| Human cytomegalovirus (strain AD 169) (HHV-5) (Human herpesvirus 5) | HCC | −448.17% | 0.00% |
| Hepatitis C virus genotype 1b (isolate Taiwan) (HCV) | HCC | −391.18% | 0.00% |
| Human cytomegalovirus (HHV-5) (Human herpesvirus 5) | HCC | −366.42% | 0.59% |
| Hepatitis C virus genotype 1a (isolate 1) (HCV) | HCC | −342.29% | 0.00% |
| Hepatitis C virus genotype 1c (isolate HC-G9) (HCV) | HCC | −335.99% | 0.01% |
| Hepatitis C virus genotype 3b (isolate Tr-Kj) (HCV) | HCC | −332.30% | 0.00% |
| Hepatitis C virus genotype 1b (isolate HC-J1) (HCV) | HCC | −320.54% | 0.17% |
| Hepatitis C virus genotype 6g (isolate JK046) (HCV) | HCC | −318.87% | 0.00% |
| Hepatitis C virus genotype 1b (isolate BK) (HCV) | HCC | −314.50% | 0.00% |
| Hepatitis C virus genotype 1c (isolate India) (HCV) | HCC | −311.55% | 4.67% |
| Hepatitis C virus genotype 1b (strain HC-J4) (HCV) | HCC | −305.44% | 0.04% |
| Hepatitis C virus genotype 4a (isolate ED43) (HCV) | HCC | −300.05% | 0.04% |
| Hepatitis delta virus (HDV) | HCC | −294.22% | 4.48% |
| Hepatitis C virus genotype 5a (isolate EUH1480) (HCV) | HCC | −290.80% | 0.00% |
| Norovirus MD145 (isolate GII/Human/United States/MD145-12/1987) (Hu/NLV/GII/MD145-l 2/1987/US) | PC | 265.06% | 3.37% |
| Human astrovirus-1 (HAstV-1) | PC | 294.42% | 0.25% |
| Human adenovirus F serotype 40 (HAdV-40) (Human adenovirus 40) | PC | 300.70% | 0.93% |
| Coxsackievirus A16 (strain G-10) | PC | 302.42% | 0.73% |
| Human metapneumovirus (strain CAN97-83) (HMPV) | PC | 302.53% | 0.67% |
| Lordsdale virus (strain GII/Human/United Kingdom/Lordsdale/1993) (Human enteric calicivirus) (Hu/NV/LD/1993/UK) | PC | 305.18% | 0.16% |
| Human adenovirus C serotype 5 (HAdV-5) (Human adenovirus 5) | PC | 312.39% | 2.52% |
| Cowpox virus (CPV) | PC | 316.74% | 1.48% |
| Cercopithecine herpesvirus 16 (CeHV-16) (Herpesvirus papio 2) | PC | 317.31% | 0.95% |
| Influenza B virus (strain B/Yamagata/16/1988) | PC | 320.08% | 3.51% |
| Poliovirus type 1 (strain Sabin) | PC | 320.92% | 2.12% |
| Human herpesvirus 3 (HHV-3) (Varicella-zoster virus) | PC | 321.38% | 0.91% |
| Human herpesvirus 7 (strain JI) (HHV-7) (Human T lymphotropic virus) | PC | 348.86% | 0.70% |
| Rhinovirus B | PC | 353.43% | 0.60% |
| Human respiratory syncytial virus | PC | 360.56% | 0.87% |
| Humanrhinovirus 23 (HRV-23) | PC | 360.78% | 0.05% |
| Human herpesvirus 2 (strain HG52) (HHV-2) (Human herpes simplex virus 2) | PC | 392.74% | 1.88% |

[1]PC: population control, HCC: hepatocellular carcinoma

[2]LDA score: Linear discriminant analysis (LDA) effect size, the degree of consistent difference in relative abundance between features in the two groups

TABLE 7

| High Linkage Disequilibrium (LD) SNPs | | | | | | | | |
|---|---|---|---|---|---|---|---|---|
| SNP | Populations[1] | chr[2] | pos (hg38)[3] | R2 | Linked variants | Ref[4] | Alt[5] | eQTL[6] |
| rs16960234 | EUR | 16 | 83373197 | 0.61 | rs79266488 | C | T | Yes |
| rs16960234 | AFR | 16 | 83365352 | 0.61 | rs74034199 | A | G | |
| rs16960234 | EUR | 16 | 83367052 | 0.63 | rs11643358 | A | G | Yes |
| rs16960234 | AFR | 16 | 83282008 | 0.63 | rs60199380 | C | T | |
| rs16960234 | AFR | 16 | 83284440 | 0.63 | rs74031966 | C | T | |
| rs16960234 | EUR | 16 | 83364582 | 0.64 | rs17212165 | G | C | |
| rs16960234 | EUR | 16 | 83365038 | 0.64 | rs113440209 | C | G | |
| rs16960234 | EUR | 16 | 83365095 | 0.64 | rs78895225 | G | A | |
| rs16960234 | EUR | 16 | 83369047 | 0.64 | rs150300998 | G | A | |
| rs16960234 | EUR | 16 | 83369190 | 0.64 | rs76744497 | C | G | Yes |
| rs16960234 | EUR | 16 | 83370348 | 0.64 | rs11647809 | A | G | Yes |
| rs16960234 | EUR | 16 | 83276951 | 0.65 | rs113648214 | A | C | |
| rs16960234 | EUR | 16 | 83356473 | 0.65 | rs17284098 | A | G | |
| rs16960234 | EUR | 16 | 83361752 | 0.65 | rs75150179 | C | T | |
| rs16960234 | EUR | 16 | 83366520 | 0.65 | rs79901975 | T | C | Yes |
| rs16960234 | EUR | 16 | 83366981 | 0.65 | rs11643322 | A | C | Yes |
| rs16960234 | EUR | 16 | 83276270 | 0.66 | rs79704908 | T | C | |
| rs16960234 | EUR | 16 | 83284591 | 0.66 | rs76176371 | G | A | |
| rs16960234 | EUR | 16 | 83285349 | 0.66 | rs75047464 | G | C | |
| rs16960234 | EUR | 16 | 83356730 | 0.66 | rs78862640 | G | A | |
| rs16960234 | EUR | 16 | 83358688 | 0.66 | rs17284265 | A | G | |
| rs16960234 | EUR | 16 | 83363682 | 0.66 | rs 17284390 | A | G | |
| rs16960234 | EUR | 16 | 83365496 | 0.66 | rs75620104 | A | T | |
| rs16960234 | EUR | 16 | 83368938 | 0.66 | rs111838458 | A | G | |
| rs16960234 | EUR | 16 | 83278400 | 0.67 | rs76995467 | T | C | |
| rs16960234 | EUR | 16 | 83361910 | 0.67 | rs74318409 | G | A | |
| rs16960234 | EUR | 16 | 83363403 | 0.67 | rs80149860 | G | A | |
| rs16960234 | EUR | 16 | 83365990 | 0.67 | rs79730292 | A | G | |
| rs16960234 | EUR | 16 | 83366159 | 0.67 | rs75523793 | A | T | |

TABLE 7-continued

High Linkage Disequilibrium (LD) SNPs

| SNP | Populations[1] | chr[2] | pos (hg38)[3] | R2 | Linked variants | Ref[4] | Alt[5] | eQTL[6] |
|---|---|---|---|---|---|---|---|---|
| rs16960234 | EUR | 16 | 83279855 | 0.68 | rs75376892 | C | T | |
| rs16960234 | EUR | 16 | 83361234 | 0.68 | rs118185902 | C | T | |
| rs16960234 | AFR | 16 | 83323628 | 0.69 | rs77449464 | A | T | |
| rs16960234 | AFR | 16 | 83324428 | 0.69 | rs74034143 | A | G | |
| rs16960234 | EUR | 16 | 83281774 | 0.70 | rs117294751 | G | A | |
| rs16960234 | EUR | 16 | 83359841 | 0.71 | rs77436711 | C | T | Yes |
| rs16960234 | EUR | 16 | 83360949 | 0.71 | rs117352383 | T | G | |
| rs16960234 | EUR | 16 | 83348547 | 0.74 | rs74541123 | C | A | |
| rs16960234 | EUR | 16 | 83302079 | 0.75 | rs889729 | A | G | |
| rs16960234 | EUR | 16 | 83303584 | 0.75 | rs74031990 | A | T | |
| rs16960234 | EUR | 16 | 83303787 | 0.75 | rs74031991 | G | T | |
| rs16960234 | EUR | 16 | 83313776 | 0.77 | rs71402061 | A | G | |
| rs16960234 | EUR | 16 | 83317816 | 0.77 | rs76225392 | G | A | |
| rs16960234 | AFR | 16 | 83310864 | 0.78 | rs57810667 | A | C | |
| rs16960234 | AFR | 16 | 83313310 | 0.78 | rs74034109 | T | G | |
| rs16960234 | EUR | 16 | 83289953 | 0.80 | rs929893 | A | T | |
| rs16960234 | EUR | 16 | 83290218 | 0.80 | rs929895 | T | C | |
| rs16960234 | EUR | 16 | 83295757 | 0.80 | rs76816724 | T | G | |
| rs16960234 | EUR | 16 | 83289363 | 0.81 | rs77652642 | G | C | |
| rs16960234 | EUR | 16 | 83299164 | 0.81 | rs79282218 | T | G | |
| rs16960234 | AFR | 16 | 83321413 | 0.81 | rs74034139 | C | A | |
| rs16960234 | AFR | 16 | 83321685 | 0.81 | rs113201349 | T | C | |
| rs16960234 | EUR | 16 | 83290746 | 0.83 | rs79858538 | G | A | |
| rs16960234 | EUR | 16 | 83300167 | 0.83 | rs76296650 | A | G | |
| rs16960234 | EUR | 16 | 83326962 | 0.83 | rs76158834 | C | A | |
| rs16960234 | EUR | 16 | 83326986 | 0.83 | rs74538806 | G | T | |
| rs16960234 | AFR | 16 | 83308296 | 0.83 | rs74034105 | G | T | |
| rs16960234 | AFR | 16 | 83329699 | 0.83 | rs57066373 | T | G | |
| rs16960234 | AFR | 16 | 83332460 | 0.83 | rs74034164 | A | G | |
| rs16960234 | EUR | 16 | 83310319 | 0.84 | rs77635880 | G | C | |
| rs16960234 | EUR | 16 | 83314717 | 0.84 | rs 17282232 | G | A,C | |
| rs16960234 | EUR | 16 | 83317522 | 0.84 | rs17210046 | C | A,T | |
| rs16960234 | EUR | 16 | 83326143 | 0.84 | rs12325503 | T | C | |
| rs16960234 | EUR | 16 | 83326206 | 0.84 | rs10514578 | G | A | |
| rs16960234 | EUR | 16 | 83326800 | 0.84 | rs76742309 | G | A | |
| rs16960234 | EUR | 16 | 83329485 | 0.84 | rs75225088 | C | T | |
| rs16960234 | EUR | 16 | 83330172 | 0.84 | rs76719419 | T | C | |
| rs16960234 | EUR | 16 | 83311620 | 0.85 | rs77055246 | T | C | |
| rs16960234 | EUR | 16 | 83321413 | 0.85 | rs74034139 | C | A | |
| rs16960234 | EUR | 16 | 83325540 | 0.85 | rs76664463 | G | A | |
| rs16960234 | EUR | 16 | 83325680 | 0.85 | rs76598341 | C | A | |
| rs16960234 | EUR | 16 | 83324428 | 0.87 | rs74034143 | A | G | |
| rs16960234 | EUR | 16 | 83291577 | 0.88 | rs77378326 | C | G | |
| rs16960234 | EUR | 16 | 83323628 | 0.88 | rs77449464 | A | T | |
| rs16960234 | AFR | 16 | 83303938 | 0.89 | rs74031992 | C | T | |
| rs16960234 | AFR | 16 | 83304034 | 0.89 | rs74034104 | G | T | |
| rs16960234 | AFR | 16 | 83313830 | 0.89 | rs74034111 | T | C | |
| rs16960234 | AFR | 16 | 83315207 | 0.89 | rs16960229 | G | A | |
| rs16960234 | AFR | 16 | 83315877 | 0.89 | rs74034113 | G | C | |
| rs16960234 | AFR | 16 | 83315970 | 0.89 | rs74034114 | G | T | |
| rs16960234 | AFR | 16 | 83323462 | 0.89 | rs78340799 | G | A | |
| rs16960234 | AFR | 16 | 83325793 | 0.89 | rs74034145 | G | A | |
| rs16960234 | AFR | 16 | 83325990 | 0.89 | rs74034146 | A | G | |
| rs16960234 | AFR | 16 | 83326600 | 0.89 | rs57413765 | G | A | |
| rs16960234 | AFR | 16 | 83326886 | 0.89 | rs74034149 | G | C | |
| rs16960234 | AFR | 16 | 83327240 | 0.89 | rs74034150 | A | G | |
| rs16960234 | AFR | 16 | 83327785 | 0.89 | rs74034151 | G | C | |
| rs16960234 | AFR | 16 | 83341951 | 0.89 | rs74034173 | G | C | |
| rs16960234 | EUR | 16 | 83308892 | 0.91 | rs2325934 | A | C | |
| rs16960234 | EUR | 16 | 83309121 | 0.91 | rs80088527 | C | A | |
| rs16960234 | EUR | 16 | 83309271 | 0.91 | rs75586590 | C | G | |
| rs16960234 | EUR | 16 | 83309487 | 0.91 | rs111918530 | C | T | |
| rs16960234 | EUR | 16 | 83309753 | 0.91 | rs76343373 | C | T | |
| rs16960234 | EUR | 16 | 83297254 | 0.93 | rs78794145 | G | C | |
| rs16960234 | EUR | 16 | 83307307 | 0.93 | rs75001885 | A | G | |
| rs16960234 | EUR | 16 | 83319327 | 0.93 | rs10514582 | G | A | |
| rs16960234 | EUR | 16 | 83335615 | 0.93 | rs112288081 | G | A | |
| rs16960234 | EUR | 16 | 83346132 | 0.93 | rs17211581 | G | A | |
| rs16960234 | EUR | 16 | 83302117 | 0.94 | rs79028139 | G | C | |
| rs16960234 | EUR | 16 | 83318106 | 0.94 | rs75473666 | T | C | |
| rs16960234 | EUR | 16 | 83319768 | 0.94 | rs10514580 | G | T | |
| rs16960234 | EUR | 16 | 83320534 | 0.94 | rs79784474 | G | A | |
| rs16960234 | EUR | 16 | 83336458 | 0.94 | rs76161362 | G | C | |
| rs16960234 | EUR | 16 | 83339005 | 0.94 | rs79780526 | A | G | |
| rs16960234 | EUR | 16 | 83341936 | 0.94 | rs17211371 | T | C | |
| rs16960234 | EUR | 16 | 83342784 | 0.94 | rs78860402 | A | C | |

TABLE 7-continued

| | | | | High Linkage Disequilibrium (LD) SNPs | | | | |
|---|---|---|---|---|---|---|---|---|
| SNP | Populations[1] | chr[2] | pos (hg38)[3] | R2 | Linked variants | Ref[4] | Alt[5] | eQTL[6] |
| rs16960234 | AFR | 16 | 83319867 | 0.94 | rs74034115 | C | G | |
| rs16960234 | EUR | 16 | 83313411 | 0.96 | rs79842380 | A | T | |
| rs16960234 | EUR | 16 | 83327178 | 0.96 | rs79131725 | A | T | |
| rs16960234 | EUR | 16 | 83327459 | 0.96 | rs17210599 | A | G | |
| rs16960234 | EUR | 16 | 83330141 | 0.96 | rs77866289 | G | A | |
| rs16960234 | EUR | 16 | 83340212 | 0.96 | rs10514575 | T | C | |
| rs16960234 | EUR | 16 | 83344491 | 0.96 | rs1424168 | A | G | |
| rs16960234 | EUR | 16 | 83325526 | 0.97 | rs77980290 | C | T | |
| rs16960234 | EUR | 16 | 83321587 | 0.99 | rs112285137 | G | T | |
| rs16960234 | EUR | 16 | 83321611 | 0.99 | rs80170986 | C | T | |
| rs16960234 | EUR | 16 | 83321620 | 0.99 | rs75636201 | C | G | |
| rs16960234 | EUR | 16 | 83321685 | 0.99 | rs113201349 | T | C | |
| rs16960234 | EUR | 16 | 83322403 | 1.00 | rs16960234 | T | C | |
| rs16960234 | EUR | 16 | 83322838 | 1.00 | rs17210298 | A | G | |
| rs16960234 | AFR | 16 | 83321587 | 1.00 | rs112285137 | G | T | |
| rs16960234 | AFR | 16 | 83321611 | 1.00 | rs80170986 | C | T | |
| rs16960234 | AFR | 16 | 83321620 | 1.00 | rs75636201 | C | G | |
| rs16960234 | AFR | 16 | 83322403 | 1.00 | rs16960234 | T | C | |
| rs34725101 | EUR | 3 | 49363829 | 1.00 | rs34725101 | C | A | |
| rs34725101 | AFR | 3 | 49363829 | 1.00 | rs34725101 | C | A | |
| rs4483229 | EUR | 9 | 109217954 | 1.00 | rs4483229 | G | A | |
| rs4483229 | AFR | 9 | 109217954 | 1.00 | rs4483229 | G | A | |

[1]EUR is European and AFR is African from 1000G Phase 1 population
[2]chr is chromatin
[3]pos(hg38) is the position on human reference genome version 38
[4]Ref stands for reference sequence
[5]Alt stands for alternative sequence
[6]eQTL is Expression quantitative trait loci; eQTL information is from gtexportal.org/home/

TABLE 8

| | | | | Clinical characteristics of 899 patients and volunteers from NCI-UMD cohort | | | |
|---|---|---|---|---|---|---|---|
| Variable | PC[1] (N = 412) | HR[2] (N = 337) | HCC[3] (N = 150) | P-value[4] (PC vs. HCC) | P-value (PC vs. HR) | P-value (HR vs. HCC) |
| Age-year | | | | 0.12 | 0.01 | 0.86 |
| Median (Range) | 61 (46-79) | 58 (41-80) | 61 (19-87) | | | |
| Missing data | 0 (0.0) | 0 (0.0) | 2 (1.3) | | | |
| Sex-no. (%) | | | | 1.00 | 0.46 | 0.58 |
| Female | 74 (18.0) | 68 (20.2) | 27 (18.0) | | | |
| Male | 338 (82.0) | 269 (79.8) | 123 (82.0) | | | |
| Missing data | 0 (0.0) | 0 (0.0) | 0 (0.0) | | | |
| Race-no. (%) | | | | <0.0001 | 0.22 | <0.0001 |
| European American | 141 (34.2) | 130 (38.6) | 77 (51.3) | | | |
| African American | 271 (65.8) | 206 (61.1) | 57 (38.0) | | | |
| Asian American | 0 (0.0) | 1 (0.3) | 7 (4.7) | | | |
| Other | 0 (0.0) | 0 (0.0) | 2 (1.3) | | | |
| Missing data | 0 (0.0) | 0 (0.0) | 7 (4.7) | | | |
| HCV only-no. (%) (diagnosed positive) | | 272 (80.7) | 68 (45.3) | | | 0.08 |
| HBV only-no. (%) (diagnosed positive) | | 8 (2.4) | 6 (4.0) | | | |
| HBV + HCV-no. (%) (diagnosed positive) | | 14 (4.2) | 6 (4.0) | | | |
| HBV + HDV-no. (%) (diagnosed positive) | | 0 (0.0) | 0 (0.0) | | | |
| Others not hepatitis infection | | 0 (0.0) | 0 (0.0) | | | |
| Cirrhosis-no. (%) (diagnosed positive) | | 163 (48.4) | 80 (53.3) | | | <0.00001 |
| Missing data | | 2 (0.6) | 47 (31.3) | | | |
| Alanine aminotransferase-no. (%) | | | | | | <0.001 |
| Elevated (>50 U/L) | | 108 (32.0) | 57 (38.0) | | | |
| Normal (<50 U/L) | | 210 (62.3) | 51 (34.0) | | | |
| Alpha-fetoprotein-no. (%) | | | | | | <0.00001 |
| >20 ng/mL | | 15 (4.5) | 38 (25.3) | | | |
| ≤20 ng/mL | | 99 (29.4) | 34 (22.7) | | | |

TABLE 8-continued

Clinical characteristics of 899 patients and volunteers from NCI-UMD cohort

| Variable | PC[1] (N = 412) | HR[2] (N = 337) | HCC[3] (N = 150) | P-value[4] (PC vs. HCC) | P-value (PC vs. HR) | P-value (HR vs. HCC) |
|---|---|---|---|---|---|---|
| Missing data Survival (months) | | | | | | |
| Median | | | 25.4 | | | |
| Range | | | 0.5->40 | | | |
| Missing data (%) | | | 12 (8.0) | | | |

[1]PC: population control;
[2]HR: high risk group;
[3]HCC: hepatocellular carcinoma;
[4]P-value: p-value was calculated by t-test or Chi-seq test, with 2 tailed

TABLE 9A

Univariable and multivariable analyses of factors associated with survival of NCI-UMD cohort

| Clinical variable | Univariable analysis[a] Hazard ratio (95% CI) | P-value | Multivariable analysis[b] Hazard ratio (95% CI) | P-value |
|---|---|---|---|---|
| VES | 1.40(1.04-1.82) | 0.025 | 2.17(0.39-12.08) | 0.377 |
| Age | 0.86(0.54-1.38) | 0.528 | 1.02(0.97-1.08) | 0.359 |
| HCV (diagnosis positive versus negative) | 1.40(0.80-2.58) | 0.221 | 0.70(0.26-1.90) | 0.479 |
| HBV (diagnosis positive versus negative) | 0.79(0.31-1.98) | 0.614 | 1.19(0.35-4.04) | 0.777 |
| Cirrhosis (1 versus 0) | 1.20(0.64-2.30) | 0.554 | 0.90(0.36-2.24) | 0.824 |
| AFP (>=20 ng/ml versus <20 ng/ml) | 2.70(1.34-5.44) | 0.005 | 2.92(1.21-7.08) | 0.018 |
| ALT (>=50 U/L versus <50 U/L) | 1.40 (0.83-2.40) | 0.210 | 1.76 (0.76-4.10)) | 0.189 |

[a]Univariable Cox regression.
[b]Multivariable Cox regression.

TABLE 9B

Multivariable Cox regression of HCC diagnosis on the NIDDK cohort predicted with the VES signature at baseline (adjusted for clinical prognostic variables)

| | |
|---|---|
| Number of events | 36 |
| Regression coefficients (standard error) | |
| VES score | 1.06 (0.69) |
| Hep B | 3.21 (1.41) |
| Hep C | 2.35 (1.37) |
| NAFLD | 0.40 (1.63) |
| Cirrhosis | 1.55 (0.64) |
| Diabetes | 0.80 (0.69) |
| ALT | −0.0004 (0.002) |
| Creatinine | −0.55 (0.85) |
| Albumin | −1.41 (0.67) |
| Bilirubin Tot | −0.35 (0.89) |
| PLT | −0.006 (0.004) |
| Prothromb T | −0.03 (0.23) |
| AFP | −0.04 (0.54) |
| Concordance (standard error) | 0.817 (0.053) |
| Likelihood ratio test p-value | 0.000002 |
| Wald test p-value | 0.0003 |
| Logrank test p-value | 0.0000004 |

TABLE 9C

Prediction performance within HCV+ and HCV− subcohorts

| Cohort | Subcohort | | AUC | AUC (95% CI upper) |
|---|---|---|---|---|
| NIDDK at baseline | HCV− | 1 | 1 | 1 |
| NIDDK at baseline | HCV+ | 1 | 1 | 1 |
| NIDDK at diagnosis | HCV− | 1 | 1 | 1 |
| NIDDK at diagnosis | HCV+ | 1 | 1 | 1 |
| NCI-UMD | HCV− | 1 | 1 | 1 |
| NCI-UMD | HCV+ | 0.91 | 0.95 | 0.99 |

In view of the many possible embodiments to which the principles of the disclosed subject matter may be applied, it should be recognized that the illustrated embodiments are only examples of the disclosure and should not be taken as limiting the scope of the disclosure. Rather, the scope of the disclosure is defined by the following claims. We therefore claim all that comes within the scope and spirit of these claims.

The invention claimed is:

1. A method of identifying a subject with early stage hepatocellular carcinoma (HCC), comprising:

(i) detecting the presence or absence of antibodies to a plurality of virus epitopes in a sample obtained from the subject, wherein the plurality of virus epitopes comprises epitopes from the 61 viruses listed in Table 5A, and wherein the amino acid sequences of the plurality of virus epitopes are set forth as SEQ ID NOs: 1-61;

(ii) determining the presence of a viral exposure signature (VES) in the sample obtained from the subject if:

(a) antibodies specific for the epitopes of hepatitis C virus (HCV) genotype 3b, isolate Tr-Kj; HCV genotype 1b, isolate Taiwan; HCV genotype 1a, isolate 1; human cytomegalovirus, strain AD169; HCV genotype 6g, isolate JK046; HCV genotype 1b, isolate BK; HCV genotype 1c, isolate HC-G9; HCV genotype 1b, strain HC-J4; HCV genotype 4a, isolate ED43; hepatitis delta virus; HCV genotype 5a, isolate EUH1480; human cytomegalovirus; Crimean-Congo hemorrhagic fever virus, strain Nigeria/IbAr10200/1970; HCV genotype 1b, isolate HC-J1; influenza A virus, strain A/USSR/90/1977 H1N1; influenza A virus, strain A/Bangkok/1/1979 H3N2; HCV genotype 1c, isolate India; and Chapare virus, isolate Human/Bolivia/810419/2003 are detected in the sample; and (b) antibodies specific for the epitopes of Epstein-Barr virus, strain B95-8; human rhinovirus 23; HCMV, strain Towne; human herpesvirus 2 (HHV-2), strain HG52; human herpesvirus 3; varicella-zoster virus, strain Dumas; Cercopithecine herpesvirus 16; human adenovirus C serotype 2; human astrovirus-1; human respiratory syncytial virus; human herpesvirus 6B, strain Z29; human herpesvirus 7, strain JI; human rhinovirus 14; Lordsdale virus, strain GII/Human/United Kingdom/Lordsdale/1993; human herpesvirus 1, strain KOS; human metapneumovirus, strain CAN97-83; coxsackievirus A16, strain G-10; Epstein-Barr virus, strain AG876; cowpox virus; human herpesvirus 1, strain 17; human adenovirus E serotype 4; human adenovirus F serotype 40; tanapox virus; human adenovirus C serotype 5; rhinovirus B; human herpesvirus 8; human herpesvirus 6A, strain Uganda-1102; human rhinovirus A serotype 89, strain 41467-Gallo; norovirus MD145, isolate GII/Human/United States/MD145-12/1987; molluscum contagiosum virus subtype 1; vaccinia virus, strain Copenhagen; poliovirus type 1, strain Sabin; orf virus; HHV-2, strain 333; hepatitis B virus; Epstein-Barr virus, strain GD1; human parainfluenza 3 virus, strain Wash/47885/57; HHV-2; human enterovirus 71, strain BrCr; human herpesvirus 6A, strain GS; Cercopithecine herpesvirus 1; influenza B virus, strain B/Yamagata/16/1988; and influenza A virus, strain A/Philippines/2/1982 H3N2 are not detected in the sample; and (iii) identifying the subject as having early stage HCC when the VES is present.

2. The method of claim 1, wherein the plurality of viruses consists of the 61 viruses listed in Table 5A.

3. The method of claim 1, wherein the sample is a blood or serum sample.

4. The method of claim 1, wherein the antibodies are detected by phage immunoprecipitation, immunoblot or enzyme-linked immunosorbent assay.

5. The method of claim 1, further comprising administering an appropriate therapy for the prevention or treatment of HCC.

6. The method of claim 5, wherein the appropriate therapy comprises vaccination against HBV, vaccination against HCV, administration of an anti-viral drug, a lifestyle change or a dietary modification.

7. The method of claim 6, wherein the anti-viral drug is a nucleoside analog, interferon, or lamivudine.

8. The method of claim 6, wherein the lifestyle or diet change includes reducing or eliminating intravenous drug use, reducing or eliminating alcohol consumption, reducing exposure to aflatoxin, or reducing iron overload.

9. The method of claim 5, wherein the appropriate therapy comprises a liver transplant or liver resection.

10. The method of claim 9, further comprising radiofrequency ablation.

11. The method of claim 1, further comprising diagnostic monitoring every 3 months or every 6 months of the subject with early stage HCC.

12. The method of claim 11, wherein diagnostic monitoring comprises ultrasound, computerized tomography (CT), magnetic resonance imaging (MRI), or a combination thereof.

13. The method of claim 1, wherein the subject has not previously had a diagnosis of one or more of liver disease, hepatitis B virus (HBV) infection, hepatitis C virus (HCV) infection, hepatitis delta virus (HDV) infection, nonalcoholic fatty-liver disease (NAFLD), nonalcoholic steatohepatitis (NASH) and hepatocellular carcinoma (HCC).

* * * * *